United States Patent
Chandler et al.

[11] Patent Number: 5,877,028
[45] Date of Patent: Mar. 2, 1999

[54] IMMUNOCHROMATOGRAPHIC ASSAY DEVICE

[75] Inventors: Howard M. Chandler, Yarmouth; Roger N. Piasio, Cumberland; Karen Prouty, West Buxton, all of Me.

[73] Assignee: SmithKline Diagnostics, Inc., Palo Alto, Calif.

[21] Appl. No.: 40,430

[22] Filed: Mar. 31, 1993

Related U.S. Application Data

[63] Continuation-in-part of Ser. No. 888,831, May 27, 1992, abandoned, which is a continuation-in-part of Ser. No. 706,639, May 29, 1991.

[51] Int. Cl.⁶ .................................................. G01N 33/558
[52] U.S. Cl. ............................. 436/514; 422/56; 422/58; 422/60; 435/7.92; 435/7.93; 435/7.94; 435/7.95; 435/287.1; 435/287.2; 435/287.7; 435/287.9; 435/970; 435/975; 435/805; 435/810; 436/501; 436/518; 436/169; 436/805; 436/810
[58] Field of Search ........................ 435/7.1, 7.92, 435/7.93, 7.94, 7.95, 287.1, 287.2, 287.7, 287.9, 970, 975, 810, 805; 436/514, 501, 578, 169, 810, 805; 422/56, 58, 60, 59

[56] References Cited

U.S. PATENT DOCUMENTS

| | | | |
|---|---|---|---|
| Re. 30,267 | 5/1980 | Bruschi | 23/230 B |
| Re. 31,006 | 8/1982 | Schuurs et al. | 435/7.8 |

(List continued on next page.)

FOREIGN PATENT DOCUMENTS

| | | |
|---|---|---|
| 0063810 | 11/1982 | European Pat. Off. . |
| 0088636 | 9/1983 | European Pat. Off. . |
| 0125118 | 11/1984 | European Pat. Off. . |
| 0154749 | 9/1985 | European Pat. Off. . |
| 0170746 | 2/1986 | European Pat. Off. . |
| 0183442 | 6/1986 | European Pat. Off. . |
| 0191640 | 8/1986 | European Pat. Off. . |
| 0217403 | 4/1987 | European Pat. Off. . |
| 0225054 | 6/1987 | European Pat. Off. . |
| 0227173 | 7/1987 | European Pat. Off. . |
| 0238012 | 9/1987 | European Pat. Off. . |
| 0250137 | 12/1987 | European Pat. Off. . |
| 0259157 | 3/1988 | European Pat. Off. . |
| 0262328 | 4/1988 | European Pat. Off. . |
| 0267724 | 5/1988 | European Pat. Off. . |
| 0269362 | 6/1988 | European Pat. Off. . |
| 0269876 | 6/1988 | European Pat. Off. . |
| 0271204 | 6/1988 | European Pat. Off. . |

(List continued on next page.)

OTHER PUBLICATIONS

Wilchek, et al., "The Avidin–Biotin Complex in Immunology", Immunology Today (1984), vol. 5, No. 2, pp. 39–43.
Copy of International Search Report for corresponding PCT application serial No. US96/07576 filed on May 23, 1996.

*Primary Examiner*—Christopher L. Chin
*Attorney, Agent, or Firm*—William H. May; P. R. Harder; Merchant & Gould

[57] ABSTRACT

A chromatographic assay device for use with immunoassays allows rapid and convenient assays of analytes of biological interest, and permits extractions to be carried out in situ, avoiding the use of separate extraction vessels. The device has a wide dynamic range and avoids interference from particulates or colored components. In one form, the device comprises: (1) a first opposable component comprising a sample preparation zone adapted to receive a sample to be assayed; and (2) a second opposable component comprising a chromatographic medium. The first and second opposable components can be brought into opposition so as to cause the sample preparation zone to apply the sample to be tested to the chromatographic medium. Preferably, the analyte is detected with a visually detectable label. Other variations of the device vary the arrangement of components to provide optimal chromatography for a variety of analytes, as well as to permit bidirectional chromatography; still other variations are suitable for competitive immunoassays. The devices can be incorporated in test kits, and assay methods, both sandwich and competitive, using the devices are also disclosed.

83 Claims, 13 Drawing Sheets

U.S. PATENT DOCUMENTS

| | | | |
|---|---|---|---|
| 1,926,299 | 9/1933 | Monk | 206/45.29 |
| 3,078,031 | 2/1963 | Kauffeld | 229/208 |
| 3,186,623 | 6/1965 | Guyer | 229/207 |
| 3,307,770 | 3/1967 | Wysocki | 229/23 |
| 3,420,205 | 1/1969 | Morison | 116/200 |
| 3,437,449 | 4/1969 | Luckey | 422/85 |
| 3,475,129 | 10/1969 | Peurifoy et al. | 436/120 |
| 3,551,555 | 12/1970 | Schuurs | 424/12 |
| 3,720,760 | 3/1973 | Bennich et al. | 424/1 |
| 3,723,064 | 3/1973 | Liotta | 436/66 |
| 3,798,004 | 3/1974 | Zerachia et al. | 422/56 |
| 3,811,840 | 5/1974 | Bauer et al. | 422/56 |
| 3,867,517 | 2/1975 | Ling | 421/1 |
| 3,888,629 | 6/1975 | Bagshawe | 23/230 B |
| 3,893,808 | 7/1975 | Campbell | 23/253 TP |
| 3,901,657 | 8/1975 | Lightfoot | 23/253 TP |
| 3,902,964 | 9/1975 | Greenspan . | |
| 3,915,647 | 10/1975 | Wright | 23/253 TP |
| 3,926,564 | 12/1975 | Giaever | 23/259 |
| 3,932,220 | 1/1976 | Liotta | 195/103.5 R |
| 3,933,594 | 1/1976 | Milligan et al. | 195/103.5 R |
| 3,933,997 | 1/1976 | Hersh et al. | 424/1 |
| 3,935,074 | 1/1976 | Rubenstein et al. | 195/103.5 R |
| 3,949,064 | 4/1976 | Bornstein et al. | 436/527 |
| 3,951,332 | 4/1976 | Torbeck | 229/241 |
| 3,960,499 | 6/1976 | White | 23/253 R |
| 3,961,894 | 6/1976 | Gordon et al. | 23/230.6 |
| 3,966,897 | 6/1976 | Renn et al. | 424/1.5 |
| 3,975,162 | 8/1976 | Renn | 23/253 TP |
| 3,979,509 | 9/1976 | Giaver | 424/12 |
| 3,981,981 | 9/1976 | Reunanen | 436/535 |
| 3,984,533 | 10/1976 | Uzgiris | 436/516 |
| 3,985,867 | 10/1976 | Redshaw | 436/500 |
| 3,989,591 | 11/1976 | Liotta | 195/1.8 |
| 3,990,850 | 11/1976 | Friedman et al. | 23/230 B |
| 3,992,158 | 11/1976 | Przybylowicz et al. | 23/253 TP |
| 3,993,451 | 11/1976 | Verbeck | 422/57 |
| 3,996,158 | 12/1976 | Pagano | 23/253 |
| 4,012,198 | 3/1977 | Finter et al. | 23/253 R |
| 4,016,043 | 4/1977 | Schuurs et al. | 195/103.5 R |
| 4,017,597 | 4/1977 | Reynolds | 424/1.5 |
| 4,018,662 | 4/1977 | Ruhenstroth-Bauer et al. | 204/299 R |
| 4,020,151 | 4/1977 | Bolz et al. | 436/527 |
| 4,038,485 | 7/1977 | Johnston et al. | 435/4 |
| 4,039,652 | 8/1977 | Adams et al. | 424/1 |
| 4,042,335 | 8/1977 | Clement | 23/253 TP |
| 4,046,514 | 9/1977 | Johnston et al. | 422/56 |
| 4,053,284 | 10/1977 | Posch | 23/259 |
| 4,054,646 | 10/1977 | Giaver | 424/12 |
| 4,059,407 | 11/1977 | Hochstrasser | 23/253 TP |
| 4,065,383 | 12/1977 | Skare et al. | 210/27 |
| 4,066,403 | 1/1978 | Bruschi | 23/230 B |
| 4,067,774 | 1/1978 | Rubenstein et al. | 195/63 |
| 4,067,959 | 1/1978 | Bolz | 424/1 |
| 4,087,326 | 5/1978 | Kereluk | 195/103.5 R |
| 4,087,332 | 5/1978 | Hansen | 195/127 |
| 4,094,647 | 6/1978 | Deutsch et al. | 23/253 TP |
| 4,108,729 | 8/1978 | Mannen | 195/127 |
| 4,108,972 | 8/1978 | Dreyer | 436/534 |
| 4,108,976 | 8/1978 | Reese | 424/1 |
| 4,110,079 | 8/1978 | Schaeffer et al. | 23/253 TP |
| 4,116,638 | 9/1978 | Kenoff | 422/99 |
| 4,123,224 | 10/1978 | Givner et al. | 422/59 |
| 4,123,509 | 10/1978 | Banik et al. | 424/12 |
| 4,128,399 | 12/1978 | Liotta et al. | 23/230 B |
| 4,129,417 | 12/1978 | White | 436/169 |
| 4,130,462 | 12/1978 | Rubenstein et al. | 195/103.5 A |
| 4,133,639 | 1/1979 | Harte | 23/230 B |
| 4,134,792 | 1/1979 | Boguslaski et al. | 195/99 |
| 4,144,306 | 3/1979 | Figueras | 422/56 |
| 4,145,186 | 3/1979 | Andersen | 436/1 |
| 4,145,406 | 3/1979 | Schick et al. | 436/541 |
| 4,153,668 | 5/1979 | Hill et al. | 422/56 |
| 4,157,323 | 6/1979 | Yen et al. | 260/29.7 M |
| 4,160,008 | 7/1979 | Fenocketti et al. | 422/56 |
| 4,166,102 | 8/1979 | Johnson | 424/1 |
| 4,168,146 | 9/1979 | Grubb et al. | 23/230 B |
| 4,169,138 | 9/1979 | Jonsson | 436/524 |
| 4,175,923 | 11/1979 | Friend | 23/230 B |
| 4,177,253 | 12/1979 | Davies et al. | 424/1 |
| 4,189,304 | 2/1980 | Adams et al. | 23/230 B |
| 4,200,690 | 4/1980 | Root et al. | 435/7 |
| 4,205,058 | 5/1980 | Wagner et al. | 424/1 |
| 4,205,952 | 6/1980 | Cais | 23/230 B |
| 4,210,418 | 7/1980 | Brown et al. | 23/230 B |
| 4,219,335 | 8/1980 | Ebersole | 23/230 B |
| 4,223,089 | 9/1980 | Rothe et al. | 435/12 |
| 4,228,237 | 10/1980 | Hevey et al. | 435/7 |
| 4,233,029 | 11/1980 | Columbus | 436/174 |
| 4,233,402 | 11/1980 | Maggio et al. | 435/7 |
| 4,235,601 | 11/1980 | Deutsch et al. | 23/230 R |
| 4,237,234 | 12/1980 | Meunier | 435/301 |
| 4,238,565 | 12/1980 | Hornby et al. | 435/7 |
| 4,243,749 | 1/1981 | Sadeh et al. | 435/7 |
| 4,244,694 | 1/1981 | Farina et al. | 23/230 B |
| 4,246,339 | 1/1981 | Cole et al. | 435/7 |
| 4,248,829 | 2/1981 | Kitajima et al. | 422/56 |
| 4,254,082 | 3/1981 | Schick et al. | 422/55 |
| 4,254,083 | 3/1981 | Columbus | 422/55 |
| 4,255,384 | 3/1981 | Kitajima et al. | 422/57 |
| 4,256,693 | 3/1981 | Kondo et al. | 422/56 |
| 4,258,001 | 3/1981 | Pierce et al. | 422/96 |
| 4,268,270 | 5/1981 | Gabbay et al. | 23/230.3 |
| 4,270,921 | 6/1981 | Graas | 23/230 B |
| 4,271,119 | 6/1981 | Columbus | 422/50 |
| 4,274,832 | 6/1981 | Wu et al. | 435/11 |
| 4,275,149 | 6/1981 | Litman et al. | 435/7 |
| 4,279,617 | 7/1981 | Masson et al. | 23/230 B |
| 4,280,816 | 7/1981 | Elahi | 23/230 B |
| 4,281,061 | 7/1981 | Zuk et al. | 435/7 |
| 4,288,228 | 9/1981 | Oberhardt | 436/178 |
| 4,298,345 | 11/1981 | Sodickson et al. | 23/230 R |
| 4,298,685 | 11/1981 | Parikh et al. | 435/7 |
| 4,299,916 | 11/1981 | Litman et al. | 435/6 |
| 4,301,139 | 11/1981 | Feingers et al. | 424/1 |
| 4,305,720 | 12/1981 | Bernstein | 23/230 B |
| 4,305,721 | 12/1981 | Bernstein | 23/230 B |
| 4,305,924 | 12/1981 | Piasio et al. | 424/1 |
| 4,313,734 | 2/1982 | Leuvering | 23/230 B |
| 4,315,907 | 2/1982 | Fridlender et al. | 424/1 |
| 4,318,707 | 3/1982 | Litman et al. | 23/230 B |
| 4,323,536 | 4/1982 | Columbus | 422/56 |
| 4,332,783 | 6/1982 | Pernice et al. | 424/1 |
| 4,333,733 | 6/1982 | Sanford et al. | 436/88 |
| 4,337,065 | 6/1982 | Hiratsuka et al. | 23/230 B |
| 4,338,094 | 7/1982 | Elahi | 23/230 B |
| 4,347,312 | 8/1982 | Brown et al. | 435/7.93 |
| 4,357,311 | 11/1982 | Schutt | 424/12 |
| 4,361,537 | 11/1982 | Deutsch et al. | 422/56 |
| 4,362,697 | 12/1982 | Tabb et al. | 422/56 |
| 4,363,874 | 12/1982 | Greenquist | 435/7.7 |
| 4,365,970 | 12/1982 | Lawrence et al. | 436/66 |
| 4,366,241 | 12/1982 | Tom et al. | 435/7 |
| 4,373,932 | 2/1983 | Gribnau et al. | 436/501 |
| 4,374,925 | 2/1983 | Litmaan et al. | 435/7 |
| 4,376,110 | 3/1983 | David et al. | 436/513 |
| 4,390,343 | 6/1983 | Walter | 435/7.72 |
| 4,391,904 | 7/1983 | Litman et al. | 435/7 |
| 4,407,943 | 10/1983 | Cole et al. | 435/7 |
| 4,425,438 | 1/1984 | Bauman et al. | 436/527 |
| 4,426,451 | 1/1984 | Columbus | 436/518 |
| 4,427,769 | 1/1984 | Adlercreutz et al. | 435/7 |

| | | | | | | | |
|---|---|---|---|---|---|---|---|
| 4,435,504 | 3/1984 | Zuk et al. | 435/7 | 4,790,979 | 12/1988 | Terminiello et al. | 422/56 |
| 4,440,301 | 4/1984 | Intengan | 206/456 | 4,797,260 | 1/1989 | Parker | 422/101 |
| 4,442,204 | 4/1984 | Greenquist et al. | 435/7 | 4,803,048 | 2/1989 | Nason | 422/58 |
| 4,444,193 | 4/1984 | Fogt et al. | 128/632 | 4,803,154 | 2/1989 | Uo et al. | 435/7 |
| 4,446,232 | 5/1984 | Liotta | 435/7 | 4,803,170 | 2/1989 | Stanton et al. | 436/518 |
| 4,446,234 | 5/1984 | Russo et al. | 435/29 | 4,806,311 | 2/1989 | Greenquist | 422/56 |
| 4,447,526 | 5/1984 | Rupchock et al. | 435/7 | 4,806,312 | 2/1989 | Greenquist | 422/56 |
| 4,447,529 | 5/1984 | Greenquist et al. | 435/7 | 4,810,470 | 3/1989 | Burkhardt et al. | 422/56 |
| 4,447,546 | 5/1984 | Hirschfeld | 436/527 | 4,812,293 | 3/1989 | McLaurin et al. | 422/69 |
| 4,450,231 | 5/1984 | Ozkan | 435/7 | 4,814,142 | 3/1989 | Gleisner | 422/56 |
| 4,452,901 | 6/1984 | Gordon et al. | 436/506 | 4,816,224 | 3/1989 | Vogel et al. | 422/55 |
| 4,459,358 | 7/1984 | Berke | 436/170 | 4,818,677 | 4/1989 | Kaufman et al. | 435/4 |
| 4,461,829 | 7/1984 | Greenquist | 435/7 | 4,826,759 | 5/1989 | Guire et al. | 435/4 |
| 4,464,552 | 8/1984 | Pawlowski | 206/56 | 4,837,145 | 6/1989 | Liotta | 435/7 |
| 4,472,498 | 9/1984 | Masuda et al. | 435/7 | 4,837,168 | 6/1989 | Jaeger et al. | 436/533 |
| 4,474,878 | 10/1984 | Halbert et al. | 435/7 | 4,837,373 | 6/1989 | Gunkel et al. | 422/56 |
| 4,477,575 | 10/1984 | Vogel et al. | 436/170 | 4,837,395 | 6/1989 | Leeder et al. | 435/7.8 |
| 4,486,530 | 12/1984 | David et al. | 435/7 | 4,843,000 | 6/1989 | Litman et al. | 435/7.91 |
| 4,504,585 | 3/1985 | Reynolds | 436/518 | 4,847,199 | 7/1989 | Snyder et al. | 435/7.34 |
| 4,506,009 | 3/1985 | Lenhoff et al. | 435/7 | 4,849,338 | 7/1989 | Litman et al. | 435/7.91 |
| 4,514,507 | 4/1985 | Secher | 436/518 | 4,849,340 | 7/1989 | Oberhardt | 435/13 |
| 4,517,288 | 5/1985 | Giegel et al. | 435/7 | 4,851,210 | 7/1989 | Hewett | 424/11 |
| 4,533,629 | 8/1985 | Litman et al. | 435/7 | 4,853,335 | 8/1989 | Olsen et al. | 436/527 |
| 4,540,659 | 9/1985 | Litman et al. | 435/7 | 4,855,240 | 8/1989 | Rosenstein et al. | 436/514 |
| 4,550,075 | 10/1985 | Bacquet et al. | 435/7 | 4,857,453 | 8/1989 | Ullman et al. | 435/7 |
| 4,552,839 | 11/1985 | Gould et al. | 435/7 | 4,859,603 | 8/1989 | Dole et al. | 435/287 |
| 4,562,148 | 12/1985 | Sommer | 435/7 | 4,859,612 | 8/1989 | Cole et al. | 436/523 |
| 4,582,811 | 4/1986 | Pucci et al. | 436/548 | 4,861,711 | 8/1989 | Friesen et al. | 436/7 |
| 4,594,327 | 6/1986 | Zuk | 436/514 | 4,868,106 | 9/1989 | Ito et al. | 435/7 |
| 4,604,365 | 8/1986 | O'Neill et al. | 436/528 | 4,868,108 | 9/1989 | Bahar et al. | 435/7 |
| 4,608,336 | 8/1986 | Benovic et al. | 435/7 | 4,870,005 | 9/1989 | Akiyoshi et al. | 435/7 |
| 4,613,567 | 9/1986 | Yasoshima et al. | 435/7 | 4,874,692 | 10/1989 | Eikenberry | 435/7.92 |
| 4,615,983 | 10/1986 | Koyama | 436/514 | 4,876,067 | 10/1989 | Deneke et al. | 422/56 |
| 4,623,461 | 11/1986 | Hossom et al. | 210/445 | 4,877,586 | 10/1989 | Devaney et al. | 422/101 |
| 4,629,690 | 12/1986 | Weng et al. | 435/7 | 4,879,215 | 11/1989 | Weng et al. | 435/7 |
| 4,631,174 | 12/1986 | Kondo | 422/56 | 4,880,751 | 11/1989 | Georghegan et al. | 436/518 |
| 4,632,901 | 12/1986 | Valkirs et al. | 435/5 | 4,883,764 | 11/1989 | Kloepfer | 436/63 |
| 4,639,419 | 1/1987 | Olson et al. | 435/5 | 4,889,816 | 12/1989 | Davis et al. | 436/518 |
| 4,642,285 | 2/1987 | Halbert et al. | 435/7.94 | 4,891,321 | 1/1990 | Hubscher | 435/293 |
| 4,663,278 | 5/1987 | DiNello | 435/7 | 4,900,663 | 2/1990 | Wie et al. | 435/7 |
| 4,668,619 | 5/1987 | Greenquist et al. | 435/7 | 4,902,629 | 2/1990 | Meserol et al. | 436/165 |
| 4,678,757 | 7/1987 | Rapkin et al. | 436/169 | 4,912,034 | 3/1990 | Kalra et al. | 435/7 |
| 4,681,732 | 7/1987 | Ozkan | 428/36 | 4,916,056 | 4/1990 | Brown, III et al. | 435/7 |
| 4,683,197 | 7/1987 | Gallati | 435/7 | 4,916,078 | 4/1990 | Klose et al. | 436/165 |
| 4,687,732 | 8/1987 | Ward et al. | 435/6 | 4,918,025 | 4/1990 | Grenner et al. | 436/165 |
| 4,687,735 | 8/1987 | DiNello et al. | 435/7 | 4,920,045 | 4/1990 | Okuda et al. | 435/7 |
| 4,690,907 | 9/1987 | Hibino et al. | 436/514 | 4,920,046 | 4/1990 | McFarland et al. | 435/7 |
| 4,693,834 | 9/1987 | Hossom | 210/767 | 4,923,680 | 5/1990 | Nelson | 422/58 |
| 4,703,017 | 10/1987 | Campbell et al. | 436/501 | 4,931,385 | 6/1990 | Block et al. | 435/7 |
| 4,711,955 | 12/1987 | Ward et al. | 536/29 | 4,933,092 | 6/1990 | Aunet et al. | |
| 4,717,656 | 1/1988 | Swanljung | 422/56 | 4,938,927 | 7/1990 | Kelton et al. | 422/64 |
| 4,722,906 | 2/1988 | Guire | 436/501 | 4,939,098 | 7/1990 | Suzuki et al. | 436/514 |
| 4,727,019 | 2/1988 | Valkirs et al. | 435/5 | 4,943,522 | 7/1990 | Eisinger et al. | 435/7 |
| 4,738,823 | 4/1988 | Engelmann | 422/56 | 4,952,517 | 8/1990 | Bahar | 436/518 |
| 4,740,468 | 4/1988 | Weng et al. | 435/7 | 4,952,520 | 8/1990 | Okusa et al. | 436/533 |
| 4,742,011 | 5/1988 | Blake et al. | 436/518 | 4,956,275 | 9/1990 | Zuk et al. | 435/7 |
| 4,743,560 | 5/1988 | Campbell et al. | 436/501 | 4,956,302 | 9/1990 | Gordon et al. | 436/161 |
| 4,752,562 | 6/1988 | Sheiman et al. | 435/5 | 4,959,197 | 9/1990 | Parekh et al. | 422/101 |
| 4,753,893 | 6/1988 | Roper | 436/509 | 4,959,305 | 9/1990 | Woodrum | 435/7 |
| 4,757,024 | 7/1988 | Roper | 436/507 | 4,959,307 | 9/1990 | Olson | 435/7 |
| 4,760,142 | 7/1988 | Primes et al. | 544/287 | 4,960,565 | 10/1990 | Shurben | 422/61 |
| 4,761,381 | 8/1988 | Blatt et al. | 436/165 | 4,960,691 | 10/1990 | Gordon et al. | 435/6 |
| 4,770,853 | 9/1988 | Bernstein | 422/58 | 4,960,692 | 10/1990 | Lentrichia et al. | 435/7 |
| 4,774,174 | 9/1988 | Giegel et al. | 435/5 | 4,963,325 | 10/1990 | Lennon et al. | 422/61 |
| 4,775,636 | 10/1988 | Moeremans et al. | 436/518 | 4,963,468 | 10/1990 | Olson | 435/7 |
| 4,776,612 | 10/1988 | Cox | 238/1 A | 4,976,926 | 12/1990 | Matkovich | 422/101 |
| 4,780,280 | 10/1988 | Berger et al. | 422/56 | 4,977,078 | 12/1990 | Niimura et al. | 435/7 |
| 4,782,016 | 11/1988 | Norton | 435/21 | 4,981,786 | 1/1991 | Dafforn et al. | 435/7.92 |
| 4,786,594 | 11/1988 | Khanna et al. | 435/7.91 | 4,988,627 | 1/1991 | Smith-Lewis | 436/165 |
| 4,788,136 | 11/1988 | Grenier et al. | 435/7 | 4,990,442 | 2/1991 | Del Campo | 435/7.5 |
| 4,789,526 | 12/1988 | Matkovich | 422/101 | 4,999,285 | 3/1991 | Stiso | 433/7.9 |
| 4,789,629 | 12/1988 | Baker et al. | 435/7.92 | 4,999,287 | 3/1991 | Allen et al. | 435/11 |

| Patent Number | Date | Inventor | Class |
|---|---|---|---|
| 5,006,464 | 4/1991 | Chu et al. | 435/7.1 |
| 5,006,474 | 4/1991 | Horstman et al. | 436/524 |
| 5,009,996 | 4/1991 | Shah et al. | 435/7 |
| 5,009,997 | 4/1991 | Shah et al. | 435/7.4 |
| 5,024,323 | 6/1991 | Bolton | 206/63.3 |
| 5,028,535 | 7/1991 | Buechler et al. | 435/7.1 |
| 5,030,555 | 7/1991 | Clemmons | 435/5 |
| 5,030,558 | 7/1991 | Litman et al. | 435/7.91 |
| 5,039,607 | 8/1991 | Skold et al. | 435/7.5 |
| 5,051,237 | 9/1991 | Grenner et al. | 422/56 |
| 5,059,526 | 10/1991 | Arai et al. | 435/17 |
| 5,064,541 | 11/1991 | Jeng et al. | |
| 5,071,746 | 12/1991 | Wilk et al. | 435/7.94 |
| 5,073,484 | 12/1991 | Swanson et al. | 435/7.92 |
| 5,075,078 | 12/1991 | Osikowicz et al. | 422/56 |
| 5,079,142 | 1/1992 | Coleman et al. | 435/7.92 |
| 5,079,172 | 1/1992 | Hari et al. | 436/518 |
| 5,079,174 | 1/1992 | Buck et al. | 436/538 |
| 5,085,987 | 2/1992 | Olson | 435/7.91 |
| 5,085,988 | 2/1992 | Olson | 435/7.91 |
| 5,087,556 | 2/1992 | Ertinghausen | 435/7.9 |
| 5,089,391 | 2/1992 | Buechler et al. | 435/7.1 |
| 5,094,962 | 3/1992 | Snyder et al. | 436/518 |
| 5,096,809 | 3/1992 | Chen et al. | 435/7.9 |
| 5,096,837 | 3/1992 | Fan et al. | 436/514 |
| 5,100,619 | 3/1992 | Baker et al. | 422/58 |
| 5,100,620 | 3/1992 | Brenneman | 422/58 |
| 5,104,793 | 4/1992 | Buck | 435/7.92 |
| 5,104,811 | 4/1992 | Berger et al. | 436/164 |
| 5,104,812 | 4/1992 | Kurn et al. | 436/165 |
| 5,106,582 | 4/1992 | Baker | 422/58 |
| 5,106,758 | 4/1992 | Adler et al. | 436/165 |
| 5,110,550 | 5/1992 | Schlipfenacher et al. | 422/56 |
| 5,114,673 | 5/1992 | Berger et al. | 422/56 |
| 5,114,862 | 5/1992 | Brenneman | 436/169 |
| 5,119,941 | 6/1992 | Lepie | 206/102 |
| 5,120,643 | 6/1992 | Ching et al. | 435/7.92 |
| 5,120,662 | 6/1992 | Chan et al. | 436/530 |
| 5,132,086 | 7/1992 | Allen et al. | 422/56 |
| 5,132,208 | 7/1992 | Freitag et al. | 435/7.1 |
| 5,135,716 | 8/1992 | Thakore | 422/56 |
| 5,135,872 | 8/1992 | Pouletty et al. | 436/180 |
| 5,135,873 | 8/1992 | Patel et al. | 436/180 |
| 5,137,804 | 8/1992 | Greene et al. | 435/5 |
| 5,137,808 | 8/1992 | Ullman et al. | 435/7.9 |
| 5,141,850 | 8/1992 | Cole et al. | 436/525 |
| 5,141,875 | 8/1992 | Kelton et al. | 436/514 |
| 5,143,210 | 9/1992 | Warwick | 206/45.1 |
| 5,145,784 | 9/1992 | Cox et al. | 436/526 |
| 5,156,952 | 10/1992 | Litman et al. | 435/7.91 |
| 5,158,869 | 10/1992 | Pouletty et al. | 435/7.9 |
| 5,158,895 | 10/1992 | Ashihara et al. | 436/526 |
| 5,160,486 | 11/1992 | Schlipfenbacher et al. | 422/56 |
| 5,162,237 | 11/1992 | Messenger et al. | 436/523 |
| 5,164,294 | 11/1992 | Skold et al. | 435/7.5 |
| 5,177,021 | 1/1993 | Kondo | 436/518 |
| 5,182,191 | 1/1993 | Fan et al. | 435/7.9 |
| 5,182,216 | 1/1993 | Clayton et al. | 436/518 |
| 5,185,127 | 2/1993 | Vonk | 422/56 |
| 5,188,939 | 2/1993 | Mangold et al. | 435/7.92 |
| 5,188,966 | 2/1993 | Eikmeier et al. | 436/170 |
| 5,202,267 | 4/1993 | Ditlow et al. | 436/525 |
| 5,202,268 | 4/1993 | Kuhn et al. | 436/525 |
| 5,206,177 | 4/1993 | DeLaCroix et al. | 436/518 |
| 5,209,904 | 5/1993 | Forney et al. | 422/73 |
| 5,211,914 | 5/1993 | Vogel et al. | 422/56 |
| 5,212,060 | 5/1993 | Maddox | |
| 5,215,886 | 6/1993 | Patel et al. | 435/11 |
| 5,223,436 | 6/1993 | Freitag et al. | 436/97 |
| 5,232,835 | 8/1993 | Litman et al. | 435/7.93 |
| 5,234,813 | 8/1993 | McGeehan et al. | 435/7.9 |
| 5,236,826 | 8/1993 | Marshall | 435/7.92 |
| 5,238,652 | 8/1993 | Sun et al. | 422/61 |
| 5,240,862 | 8/1993 | Koenhen et al. | |
| 5,248,619 | 9/1993 | Skold et al. | 436/514 |
| 5,252,492 | 10/1993 | Yoshikami | 436/501 |
| 5,256,372 | 10/1993 | Brooks et al. | 422/58 |
| 5,258,163 | 11/1993 | Krause et al. | 422/58 |
| 5,260,193 | 11/1993 | Olson | 435/7.91 |
| 5,260,194 | 11/1993 | Olson | 435/7.91 |
| 5,260,222 | 11/1993 | Patel et al. | 436/180 |
| 5,264,180 | 11/1993 | Allen et al. | 422/56 |
| 5,275,785 | 1/1994 | May et al. | 422/56 |
| 5,278,079 | 1/1994 | Gubinski et al. | 436/165 |
| 5,294,369 | 3/1994 | Shigekawa et al. | 252/313.1 |
| 5,308,580 | 5/1994 | Clark | 422/58 |
| 5,314,804 | 5/1994 | Boguslaski et al. | 435/12 |

FOREIGN PATENT DOCUMENTS

| | | |
|---|---|---|
| 0279097 | 8/1988 | European Pat. Off. |
| 0284232 | 9/1988 | European Pat. Off. |
| 0290921 | 11/1988 | European Pat. Off. |
| 0291176 | 11/1988 | European Pat. Off. |
| 0291194 | 11/1988 | European Pat. Off. |
| 0296724 | 12/1988 | European Pat. Off. |
| 0297292 | 1/1989 | European Pat. Off. |
| 0299428 | 1/1989 | European Pat. Off. |
| 0306772 | 3/1989 | European Pat. Off. |
| 0 310 406 | 4/1989 | European Pat. Off. |
| 0317001 | 5/1989 | European Pat. Off. |
| 0 319 294 | 6/1989 | European Pat. Off. |
| 0322340 | 6/1989 | European Pat. Off. |
| 0323605 | 7/1989 | European Pat. Off. |
| 0342771 | 11/1989 | European Pat. Off. |
| 0374684 | 6/1990 | European Pat. Off. |
| 0383619 | 8/1990 | European Pat. Off. |
| 0415679 | 3/1991 | European Pat. Off. |
| 0443231 | 8/1991 | European Pat. Off. |
| 0516095 | 12/1992 | European Pat. Off. |
| 2016687 | 9/1979 | United Kingdom |
| 2204398 | 11/1988 | United Kingdom |
| 8402193 | 6/1984 | WIPO |
| WO86/03839 | 7/1986 | WIPO |
| WO86/04683 | 8/1986 | WIPO |
| WO87/02774 | 5/1987 | WIPO |
| WO87/02778 | 5/1987 | WIPO |
| WO805540 | 7/1988 | WIPO |
| 8903992 | 5/1989 | WIPO |
| WO906801 | 7/1989 | WIPO |
| WO90/5906 | 5/1990 | WIPO |
| WO91/01003 | 1/1991 | WIPO |
| WO119980 | 12/1991 | WIPO |
| WO201226 | 1/1992 | WIPO |
| WO93/03176 | 2/1993 | WIPO |

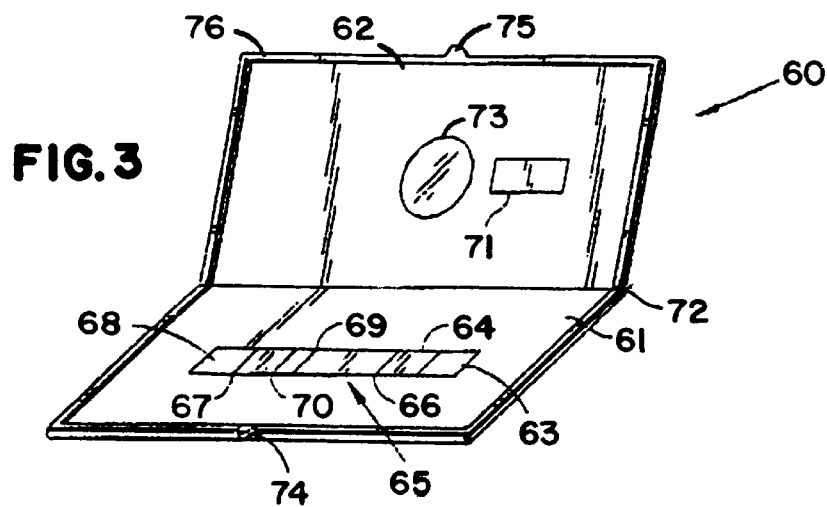
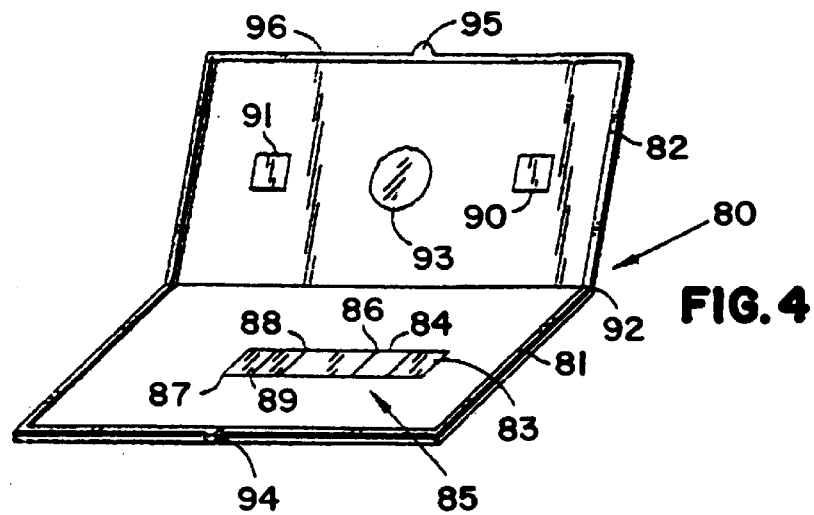
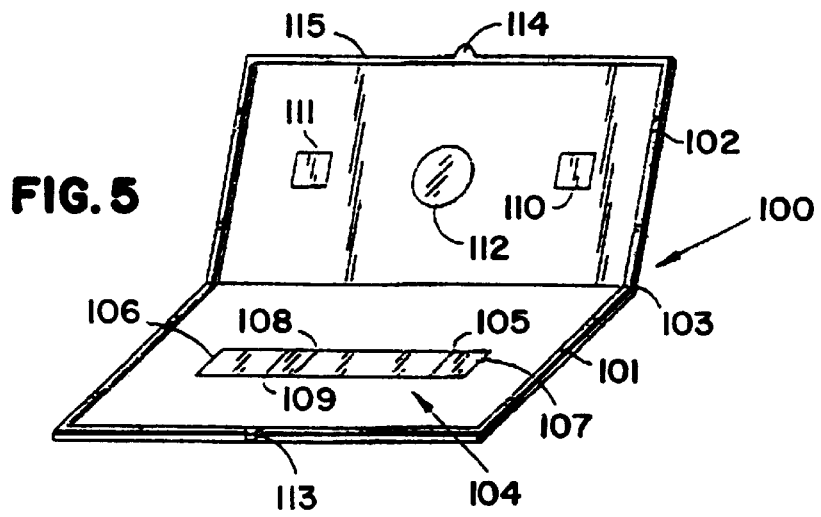

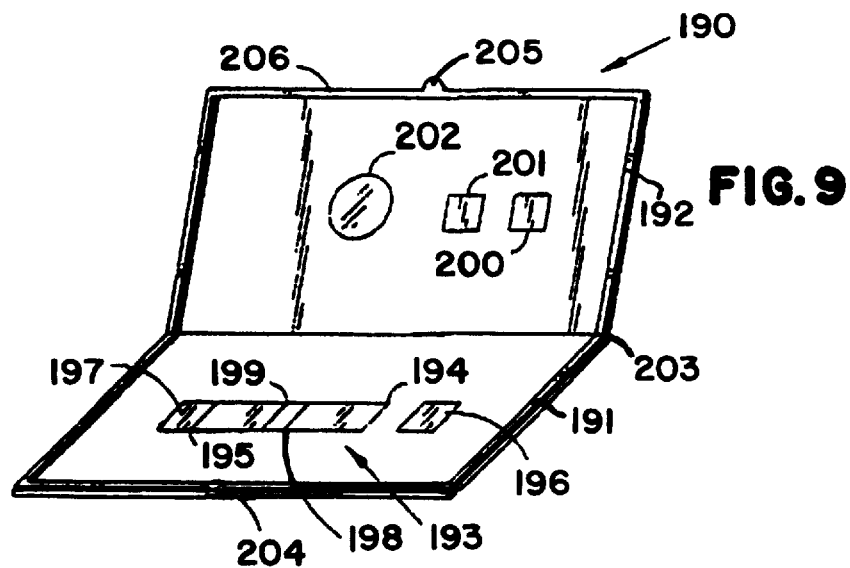
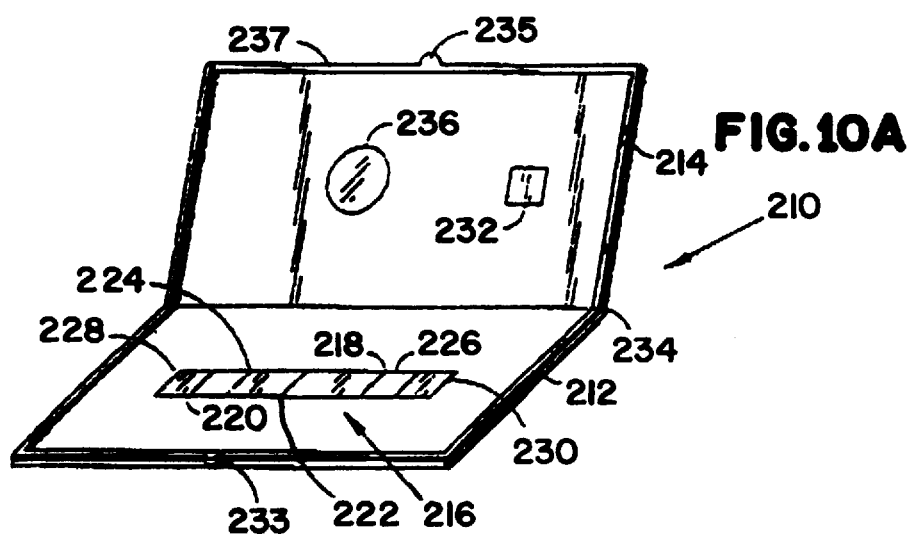

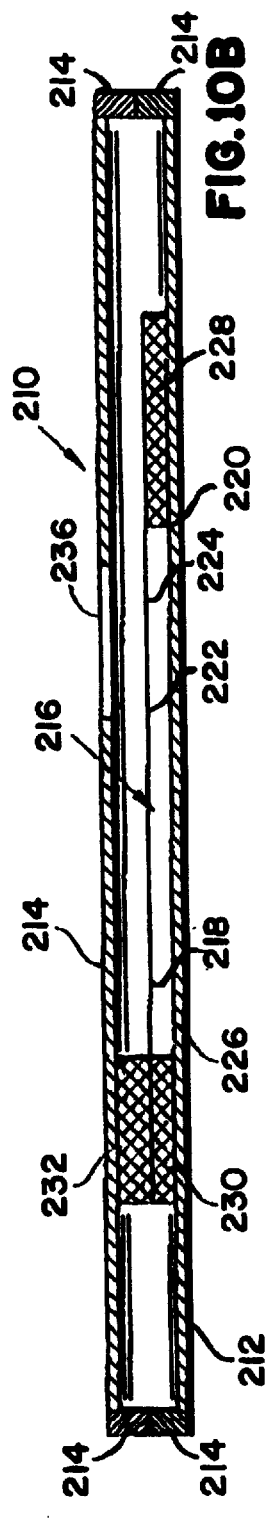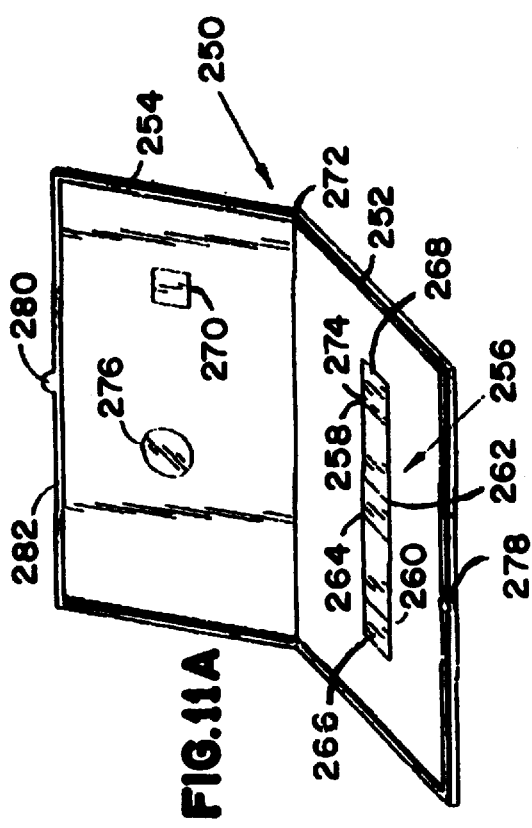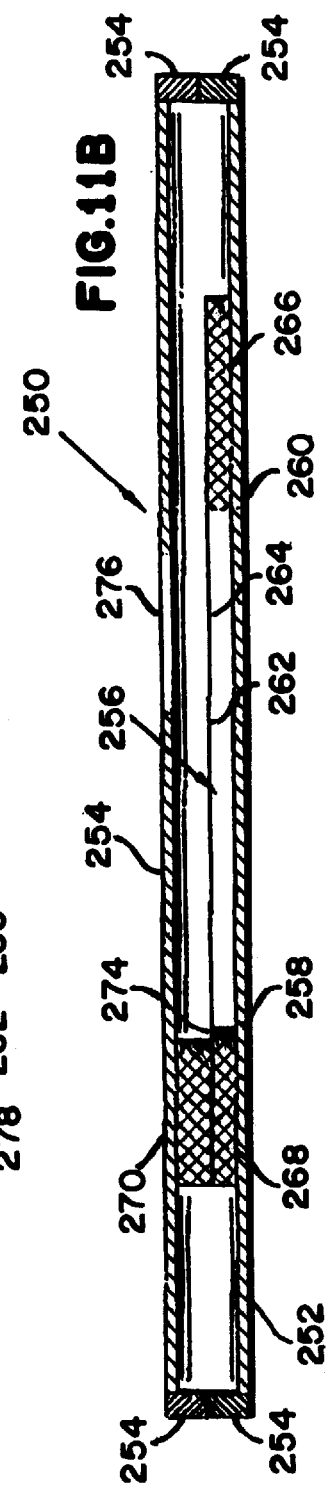

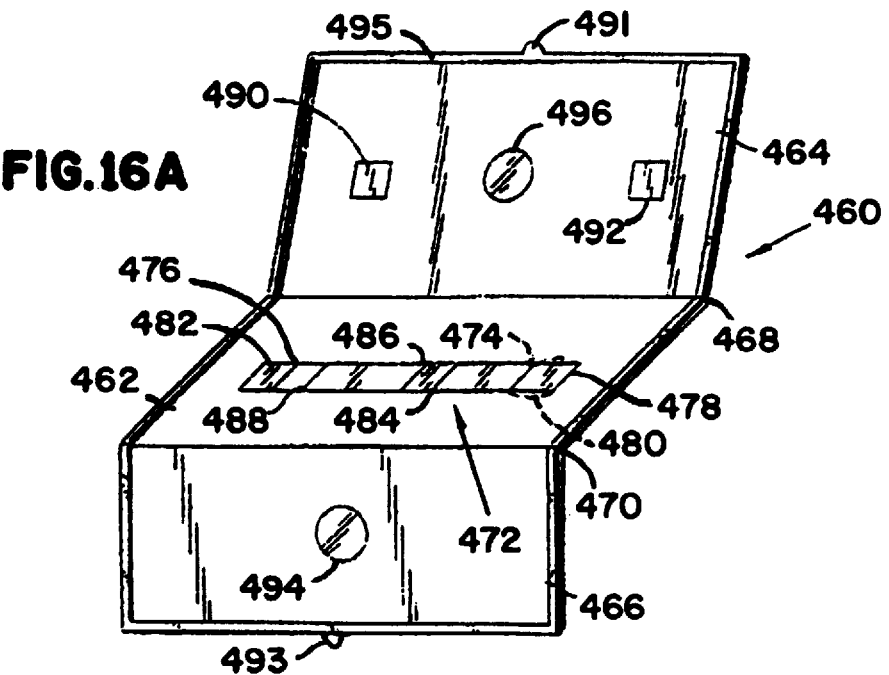
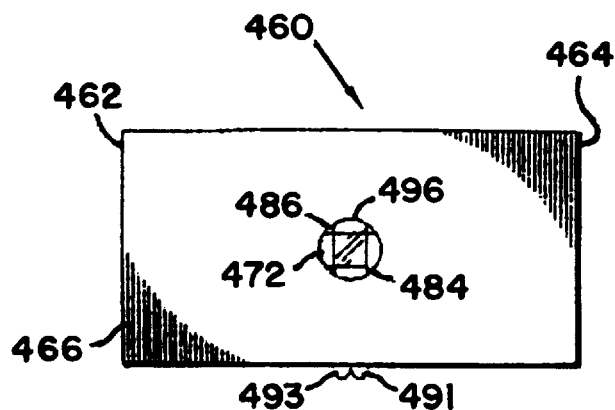

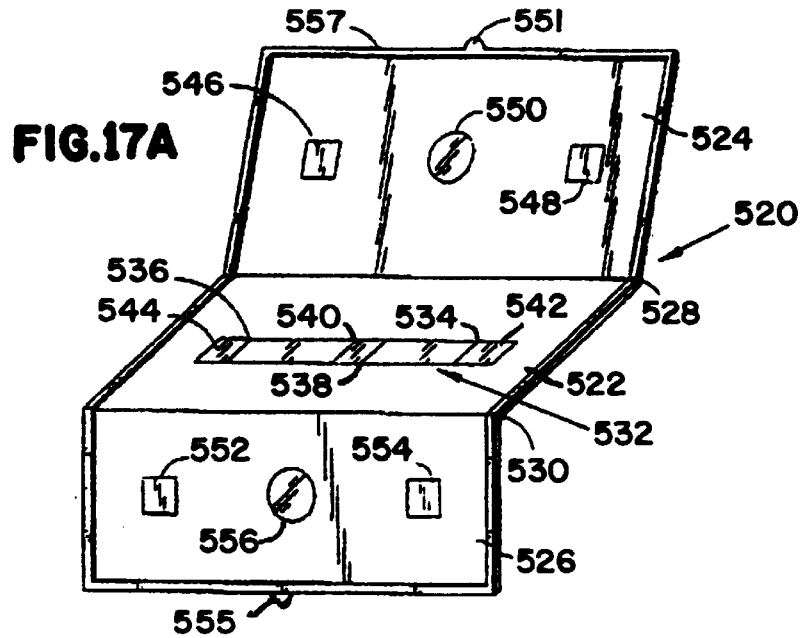
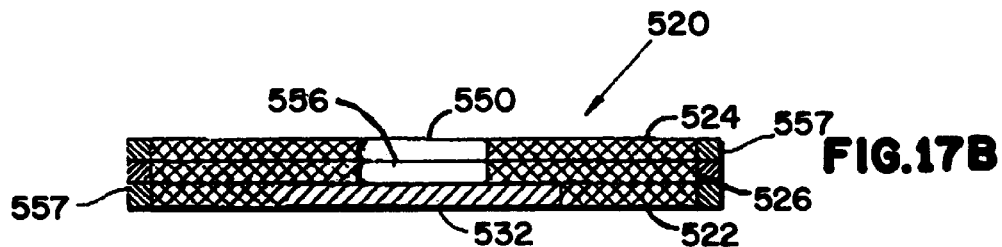
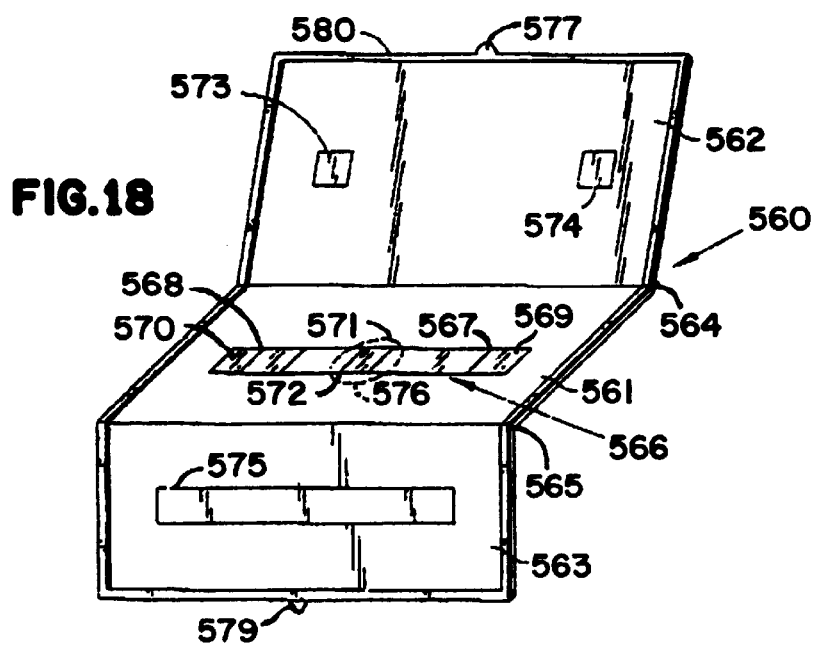

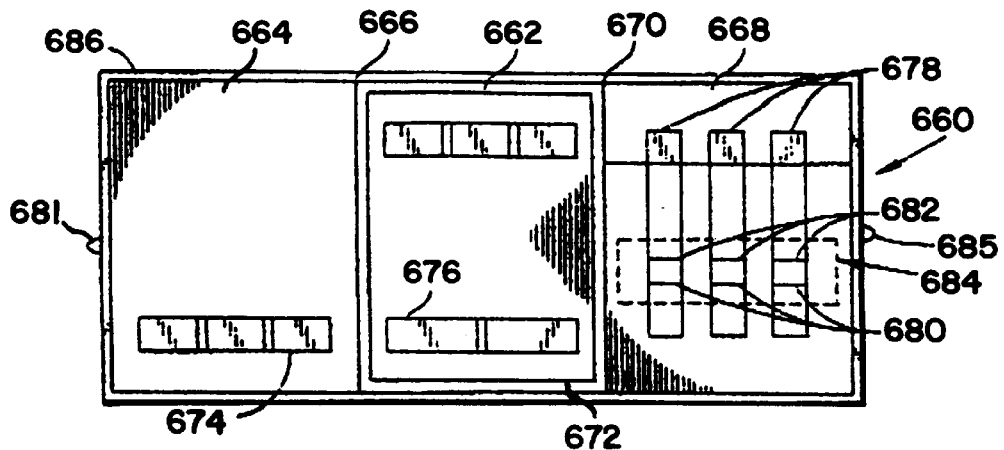
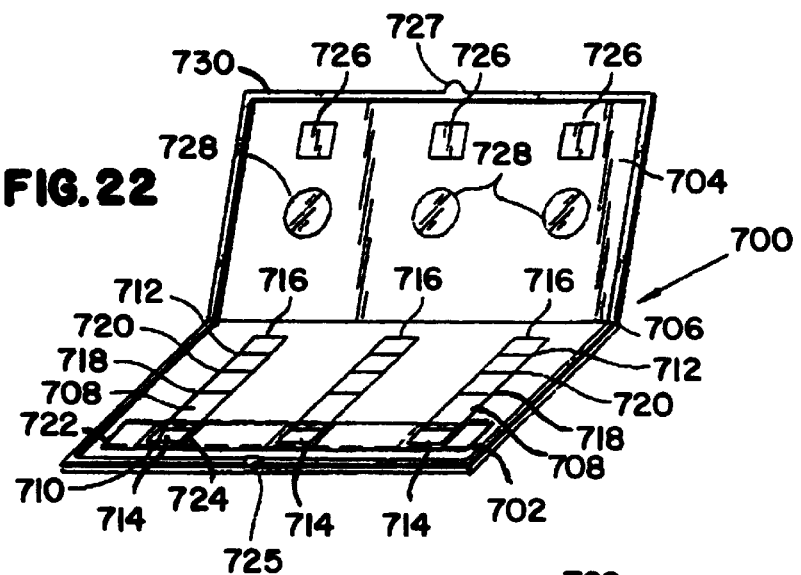

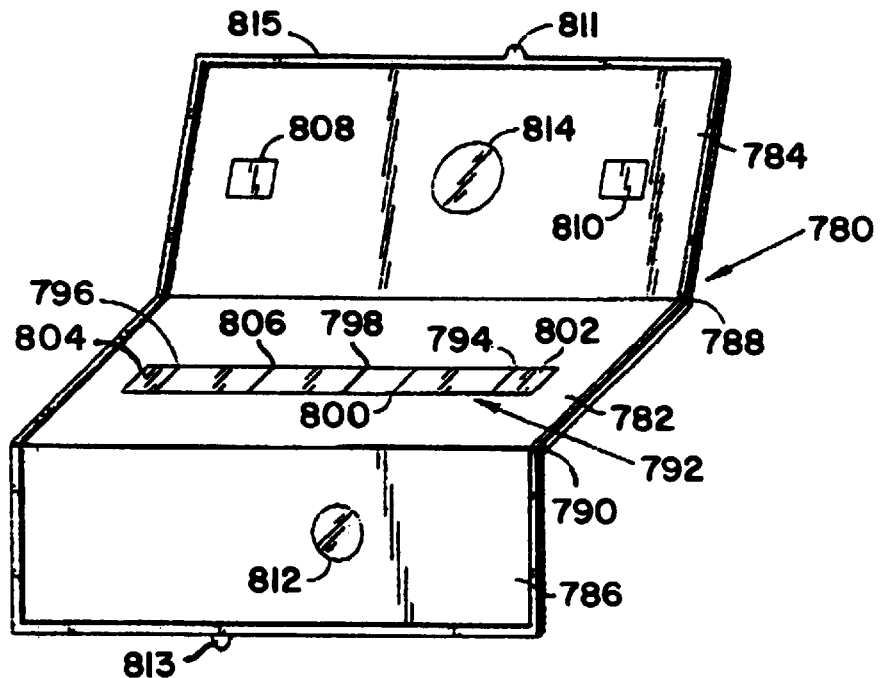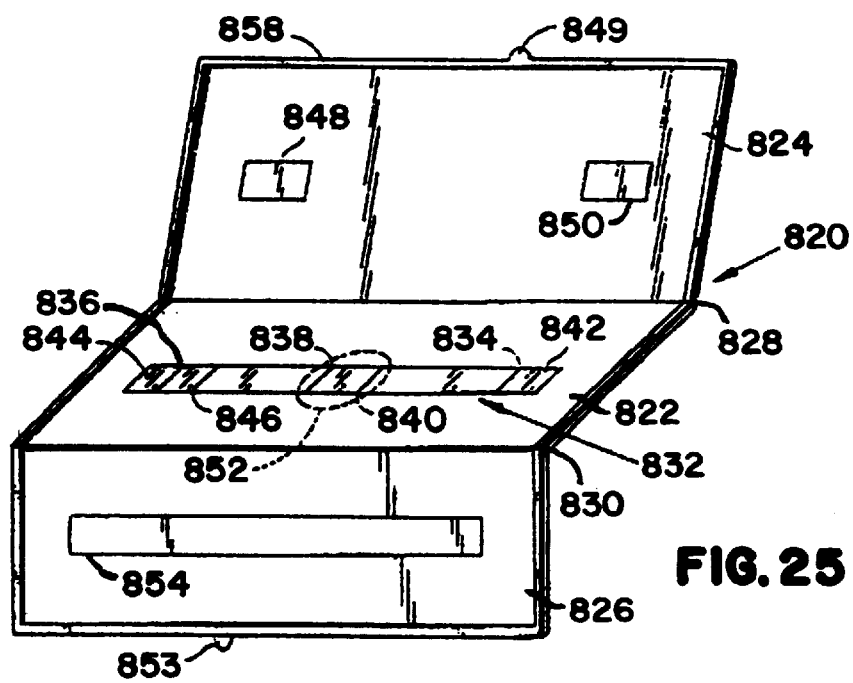

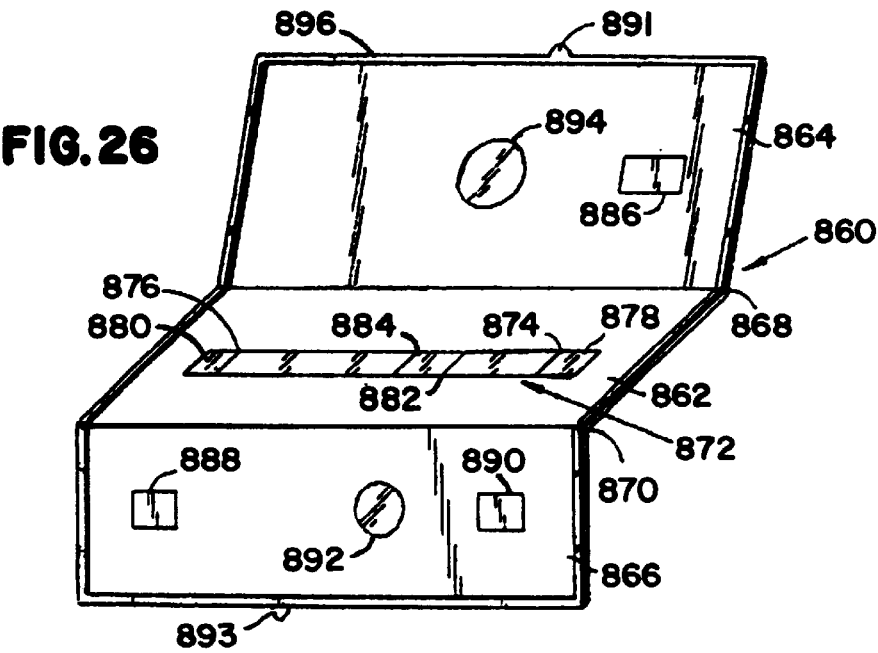
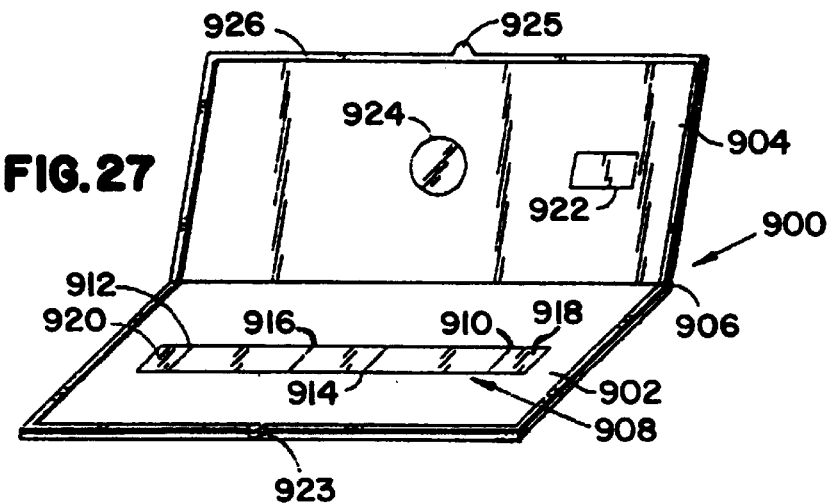
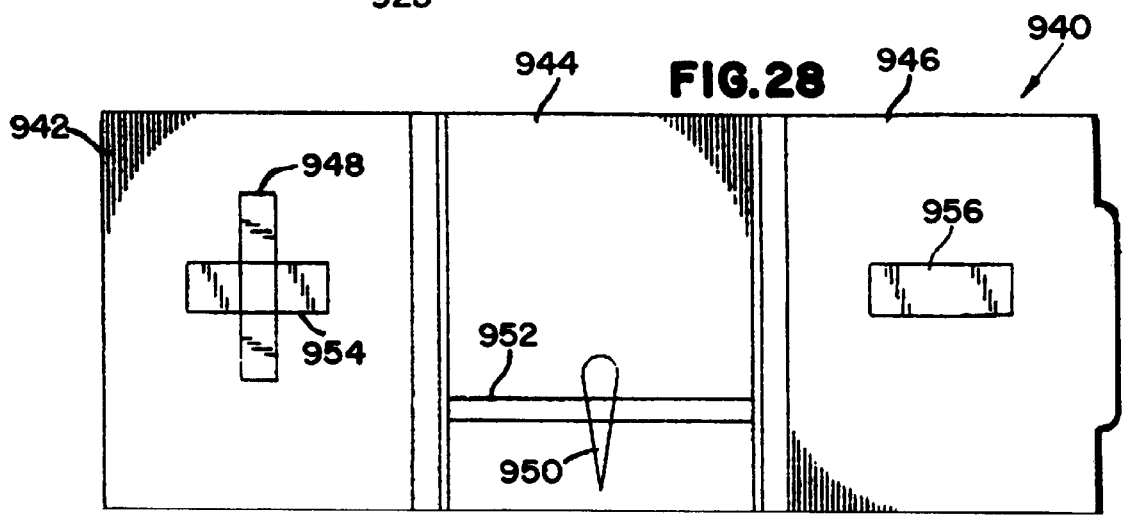

ced May 27, 1992, now abandoned and also entitled "Assay Device," which was in turn a continuation-in-part of U.S. application Ser. No. 07/706,639 by Howard M. Chandler, filed May 29, 1991, entitled "Assay Device." Both of these preceding applications are incorporated herein in their entirety by this reference.

IMMUNOCHROMATOGRAPHIC ASSAY DEVICE

CROSS-REFERENCES

This application is a continuation-in-part of U.S. application Ser. No. 07/888,831, by Howard M. Chandler, filed May 27, 1992, now abandoned and also entitled "Assay Device," which was in turn a continuation-in-part of U.S. application Ser. No. 07/706,639 by Howard M. Chandler, filed May 29, 1991, entitled "Assay Device." Both of these preceding applications are incorporated herein in their entirety by this reference.

BACKGROUND OF THE INVENTION

This invention is directed to test strips for determination of characteristics of samples, unitized housings, and kits incorporating the test strips and housings, and methods of determining the characteristics of samples using the test strips and housings.

Among the many analytical systems used for detection and/or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibody to the bacterium *Helicobacter pylori* and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers and anticonvulsants, and illegal drugs of abuse, such as cocaine, heroin, and marijuana;

(7) environmental pollutants such as pesticides and aromatic hydrocarbons and (8) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" systems in which a solvent moves across a thin, flat absorbent medium.

Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., *Am. J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. The antigen to be detected can itself be an antibody, such as in serological assays for *H. pylori*-specific antibody. In such cases, the antibody to be detected can be bound to a specific antigen. Alternatively, the antigen to be detected can be detected indirectly by using a labeled second antibody that binds to the first antibody to the analyte to be detected.

In general, the sandwich immunochromatographic procedures call for mixing the sample that may contain the analyte to be assayed with antibodies to the analyte. These antibodies are mobile and typically are linked to a label or a disclosing reagent, such as dyed latex, a colloidal metal sol, or a radioisotope. This mixture is then applied to a chromatographic medium containing a band or zone of immobilized antibodies to the analyte of interest. The chromatographic medium often is in the form of a strip resembling a dipstick. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al. both of which are incorporated herein by this reference.

In competitive immunoassays, the label is typically a labeled analyte or analyte analogue which competes for binding of an antibody with any unlabeled analyte present in the sample. Competitive immunoassays are typically used for detection of analytes such as haptens, each hapten being monovalent and capable of binding only one antibody molecule. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all of which are incorporated herein by this reference.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to insure that the sample reaches the area where binding is to occur in a uniform, straight-line manner.

Other problems exist with currently-available test strips because of the nature of the sample to be assayed or the assay to be carried out. With such devices, it is impractical to perform washing steps which are frequently desirable to improve sensitivity and to reduce background. Also, it is difficult, and in many cases impossible, to carry out preincubation steps within the device.

Additionally, there is a need for an immunochromatographic assay device that can carry out a broad range of separations, such as the separation of fat from milk or the separation of organic chemicals such as the separation of benzene from toluene.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes, or microfuge tubes, requiring the use of transfer devices, such as pipettes. Each of these devices is then contaminated and must be disposed of using special precautions so that workers or people who may inadvertently come into contact with the waste do not become contaminated.

Still another limitation on chromatographic devices currently available for use by the clinician or technician is their inability to perform two-directional or two-dimensional chromatography. These techniques have long been known to be powerful analytical tools, but their complexity relative to simple unidirectional chromatography has made it difficult to apply them to test strip devices in the physician's office or a clinical laboratory.

Accordingly, there is a need for an improved assay device capable of handling a broad range of chromatographic assays. Such a device should be able to handle all types of immunoassays, including both sandwich and competitive immunoassays as well as other types of assays using chromatography. Such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the tests. Additionally, such an improved test strip should be capable of performing two-directional or two-dimensional chromatography when used in clinical laboratories or physicians' offices.

SUMMARY

We have developed an assay device that meets these needs and provides improved assays for analytes of biological interest, while simplifying the performance of the assay and avoiding contamination. The device can perform all types of immunoassays, including sandwich immunoassays, competitive immunoassays, and assays employing combinations of these principles. The device can perform serological assays in which the antigen to be detected is itself an antibody, such as antibody to *H. pylori*. The device can perform assays in which the antigen to be detected is detected indirectly by using a labeled second antibody binding to the first antibody to the analyte.

An assay device according to the present invention makes use of pressure to transfer fluid from one opposable component to another opposable component, and also to drive fluid through the chromatographic medium. The pressure not only speeds up the operation of the device, but allows the performance of additional steps such as extraction steps to remove interfering particulate components within a single device. The pressure is generated by holding the opposable components together with engagers such as interlocking elements on each of the opposable components. Preferably, a predetermined pressure is applied to ensure the optimum performance of each step of the assay procedure.

Additionally, the device can perform other types of specific binding assays, such as: (1) assays based on the affinity of specific binding proteins such as lectins, hormone receptors, or viral receptors for their specific ligands; (2) assays based on the affinity of enzymes for their corresponding substrates or inhibitors; or (3) assays based on the affinity of a nucleic acid (DNA or RNA) segment for a complementary nucleic acid segment according to the Watson-Crick base pairing scheme.

The device comprises:
(1) at least two substantially planar opposable components, wherein one of the substantially planar components has on its surface a chromatographic medium; and
(2) means for opposing the opposable components and applying pressure thereto, the pressure being sufficient to transfer fluid from one opposable component to another opposable component in a direction substantially normal to the opposable component so that the sample is applied to the chromatographic medium for detection and/or determination of the analyte thereon.

Devices according to the present invention can also comprise:
(1) at least three substantially planar opposable components, wherein one of the substantially planar components has on its surface a chromatographic medium, the chromatographic medium having first and second ends;
(2) means for opposing the opposable components pairwise in at least two different combinations and applying pressure thereto, the pressure being sufficient to transfer fluid from one opposable component to another in a direction substantially normal to the opposable components so that the sample is applied to the chromatographic medium and flows through the chromatographic medium from the first end to the second end for detection and/or determination of the analyte on the chromatographic medium; and
(3) at least one applicator and one absorber located on one of the opposable components and positioned in such manner that, when the opposable component on which the applicator and the absorber is located is brought into opposition to the opposable component on which the chromatographic medium is located, a second liquid is applied to the chromatographic medium and flows through the chromatographic medium from the second end to the first end, thereby reversing the flow through the chromatographic medium, with the detection and/or determination of the analyte being made subsequent to reversal of the flow through the chromatographic medium.

In one aspect, a chromatographic assay device according to the present invention comprises:

(1) a first opposable component including a sample preparation zone adapted to receive a sample to be assayed; and (2) a second opposable component including a chromatographic medium.

An embodiment of the chromatographic assay device suitable for sandwich immunoassays comprises:

(1) a first opposable component including:
   (a) a chromatographic medium having first and second ends;
   (b) a detector application pad in operable contact with the first end of the chromatographic medium;
   (c) a conductor in operable contact with the detector application pad and in indirect contact with the first end of the chromatographic medium; and
   (d) an absorber in operable contact with the second end of the chromatographic medium; and (2) a second opposable component including a sample preparation zone for receiving a sample to be tested.

In this device, the first and second opposable components are configured so that bringing the first and second opposable components into opposition results in the sample preparation zone being in contact with the conductor to apply the sample to be tested to the conductor and then to the first end of the chromatographic medium through the detector application pad.

Typically, the sample preparation zone contains at least one reagent for treatment of the sample. In some cases, such as when a urine or serum sample is assayed, no extraction or other treatment of the sample is required. Also typically, the detector application pad contains a first specific binding partner to the analyte in a form that can be resolubilized by addition of an aqueous liquid to the detector application pad, the first specific binding partner being labeled with a detectable label, and the chromatographic medium further comprises a detection zone substantially smaller in area than the area of the chromatographic medium. In this arrangement, the detection zone contains a specific binding partner to the analyte immobilized thereto, such that a ternary complex comprising the first specific binding partner, the analyte, and the second specific binding partner forms at the detection zone if analyte is present in the sample.

Preferably, the detectable label is a visually detectable label.

Preferably, the first and second opposable components are joined by a hinge. Typically, the hinge is impermeable to an aqueous liquid. The opposable elements preferably also include perimeter upstanding walls which engage in abutting relationship when the device is closed and locked.

A test kit can comprise, in separate containers, the chromatographic assay device described above and a specific binding partner for the analyte labeled with a detectable label to be applied to the detector application pad. Alternatively, if the detector application pad contains a resolubilizable labeled first specific binding partner, the kit can comprise the assay device and an aqueous liquid for resolubilizing the labeled specific binding partner. Similar test kits can be constructed for other embodiments of an assay device according to the present invention.

A method for detecting and/or determining an analyte in a sample using this assay device to perform a sandwich immunoassay can comprise the steps of:

(1) applying the aqueous sample to the sample application pad of the chromatographic assay device containing a resolubilizable labeled first specific binding partner on the detector application pad;

(2) bringing the first and second opposable components of the chromatographic assay device into opposition, such that the sample comprises an aqueous liquid resolubilizing the labeled specific binding partner in the detector application pad, and such that the sample and the resolubilized labeled specific binding partner are applied to the conductor;

(3) allowing the sample and labeled specific binding partner to move through the conductor and then through at least a portion of the chromatographic medium so that the labeled specific binding partner gives a detectable indication of the presence and/or quantity of the analyte in the test sample; and (4) observing and/or measuring the labeled specific binding partner in at least a portion of the chromatographic medium in order to detect and/or determine the analyte.

In another version of this embodiment, the second opposable component can also contain a second detector application pad in operable contact with the sample preparation zone. In this version, the second detector application pad contains a second labeled specific binding partner for the analyte in a form that can be resolubilized by the addition of a sample to the sample preparation zone; the second labeled specific binding partner is labeled with a detectable label. The second labeled specific binding partner is positioned such that application of the sample to the sample preparation zone resolubilizes the second labeled specific binding partner so that the sample preparation zone contains a mixture of the sample and the second labeled specific binding partner. The first and second labeled specific binding partners are preferably identical and are labeled with an identical label.

Another embodiment of an assay device according to the present invention comprises:

(1) a first opposable component including:
   (a) a chromatographic medium having first and second ends; and
   (b) a conductor in operable contact with the first end of the chromatographic medium; and (2) a second opposable component including:
   (a) a sample preparation zone for receiving a sample to be assayed; and
   (b) an absorber separated from the sample preparation zone.

In this device, the first and second opposable components are configured so that bringing the first and second opposable components into opposition results in the sample preparation zone coming into operable contact with the conductor to apply the sample to be tested to the conductor and then to the first end of the chromatographic medium, and results in the absorber coming into operable contact with the second end of the chromatographic medium to withdraw fluid from the second end of the chromatographic medium. Moving the absorber to the second opposable component allows the use of a larger absorber, which can be advantageous if it is desired to assay a sample of relatively large volume.

Another version of an assay device according to the present invention with an absorber on the second opposable component has a sample preparation zone on the first opposable component, a chromatographic medium, and a conductor in operable contact with the sample preparation zone and the first end of the chromatographic medium so that the conductor bridges the sample preparation zone and the chromatographic medium. The second opposable component has an applicator containing a specific binding partner for an analyte in a form that can be resolubilized by the addition of an aqueous liquid to the applicator and an absorber separated from the applicator. The specific binding partner contained in the applicator is labeled with a detectable label. In this device, bringing the first and second opposable components into opposition results in the applicator coming into operable contact with the sample preparation zone such that, when a sample has been added to the sample preparation zone, the labeled specific binding partner for the analyte is resolubilized, and results in the absorber coming into operable contact with the second end of the chromatographic medium to withdraw fluid from the chromatographic medium.

In yet another version of an assay device according to the present invention with an absorber on the second component, the first opposable component includes a chromatographic medium and a conductor. The second opposable component includes a first applicator, a second applicator, and an absorber. The absorber is separated from both the first applicator and the second applicator. The first and second applicator are positioned on the second opposable component such that they are not in operable contact when the first and second opposable components are not in opposition. The absorber is positioned such that it is in operable contact with the second end of the chromatographic medium when the first and second opposable components are brought into opposition. The first and second opposable components are configured so that bringing the first and second opposable components into opposition results in the conductor coming in operable contact with the first applicator and results in the conductor coming in operable contact with the second applicator, thereby resulting in the first and second applicator coming into operable contact with each other.

In this device, the second applicator can include a detector application pad containing a labeled first specific binding partner in resolubilizable form.

A method of use of this device according to the present invention comprises applying the sample to the first applicator, and bringing the first and second opposable components into opposition so that the sample resolubilizes the labeled specific binding partner in the detector application pad. The chromatography and detection steps are as described above.

Yet another assay device according to the present invention including an absorber on the second component comprises:

(1) a first opposable component including:
    (a) a chromatographic medium having first and second ends;
    (b) a conductor in operable contact with the first end of the chromatographic medium; and
    (c) a detector application pad in direct contact with the conductor and positioned such that it is in indirect contact with the first end of the chromatographic medium; and
(2) a second opposable component including:
    (a) a sample application pad; and
    (b) an absorber separated from the sample application pad.

In this device, the first and second opposable components are configured so that bringing the first and second opposable components into opposition results in:

(1) the sample application pad applying the sample to the detector application pad and thus to the first end of the chromatographic medium through the conductor; and (2) the absorber being in operable contact with the second end of the chromatographic medium.

A detection method employing this version of the assay device is similar to those described above.

Yet another version of an assay device according to the present invention incorporating an absorber on the second opposable component comprises:

(1) a first opposable component including:
    (a) a chromatographic medium having first and second ends; and
    (b) a detector application pad in direct contact with the first end of the chromatographic medium; and
(2) a second opposable component including:
    (a) a sample application pad; and
    (b) an absorber separated from the sample application pad.

In this device, the first and second opposable components are configured that bringing the first and second opposable components into opposition causes the detector application pad and the sample application pad to come in contact except for the region of the detector application pad directly adjacent to the first end of the chromatographic medium. Bringing the first and second opposable components of this device into opposition causes:

(1) the sample to be tested to be applied to the detector application pad and then to the first end of the chromatographic medium; and (2) the absorber to be brought into operable contact with the second end of the chromatographic medium.

Yet another assay device according to the present invention including an absorber on the second opposable component comprises:

(1) a first opposable component including:
    (a) a chromatographic medium having first and second ends; and
    (b) a conductor positioned such that it is not in operable contact with the first end of the chromatographic medium when the first opposable component and the second opposable component are not in opposition; and
(2) a second opposable component including:
    (i) a first applicator;
    (ii) a second applicator; and
    (iii) an absorber separated from the first and second applicators, the first and second applicators being positioned on the second opposable component such that they are not in operable contact when the first and second opposable components are not in opposition.

In this device, the first and second opposable components are configured so that bringing the first and second opposable components into opposition:

(1) results in the conductor coming in operable contact with the first applicator, results in the conductor coming in operable contact with the second applicator, and results in the second applicator coming in operable contact with the first end of the chromatographic medium, thereby placing the first and second applicator in operable contact with each other to apply the contents of the first and second applicator of the chromatographic medium; and (2) results in the absorber coming in operable contact with the second end of the chromatographic medium.

Another embodiment of an assay device according to the present invention suitable for the performance of a sandwich immunoassay allows for the washing of the chromatographic medium by a portion of the sample to remove unbound labeled specific binding partner and reduce the background. This embodiment comprises:

(1) a first opposable component including:
   (a) a chromatographic medium having first and second ends;
   (b) a conductor in operable contact with the first end of the chromatographic medium; and
   (c) an absorber in operable contact with the second end of the chromatographic medium; and
(2) a second opposable component including an applicator divided into two sectors:
   (a) a first sector containing a first specific binding partner for the analyte in a form that can be resolubilized by addition of an aqueous liquid to the applicator, the first specific binding partner being labeled with a detectable label; and
   (b) a second sector without the labeled specific binding partner.

In this device, the first and second opposable components are configured so that bringing the first and second opposable components into opposition places the first sector, but not the second sector, of the applicator into direct contact with the conductor, the second sector being in indirect contact with the conductor, to apply the contents of the first sector of the applicator to the chromatographic medium. Subsequent to the application of the contents of the first sector of the applicator of the chromatographic medium, the contents of the second sector of the applicator are applied to the chromatographic medium to provide a wash.

Another embodiment of the present invention encompasses assay devices adapted for the performance of a competitive immunoassay using a labeled analyte analogue. One version of this embodiment comprises:

(1) a first opposable component including:
   (a) a chromatographic medium having a first end and a second end, and having immobilized thereon analyte or an immunological analogue thereof in a discrete area substantially smaller than the area of the chromatographic medium;
   (b) a first conductor in operable contact with the first end of the chromatographic medium; and
   (c) a second conductor in operable contact with the second end of the chromatographic medium;
(2) a second opposable component including a first applicator containing a first specific binding partner to the analyte in a form that can be resolubilized by addition of a first aqueous liquid to the first applicator; and
(3) a third opposable component including:
   (a) a second applicator containing a second labeled specific binding partner to the analyte in a form that can be resolubilized by the addition of a second aqueous liquid to the second applicator, the second specific binding partner being labeled with a detectable label; and
   (b) an absorber separated from the second applicator.

In this device, the first and second opposable components are configured so that bringing the first and second opposable components into opposition places the first conductor in operable contact with the first applicator so that the contents of the first applicator are applied to the chromatographic medium and are drawn through at least a portion of the chromatographic medium. The first and third opposable components are configured so that bringing the first and third opposable components into opposition places the absorber in operable contact with the first conductor to withdraw fluid from the chromatographic medium. Bringing the first and third opposable components into opposition causes the second applicator to come into operable contact with the second conductor so that the contents of the second applicator are applied to the chromatographic medium and are drawn through at least a portion of the chromatographic medium overlapping the portion through which the contents of the first applicator are drawn.

In this device, the first specific binding partner and the second, labeled, specific binding partner are preferably each antibody for the analyte. Preferably, the immobilized analyte or analogue thereof comprises analyte covalently linked to a protein lacking specific binding activity for the analyte.

A method for using this assay device for the detection of an analyte by a competitive immunoassay comprises:

(1) applying the sample to the first applicator of the chromatographic assay device, the sample comprising the first aqueous liquid;
(2) applying a reconstitution fluid to the second applicator, the reconstitution fluid comprising the second aqueous liquid;
(3) bringing the first and second opposable components of the chromatographic assay device into opposition, such that the sample and the resolubilized first specific binding partner of the analyte are applied to the first conductor and then to the first end of the chromatographic medium;
(4) allowing a sample and a resolubilized first specific binding partner to move through at least a portion of the chromatographic medium blocking binding sites on the immunological analogue immobilized in the discrete area;
(5) separating the first and second opposable components so that they are no longer in opposition;
(6) bringing the first and third opposable components into opposition such that the resolubilized labeled second specific binding partner is applied to the second conductor and then to the second end of the chromatographic medium;
(7) allowing the resolubilized labeled second specific binding partner to move through at least a portion of chromatographic medium overlapping the entire chromatographic medium through which the sample and the resolubilized first specific binding partner is drawn so that, in the presence of analyte in the test sample, the labeled second specific binding partner binds to the analyte or immunological analogue thereof immobilized in the discrete area due to the binding of sample and analyte with the first specific binding partner; and
(8) observing and/or measuring the second specific binding partner in the discrete area to detect and/or determine the analyte.

Preferably, this method further comprises the step of incubating the chromatographic assay device following applying the sample of the first applicator in order to promote the reaction between the analyte and the first specific binding partner.

In an alternative assay method using this device, a first reconstitution fluid can be applied to the first applicator in addition to the sample.

Other versions of an assay device according to the present invention suitable for competitive immunoassays can be used similarly.

Another version of an assay device according to the present invention for performing a competitive immunoassay comprises:

(1) a first opposable component including:
  (a) a chromatographic medium having a first end and a second end and having immobilized thereon, in separate discrete and non-overlapping areas, each area being substantially smaller than the area of the chromatographic medium:
    (i) a specific binding partner for the analyte; and
    (ii) a secondary specific binding partner, the secondary specific binding partner capable of binding a member of a specific binding pair that lacks affinity for the analyte, the secondary specific binding partner being located closer to the first end of the chromatographic medium than the first specific binding partner;
  (b) a first conductor in operable contact with the first end of the chromatographic medium; and
  (c) a second conductor in operable contact with the second end of the chromatographic medium;
(2) a second opposable component including:
  (a) an applicator containing an analyte analogue, the analyte analogue comprising analyte covalently linked to a member of a specific binding pair lacking affinity for the analyte and bindable by the secondary specific binding partner, the member of the specific binding pair being labeled with a detectable label, the analyte analogue being in a form that can be resolubilized by the addition of an aqueous liquid to the applicator; and
  (b) an absorber separated from the applicator.

In this device, the first and second opposable components are configured so that bringing the first and second opposable components into opposition places the second conductor in operable contact with the applicator so that the contents of the applicator are applied to the chromatographic medium and are drawn through at least a portion of the chromatographic medium, and places the absorber in operable contact with the first conductor to withdraw fluid from the chromatographic medium.

This version of the device preferably further comprises a cover hingedly attached to the first opposable component so that it can be folded over the first and second opposable components when they are opposed. The cover has an aperture cut therein to permit viewing of at least a portion of the chromatographic medium when the first and second opposable components are opposed and the cover is folded over the first and second opposable components.

Preferably, in this version, the first specific binding partner is an antibody specific for the analyte and the secondary specific binding partner is a second antibody capable of binding an immunoglobulin lacking specificity for the analyte. Preferably, the analyte analogue comprises analyte covalently linked to an immunoglobulin from a species and the specific binding partner is antibody specific for this species.

This version can further comprise a third opposable component which contains an absorber positioned such that when the first and third opposable components are opposed, the absorber is brought into contact with the entire chromatographic medium and both conductors. In this version, an aperture is formed behind the chromatographic medium which permits viewing of at least a portion of the chromatographic medium from the back when the second opposable component is folded over the first opposable component and the third opposable component is folded over the second opposable component.

In another variation, the area of the secondary specific binding partner immobilized on the chromatographic medium is divided into at least two discrete and non-overlapping bands, with the quantity of secondary specific binding partner in each band being determined so that the quantity of analyte analogue binding to the detection zone, and thus the concentration of analyte in the test sample, is indicated by the number of bands to which the analyte analogue binds.

Yet another version of an assay device according to the present invention suitable for competitive immunoassays employs a biotin-avidin link. This version of the device comprises:

(1) a first opposable component comprising a chromatographic medium having a first end and a second end and having immobilized thereon, in separate discrete non-overlapping areas, each area being substantially smaller than the area of the chromatographic medium;
  (a) a substance capable of specifically binding biotin selected from the group consisting of avidin, streptavidin, anti-biotin antibody, and derivatives thereof; and
  (b) a secondary specific binding partner capable of specifically binding a three-component complex, the three-component complex comprising:
    (i) analyte;
    (ii) a member of a specific binding pair lacking specific binding affinity for the analyte, the member covalently conjugated to the analyte; and
    (iii) a detectable label bound to the member of the specific binding pair;
(2) a second opposable component including a first applicator containing a first specific binding partner to the analyte in a form that can be resolubilized by the addition of an aqueous sample to the first applicator, the first specific binding partner being covalently linked to biotin, the first specific binding partner not capable of being bound by the secondary specific binding partner;
(3) a third opposable component including:
  (a) a second applicator containing the three-component complex, the complex being in a form that can be resolubilized by the addition of a second aqueous liquid to the second applicator; and
  (b) an absorber separated from the second applicator.

In this device, the first and second opposable components are configured so that bringing the first and second opposable components into opposition places the first conductor in operable contact with the first applicator so that the contents of the first applicator are applied to the chromatographic medium and are drawn through at least a portion of the chromatographic medium. The first and third opposable components are configured so that bringing the first and third opposable components into opposition places the absorber in contact with the first conductor to withdraw fluid from the chromatographic medium, and causes the second applicator to come into operable contact with the second conductor so that the contents of the second applicator are applied to the chromatographic medium and are drawn through at least a portion of the chromatographic medium overlapping the portion to which the contents of the first applicator are drawn.

Preferably, the first specific binding partner is an anti-analyte antibody. The member of the specific binding pair in the three-component complex can be rabbit immunoglobulin G, in which case the secondary specific binding partner can be goat anti-rabbit IgG. Preferably, the substance capable of specifically binding biotin is streptavidin.

The area of the secondary specific binding partner immobilized on the chromatographic medium can divided into at least two discrete and non-overlapping bands, with the quantity of secondary specific binding partner in each band being determined so that the quantity of three-component complex binding to the detection zone, and thus the original analyte concentration in the test sample, is indicated by the number of bands to which the three-component complex binds.

Yet another version of a chromatographic assay device according to the present invention suitable for performing a competitive immunoassay comprises:

(1) a first opposable component including:
   (a) a chromatographic medium having a first end and a second end, and having immobilized thereon in separate and non-overlapping discrete areas each substantially smaller than the area of the chromatographic medium:
      (i) an analyte analogue capable of binding a specific binding partner for the analyte; and
      (ii) a secondary specific binding partner that is capable of binding a specific binding pair member that has affinity for the analyte, the secondary specific binding partner itself lacking binding affinity for the analyte; and
   (b) a conductor in operable contact with the first end of the chromatographic medium; and
(2) a second opposable component including an applicator containing a specific binding partner to the analyte in a form that can be resolubilized by addition of an aqueous liquid to the applicator.

In this device, the first and second opposable components are configured so that bringing the first and second opposable components into opposition places the conductor in operable contact with the applicator so that the contents of the applicator are applied to the chromatographic medium and are drawn through at least a portion of the chromatographic medium.

Preferably, the first specific binding partner is antibody specific for the analyte and the analyte analogue comprises analyte covalently linked to a protein lacking specific binding activity for the analyte or for the specific binding partner for the analyte. Preferably, the secondary specific binding partner binds the antibody specific for the analyte on the basis of species-specific interactions not involving the antigen-combining site of the antibody for the analyte.

In this device, the area of the secondary specific binding partner immobilized on the chromatographic medium can be divided into at least two discrete and non-overlapping bands, with the quantity of secondary specific binding partner in each band being determined so that the quantity of labeled specific binding partner for the analyte binding to the detection zone, and thus the quantity of analyte in the test sample, is indicated by the number of bands to which the labeled specific binding partner for the analyte binds.

Another version of an assay device according to the present invention suitable for performing a competitive immunoassay is a three-component device involving two steps of reagent migration through the chromatographic medium, both occurring in the same direction. This device comprises:

(1) a first opposable component including:
   (a) a chromatographic medium having a first end and a second end and having immobilized thereon, in separate discrete and non-overlapping areas, each area being smaller than the area of the chromatographic medium:
      (i) a specific binding partner for the analyte; and
      (ii) a secondary specific binding partner as described above, the specific binding partner for the analyte being located closer to the first end of the chromatographic medium;
   (b) a first conductor in operable contact with the first end of the chromatographic medium, the first conductor capable of functioning as a first applicator; and
   (c) a second conductor in operable contact with the second end of the chromatographic medium;
(2) a second opposable component including:
   (a) a second applicator containing an analyte analogue as described above, the analyte analogue being in a form that can be resolubilized by the addition of an aqueous liquid to the applicator; and
   (b) a first absorber separated from the second applicator; and
(3) a third opposable component including a second absorber.

In this device, the first and second opposable components are configured so that bringing the first and second opposable components into opposition places the second applicator into operable contact with the first conductor, and places the first absorber into operable contact with the second conductor. The first and third opposable components are configured so that bringing the first and third opposable components into opposition places the second absorber into direct contact with the first conductor and with the chromatographic medium to withdraw fluid therefrom.

BRIEF DESCRIPTION OF THE DRAWINGS

These and other features, aspects, and advantages of the present invention will become better understood with reference to the following description, appended claims, and accompanying drawings where:

FIG. 3 is a drawing of another version of a two-component assay device according to the present invention with a sample preparation zone incorporated into the first opposable component;

FIG. 4 is a drawing of an alternative of the version of FIG. 3 with an absorber on the second opposable component rather than on the first opposable component;

FIG. 5 is a drawing of another version of a two-component assay device according to the present invention with a sample preparation zone and an absorber located on the same opposable component;

FIG. 9 is a drawing of yet another version of a two-component assay device according to the present invention incorporating a discontinuity between a conductor and the chromatographic medium that is bridged when the device is closed;

FIG. 10A is a drawing of yet another version of a two-component assay device according to the present invention incorporating a detector application pad in operable contact with the chromatographic medium;

FIG. 10B is a sectional rear view of the two-component assay device of FIG. 10A, showing details of the components in opposition;

FIG. 11A is a drawing of yet another version of a two-component assay device according to the present invention, generally similar to the version of FIG. 10, but with the detector application pad in direct contact with the chromatographic medium;

FIG. 11B is a sectional rear view of the two-component assay device of FIG. 11A, showing details of the components in opposition;

FIG. 16A is a drawing of yet another two-component assay device suitable for bidirectional chromatography, incorporating a cover;

FIG. 16B is a top view of the two-component chromatographic assay device of FIG. 16A shown with the two components having been brought into opposition;

FIG. 17A is a drawing of a three-component assay device according to the present invention;

FIG. 17B is a sectional rear view of the three-component assay device of FIG. 17A, showing details of the components in opposition;

FIG. 18 is a drawing of a three-component assay desire according to the present invention, in which the third component acts to absorb fluid from the entire chromatographic medium and both conductors;

FIG. 21 is a drawing of a different version of a multiplex assay device according to the present invention adapted to receive a test card;

FIG. 22 is a drawing of yet another version of a multiplex assay device according to the present invention adapted to receive a test card;

FIG. 23 is a drawing of a version of a three-component assay device according to the present invention suitable for performing a competitive immunoassay employing a labeled antibody binding to an analyte analogue immobilized on the chromatographic medium;

FIG. 24 is a drawing of a two-component assay device with a cover suitable for performing a competitive immunoassay using a labeled analyte analogue;

FIG. 25 is a drawing of a three-component assay device suitable for performing a unidirectional competitive immunoassay using a labeled analyte analogue, in which the third component acts to absorb fluid from the entire chromatographic medium and both conductors;

FIG. 26 is a drawing of a three-component assay device according to the present invention suitable for performing a competitive immunoassay, the device using a biotin-avidin link;

FIG. 27 is a drawing of a two-component assay device suitable for performing a competitive immunoassay using a labeled anti-analyte antibody; and FIG. 28 is a depiction of an assay device according to the present invention suitable for receiving a swab or similar sampling device and designed for detection of Streptococcus A antigen.

DESCRIPTION

Definitions

Figure 1A:
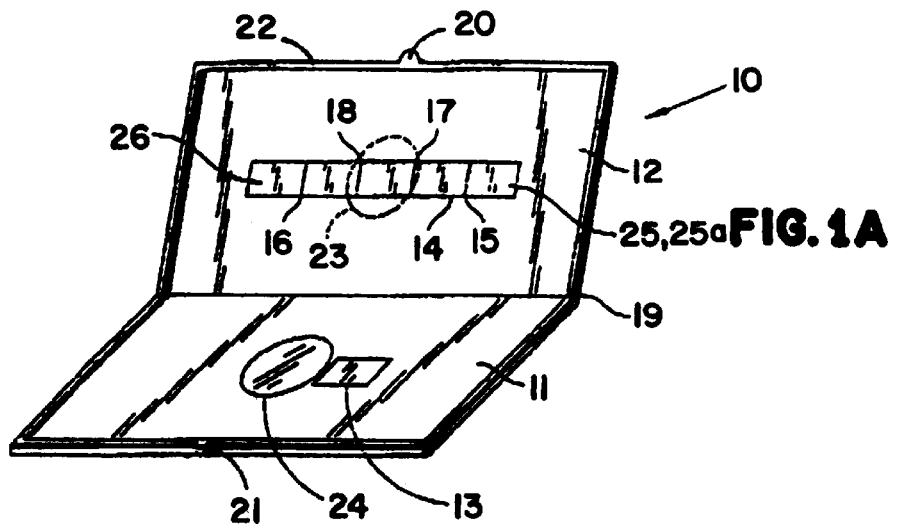
FIG. 1A is a drawing of one version of a two-component chromatographic assay device according to the present invention.

In the context of this disclosure, the following terms are defined as follows unless otherwise indicated:

Specific Binding Partner: A member of a pair of molecules that interact by means of specific noncovalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable Contact: Two solid components are in operable contact when they are in contact, either directly or indirectly, in such a manner that an aqueous liquid can flow from one of the two components to the other substantially uninterruptedly, by capillarity or otherwise. "Direct contact" means that the two elements are in physical contact, such as edge-to-edge or front-to-back. Typically, when two components are in direct contact, they are overlapped with an overlap of about 0.5 to about 3 mm. However, the components can be placed with abutting edges. "Indirect contact" means that the two elements are not in physical contact, but are bridged by one or more conductors.

Finite Capacity: An absorber has finite capacity when it becomes saturated by liquid received during the normal performance of an assay in the device in which the absorber is located. At that point, the absorber can release additional liquid absorbed and become at least partially conductive.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits.

Secondary Specific Binding Partner: An additional specific binding partner that binds to a member of a pair of specific binding partners when the pair of specific binding partners is interacting is designated a secondary specific binding partner. For example, a pair of specific binding partners can comprise Giardia antigen and rabbit anti-Giardia antibody. In that case, the secondary specific binding partner can be goat anti-rabbit IgG antibody. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin.

Outline of the Disclosure

For the convenience of the reader, and as an aid to understanding the organization of the disclosure, the following outline of the disclosure is presented, setting out the organization of the disclosure in terms of the section headings.

I. CHROMATOGRAPHIC ASSAY DEVICES
   A. Two-Component Devices
   1. General Arrangement
   2. Particular Embodiments of Two-Component Device
      a. Device with Conductive Connecting Member on Second Component
      b. Device with Sample Preparation Zone on First Opposable Component
      c. Device with Absorber on Second Component
      d. Device with Sample Preparation Zone and Absorber on Same Opposable Component
      e. Device with Two Detector Application Pads on Different Opposable Components
      f. Device Including Two Separate Applicators on Same Opposable Component
      g. Device with Two Applicators and Absorber on Second Opposable Component
      h. Device with Gap or Discontinuity Between Conductor and Chromatographic Medium
      i. Device with Pad for Labeled Specific Binding Partner on Same Opposable Component as Chromatographic Medium
      j. Device with Detector Application Pad in Direct Contact with First End of Chromatographic Medium
      k. Bidirectional Device Including Second Applicator and Absorber on Second Opposable Component
      l. Bidirectional Device Including Two Applicators and Conductor
      m. Device with Detector Application Pad on First Component
      n. Device with Two-Sector Applicator to Provide Wash
   B. Two-Component Device with Cover
   C. Three-Component Device
   D. Multiplex Devices
   1. Basic Multiplex Device
   2. Multiplex Device with Collapsible Well
   3. Multiplex Devices Adapted to Receive Test Card
II. CHROMATOGRAPHIC ASSAY DEVICES FOR COMPETITIVE ASSAYS
   A. Three-Component Bidirectional Flow Device
   B. Two-Component Bidirectional Flow Device with Cover
   C. Three-Component Unidirectional Flow Device with Absorber
   D. Three-Component Bidirectional Flow Device Using Specificity of Biotin
   E. Two-Component Device for Competitive Inhibition Immunoassay
III. ANALYTES AND ANTIBODIES FOR USE WITH ASSAY DEVICES
IV. TEST KITS

I. CHROMATOGRAPHIC ASSAY DEVICES

One aspect of the present invention comprises chromatographic assay devices particularly useful for the assay of analytes in biological samples. These devices are suitable for the direct application of biological samples, without preliminary extraction steps, and are constructed so as to minimize interference with assay results caused by particulates or colored samples.

The device has at least two substantially planar opposable components. One of the substantially planar components has on its surface a chromatographic medium.

The device also has means for opposing the opposable component and applying pressure thereto. The pressure applied is sufficient to transfer fluid from one opposable component to another opposable component in a direction substantially normal to the opposable components so that the sample is applied to the chromatographic medium for detection and/or determination of the analyte thereon. The pressure also drives fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. The pressure is generated by placing the opposable components into opposition and maintained by holding the components into opposition by engagers such as locks or clasps.

Devices according to the present invention can be constructed for the performance of either a sandwich or a competitive assay.

When the device is constructed for the performance of a sandwich immunoassay, typically at least one of the opposable components of the device has incorporated thereon a first, labeled, specific binding partner to the analyte. This first, labeled, specific binding partner to the analyte is in a form that can be resolubilized by an aqueous liquid. The aqueous liquid used for resolubilization can be the sample. The first, labeled, specific binding partner is positioned so that it can react with the analyte in the sample.

In a device suitable for the performance of a sandwich immunoassay, the chromatographic medium has incorporated thereon a detection zone of a second, unlabeled, specific binding partner for the analyte immobilized thereto. The detection zone is substantially smaller than the chromatographic medium. These components are arranged so that a ternary complex comprising: (1) the first, labeled, specific binding partner; (2) the analyte; and (3) the second, unlabeled, specific binding partner binds at the detection zone if analyte is present in the sample.

In a device suitable for the performance of a competitive immunoassay, the chromatographic medium has incorporated thereon in at least one zone substantially smaller than the chromatographic medium a member of a specific binding pair selected from the group consisting of the analyte or an analogue thereof and a specific binding partner for the analyte. Several different arrangements are possible for devices according to the present invention that are suitable for the performance of competitive immunoassays. These different arrangements are described below.

Typically, detection and/or determination of the analyte after the sample is applied in a chromatographic medium occurs by use of a visually detectable labeled component. The labeled component is preferably either the analyte or an analogue thereof linked to a visually detectable label, or a specific binding partner for the analyte linked to a visually detectable label.

Assay devices according to the present invention can be constructed for the performance of more than one assay simultaneously. In such devices, one of the substantially planar components has at least two separate and non-contacting chromatographic media thereon.

A variation of the device is particularly suitable for bidirectional chromatography, although not restricted to that use. This device has at least three substantially planar opposable components. One of the substantially planar components has on its surface a chromatographic medium having first and second ends. The three-component device also has means for opposing the opposable components pairwise in at least two different combinations and applying pressure thereto, by holding the opposed components together by engagers such as locks or clasps. The pressure is sufficient to transfer fluid from one opposable component to another in a direction substantially normal to the opposable components and to drive the fluid through the chromatographic medium. This causes the sample to be applied to the chromatographic medium and flow through the chromatographic medium from the first end to the second end.

The device also has at least one applicator and one absorber located on one of the opposable components and positioned in such manner that, when the opposable component on which the applicator and the absorber are located is brought into opposition to the opposable component on which the chromatographic medium is located, a second liquid is applied to the chromatographic medium. The second liquid flows through the chromatographic medium from the second end to the first end. This reverses the flow through the chromatographic medium. Detection and/or determination of the analyte is made subsequent to reversal of the flow.

A. Two-Component Devices

One embodiment of the assay device of the present invention is a two-component chromatographic assay device operating in one dimension with one-directional flow.

1. General Arrangement of Two-Component Device

In general, a two-component chromatographic assay device according to the present invention comprises:

(1) A first opposable component including a sample preparation zone adapted to receive a sample to be assayed; and (2) A second opposable component including a chromatographic medium.

In this device, the first and second opposable components can be brought into opposition when the device is closed so as to cause a sample preparation zone to apply the sample to be assayed to the chromatographic medium. In use, the first and second opposable components are typically brought into opposition after a detection reagent is applied to the sample preparation zone. When the first and second opposable components are brought into opposition, the sample preparation zone applies the sample and detection reagent to the chromatographic medium. After the sample and detection reagent is allowed to traverse at least a portion of the chromatographic medium, so that the detection reagent gives a detectable indication of the presence and/or quantity of the analyte; the detection reagent is then observed and/or measured in at least a portion of the chromatographic medium. This results in detection and/or determination of the analyte.

The description of the details of construction of this basic device also applies, as far as possible, to other two-component and three-component assay devices according to the present invention.

The detection reagent comprises the first specific binding partner for the analyte as described above; it may comprise additional components.

This process can give a qualitative and/or quantitative indication of the analyte, depending upon the density of the second specific binding partner in the detection zone and the size of the detection zone.

Typically, to achieve results, the assay requires from 30 seconds to 10 minutes, more typically, from 1 to 5 minutes, including any period of incubation of the sample on the sample preparation zone, as well as the time required for chromatography itself. Typically, the assay is performed at room temperature, although it can be performed at 4° C. or up to 37° C. or higher in some cases, depending upon the nature of the analyte and specific binding partners. In some cases, performing the assay at a lower temperature may be desirable to limit degradation, while in other cases, performing the assay at a higher temperature with suitable analytes and specific binding partners may speed up the assay.

This general arrangement of the chromatographic assay device is shown in FIG. 1A. The chromatographic assay device 10 has a first opposable component 11 and a second opposable component 12. The first opposable component 11 includes a sample preparation zone 13. The second opposable component 12 contains a chromatographic medium 14. The chromatographic medium 14 has a first end 15 and a second end 16; the chromatographic medium 14 contains a detection zone 17 and a control zone 18. The first opposable component 11 and the second opposable component 12 are joined by a hinge 19. The first and second opposable components 11 and 12 preferably further comprise engagers that secure the first and second opposable components in opposition. The engagers can comprise locks, such as locks 20 and 21 that are engaged when the first opposable component 11 and the second opposable component 12 are brought into opposition. The construction and dimensions of the locks 20 and 21 can be varied to exert the optimal degree of pressure on the opposable components 11 and 12. The degree of pressure that is optimal may depend on the thickness and construction of the chromatographic medium 14, the intended sample volume, and other factors. To guard against leakage of samples or reagents, a sealing ridge or gasket 22 is positioned around the perimeter of the first and second opposable components 11 and 12. Although the use of the engagers, such as the locks 20 and 21, and of the sealing ridge or gasket 22, is generally preferred, these components are not necessary to construct a basic device according to the present invention. The second opposable component 12 has a first window 23; optionally, the first opposable component 11 can have a second window 24 to permit viewing of the chromatographic medium 14 from either side. The second window 24 permits viewing of the chromatographic medium 14 from the surface opposite the surface to which the reagents are applied. As another option, the first window 23 can be absent and the second window 24 used for viewing of the chromatographic medium 14. In general, two-component devices according to the present invention can have either one or two windows, also known as apertures, to allow viewing of the chromatographic medium either through the opposable component not carrying the chromatographic medium, as window 23 in FIG. 1, or through the opposable component carrying the chromatographic medium, as window 24 in FIG. 1. Alternatively, the first and/or second opposable components 11 and 12 can be made of transparent or translucent materials, so that the chromatographic medium 14 can be viewed without a separate aperture or window.

Figure 1B:
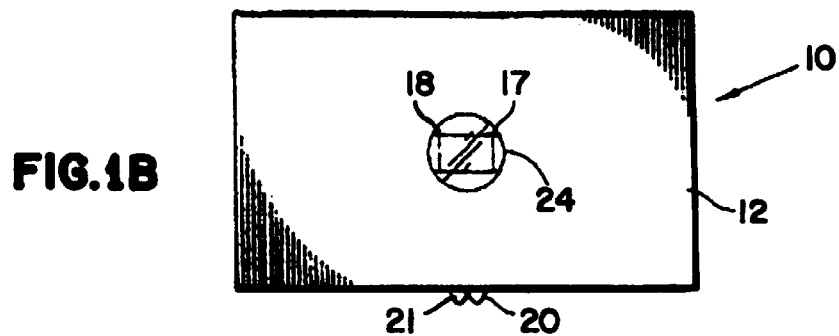
FIG. 1B is a drawing of the two-component chromatographic assay device of FIG. 1A shown with the two components having been brought into opposition.

FIG. 1B shows the device 10 after the opposable components 11 and 12 have been brought into opposition. The chromatographic medium 14, including the detection zone 17 and the control zone 18, is visible through window 23. The sample preparation zone 13 contacts the chromatographic medium 14 at or near the first end 15 so that the contents of the sample preparation zone 13 can flow through the chromatographic medium 14, including the detection zone 17 and the control zone 18.

The device 10 can, optionally, further comprise a conductor 25 in operable contact with the first end 15 of the chromatographic medium 14, as shown in FIG. 1A. The conductor 25 can be a material such as cellulose or other material that can conduct an aqueous liquid without substantially absorbing it. The conductor 25 can be treated with a surfactant so that the reagents can be applied more evenly to the chromatographic medium 14. When the conductor 25 is present, the sample preparation zone 13 preferably contacts the conductor 25 when the first and second opposable components 11 and 12 are brought into opposition.

The device 10 can further comprise an absorber 26 in operable contact with the second end 16 of the chromatographic medium 14 to aid in drawing fluid through the chromatographic medium 14 from the first end 15 toward the second end 16, as shown in FIG. 1A.

The sample preparation zone 13 can be made of any suitable material, such as, but not limited to, cellulose, paper, nylon, rayon, glass fiber, fleeces, or non-woven synthetic fabrics. The porosity of the sample preparation zone 13 can be chosen to filter out cellular or particulate matter in samples such as whole blood or fecal samples. The sample preparation zone 13 can contain at least one reagent for treatment of the sample before the sample is applied to the chromatographic medium 14.

The reagents that can be present in the sample preparation zone 13 vary with the sample to be applied to the sample preparation zone 13 and with the analyte to be assayed. They can include, but are not limited to, acids or alkalis to adjust the pH, buffers to stabilize the pH, chelating agents such as EDTA or EGTA to chelate metals, hydrolytic enzymes to lyse the cell membrane of animal cells or the cell wall of bacteria to liberate analytes, substrates or coenzymes for enzymes, and the like. One particularly useful extraction reagent is a mixture of sodium nitrite and acetic acid to generate nitrous acid. The sodium nitrite can be present in dried form on the sample preparation zone 13, and the acetic acid can be added to the sample preparation zone 13 after the addition of the sample.

The sample, or optionally, a sampling device such as a throat swab or a microporous filter, can be placed by the operator on the sample preparation zone 13; if needed, other reagents can be added.

The bodies of the first and second opposable components 11 and 12 are preferably made of laminated cardboard that is sufficiently impervious to moisture to contain the liquids involved in the performance of the assay. Other cellulose-based materials, such as paperboard or solid bleached sulfite (SBS) can also be used. Alternatively, the bodies can be made of plastic that is impervious to moisture. A suitable plastic is a polycarbonate plastic such as Lexan™.

The hinge 19 is preferably made of material that is impermeable to an aqueous liquid, such as a plastic that can be compatibly joined with or is the same as the material used for the bodies of the first and second opposable components 11 and 12.

Typically, the chromatographic medium 14, absorber 26, conductor 25, and other liquid-receiving components are secured to the bodies of the first and second opposable components 11 and 12 by adhesive. Suitable adhesives are well known in the art. Other joining methods, such as stapling or tacking, can also be used.

The analyte is detected either by means of a labeled specific binding partner to the analyte or by the use of a labeled secondary specific binding partner for a specific binding partner to the analyte. In most cases, the use of a labeled specific binding partner to the analyte is preferred. The label of the labeled specific binding partner is preferably a visually detectable label, such as a colloidal metal label. Preferably, the colloidal metal label is gold, silver, bronze, iron, or tin; most preferably, it is gold. The preparation of gold-labeled antibodies is described in J. DeMey, "The Preparation and Use of Gold Probes," in *Immunocytochemistry: Modern Methods and Applications* (J. M. Polak & S. VanNoorden, eds., Wright, Bristol, England, 1986), Ch. 8, pp. 115–145, incorporated herein by this reference. Antibodies labeled with colloidal gold are commercially available, such as from Sigma Chemical Company, St. Louis, Mo.

Alternatively, other colloidal labels, such as a colloidal sulfur label or a dye-silica label, can also be used. In a less preferred alternative, the visually detectable label can be a colored latex label. It is also possible to use other labels, such as radioactive labels.

Although Applicants do not necessarily intend to be bound by this theory, when an aqueous liquid containing a sample is applied to a resolubilizable specific binding partner labeled with a colloidal metal label, such as colloidal gold, the kinetics of the reaction between the analyte and the labeled specific binding partner are extremely rapid. These rapid kinetics result in the substantially complete labeling of analyte before the combination of the analyte and the labeled specific binding partner is applied to the chromatographic medium. Thus, in a one-directional chromatographic procedure performed with an assay device according to the present invention, what is chromatographed is predominantly the binary complex of the analyte and the corresponding labeled specific binding partner. This allows separation of this complex from contaminants not binding the specific binding partner and improves accuracy of the assay.

In this embodiment, the labeled specific binding partner preferably is present on the sample preparation zone 13 in a form that can be resolubilized by the addition of an aqueous liquid to the sample preparation zone. Typically, the aqueous liquid is the sample itself. In some cases, particularly where small sample volumes are used, it may be desirable to add additional buffer or other aqueous liquid to the sample preparation zone.

In other embodiments discussed below, the labeled specific binding partner can be present on an element of the chromatographic assay device that is separate from the sample preparation zone but comes into contact with it during the performance of the assay. In these embodiments, the labeled specific binding partner is preferably present in a resolubilizable form on this element, and is resolubilized when the sample comes into contact with the element. In some cases, the labeled specific binding partner can be resolubilized by the addition of a separate aqueous liquid, distinct from the sample, to the element.

The chromatographic medium 14 on the second opposable component 12 is a flat strip. It is typically rectangular, having first and second ends 15 and 16. Throughout this Description, the term "first end" 15 refers to the end of the chromatographic medium 14 at which the sample is applied, and the term "second end" 16 refers to the opposite end. The original direction of flow of the sample is from the first end 15 toward the second end 16 of the chromatographic medium 14. The chromatographic medium 14 is composed of a material suitable as a medium for thin-layer chromatography of analytes and analyte-antibody conjugates, such as nitrocellulose, nylon, rayon, cellulose, paper, or silica. The chromatographic medium 14 can be pretreated or modified as needed. Typically, the chromatographic medium 14 is translucent, so that colored zones appearing on it as a result of the assay can be viewed from either side.

In some applications, it is preferable to place a second flexible transparent support on the top of the chromatographic medium 14 to regulate the flow of the sample through the membrane and prevent migration over the top of the membrane. Suitable flexible transparent supports include polyethylene, vinyl, Mylar®, and cellophane.

When the chromatographic assay device 10 is to be used for an assay such as a sandwich immunoassay, the chromatographic medium can further comprise a detection 17 zone substantially smaller than the chromatographic medium 14. This detection zone can contain a second specific binding partner to the analyte immobilized thereto against diffusion. The second specific binding partner can be bound to the chromatographic medium by either covalent or non-covalent means. If the analyte to be assayed is an antigen or hapten, the second specific binding partner can be an antibody to the antigen or the hapten. Alternatively, the analyte can be an antibody and the second specific binding partner can be a hapten or an antigen capable of being bound specifically by the antibody.

The chromatographic medium 14 can further comprise a control zone 18 substantially smaller than the chromatographic medium 14, and separate from the detection zone 17. The control zone 18 can comprise analyte immobilized thereto non-diffusibly in order to bind labeled antibody that is not bound at the detection zone 17 by the formation of a ternary "sandwich" complex. Any such antibody is bound by the immobilized analyte and forms a detectable zone or band. This provides a check on the operation of the assay and the correct binding of the reagents, as described below. The methods used to bind the second specific binding partner in the detection zone 17 and the analyte in the control zone 18 are well known in the art and need not be described further.

Alternatively, for some analytes, such as carbohydrates, it may be difficult or impossible to fix the analyte stably to the chromatographic medium 14. In such cases, the control zone 18 can comprise an immobilized zone of antibody specific for the labeled anti-analyte antibody. For example, if the analyte is the Streptococcus A-specific carbohydrate, and the labeled antibody is rabbit IgG specific for Streptococcus A antigen, the control zone 18 can comprise goat antibody to rabbit IgG. In such cases, to prevent complete capture of the labeled anti-analyte antibody in the detection zone 17 at high analyte concentration and consequent disappearance of the labeled anti-analyte antibody from the control zone 18, it can be desirable to add labeled antibody not specific for the analyte and of a different species than the labeled anti-analyte antibody. Such antibody can constitute immunologically indifferent immunoglobulin or an antibody to an analyte not found in the test sample. The control zone 18 would then comprise anti-species antibody or analyte not found in the test sample.

Several variations of this device are possible. In one variation, as discussed above, the sample preparation zone 13 can further contain a specific binding partner for the analyte labeled with a detectable label in a form that can be resolubilized by the addition of an aqueous liquid to the sample preparation zone 13. The aqueous liquid can be the sample itself. The labeled specific binding partner can be freeze-dried or reversibly precipitated so that it is resolubilized and mobilized by the addition of the sample to the sample preparation zone. In this variation, it is not necessary to add a detection reagent to the sample preparation zone 13, as the detection reagent is automatically generated by the addition of the sample to the sample preparation zone 13.

In another variation, the conductor 25 in operable contact with the first end 15 of the chromatographic medium 14 on the second operable component can be replaced by an absorber 25a of finite capacity in operable contact. The absorber 25a is located so that it comes into contact with the sample preparation zone 13 when the first 11 and second 12 opposable components are placed into opposition, to apply the sample to the absorber. This may be useful in controlling the flow of sample into the chromatographic medium 14 so that the chromatographic medium 14 is not overloaded.

In this version, the absorber 25a can contain a labeled specific binding partner for the analyte in a form that can be resolubilized, as described above. In this arrangement, the labeled specific binding partner is resolubilized when the first and second opposable components 11 and 12 are brought into opposition, applying the sample to the absorber 25a. The combination of the sample and the resolubilized labeled specific binding partner then enters the chromatographic medium 14 at its first end 15.

2. Particular Embodiments of Two-Component Device
  a. Device with Conductive Connecting Member on Second Component In one embodiment of a two-component device according to the present invention, the first opposable component comprises:

(1) A sample preparation zone; and
(2) A chromatographic medium that is not in communication with the sample preparation zone.

The second opposable component comprises a conductive connecting member. The first and second opposable components can be brought into opposition so as to cause the connecting member to establish a communication between the sample preparation zone and the chromatographic medium so as to result in the application of the sample to the chromatographic medium.

Figure 2:
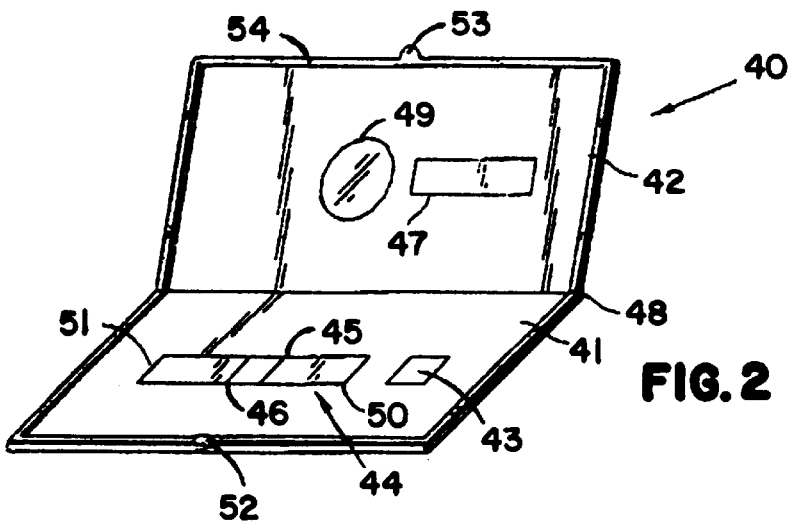
FIG. 2 is a drawing of a version of a two-component chromatographic assay device according to the present invention in which the first opposable component includes a sample preparation zone and a chromatographic medium that is not in communication with the sample preparation zone, and the second opposable component includes a conductive connecting member.

This embodiment is depicted in FIG. 2. The chromatographic assay device 40 comprises a first opposable component 41 and a second opposable component 42. The first opposable component includes a sample preparation zone 43 and a chromatographic medium 44, with a first end 50 and a second end 51. The chromatographic medium 44 has a detection zone 45 and a control zone 46. The second opposable component 42 includes a conductive connecting member 47. The first and second opposable components 41 and 42 are connected by a hinge 48. The first and second opposable components 41 and 42 also include engagers such as locks 52 and 53, with a gasket 54 surrounding the first and second opposable components 41 and 42. The second opposable component 42 has an aperture 49 to permit viewing of the chromatographic medium 44.

When the first and second opposable components 41 and 42 are brought into opposition, the sample preparation zone 43 on the first opposable component 41 is brought into contact with the conductive connecting member 47 on the second opposable component 42, which in turn is brought into contact with the first end 50 of the chromatographic medium 44 to apply the sample to the chromatographic medium 44.

In variations of the device of FIG. 2, the conductive connecting member 47 can contain a specific binding partner for the analyte labeled with a detectable label in a form that can be resolubilized by the addition of an aqueous liquid. In this variation, the sample is added to the sample preparation zone 43. Alternatively, the sample preparation zone 43 can be used for addition of labeled specific binding partner for the analyte in liquid form, with the sample itself being added to the conductive connecting member 47. In yet another alternative, the sample preparation zone 43 can contain resolubilizable specific binding partner for the analyte, with the sample again being added to the conductive connecting member 47.

b. Device with Sample Preparation Zone on First Opposable Component

Another embodiment of a chromatographic assay device according to the present invention is a device that incorporates a sample preparation zone on the first opposable component, i.e., the component on which the chromatographic medium is located. Typically, in this embodiment, the second opposable component comprises an applicator incorporating a labeled specific binding partner for the analyte in a form that can be resolubilized.

In this embodiment, bringing the first and second opposable components into opposition brings the applicator into contact with the sample preparation zone so that the labeled specific binding partner for the analyte is resolubilized.

Preferably, the first opposable component further comprises a conductor, and operable contact between the sample preparation zone and the chromatographic medium is achieved by having the sample preparation zone and the chromatographic medium both in operable contact with the conductor.

Preferably, the first opposable component further comprises an absorber in operable contact with the second end of the chromatography medium.

The chromatographic medium is preferably constructed as described above, with detection and control zones.

This embodiment of the assay device is shown in FIG. 3. The chromatographic assay device 60 has a first opposable component 61 and a second opposable component 62. The first opposable component 61 includes a sample preparation zone 63, a conductor 64 in operable contact with the sample preparation zone 63, a chromatographic medium 65 having a first end 66 and a second end 67, and an absorber 68 in operable contact with the second end 67 of the chromatographic medium 65. The chromatographic medium 65 contains a detection zone 69 and a control zone 70. The second opposable component 62 contains an applicator 71, preferably incorporating a labeled specific binding partner in a form that can be resolubilized. The first opposable component 61 and the second opposable component 62 are joined by a hinge 72. The second opposable component 62 contains a window 73 to allow viewing of at least a portion of the chromatographic medium 65. The first and second opposable components 61 and 62 have engagers such as locks 74 and 75, with a gasket 76 surrounding the first and second opposable components 61 and 62.

In operation, a sample is applied to the sample preparation zone 63. The first and second opposable components 61 and 62 are then brought into opposition so that the sample in the sample preparation zone 63 resolubilizes the contents of the applicator 71, including the labeled specific binding partner. The contents of the sample preparation zone 63 and the applicator 71 are then applied to the chromatographic medium 65 through the sample preparation zone 63 and the conductor 64.

c. Device with Absorber on Second Component

In an alternative of this embodiment, the absorber can be placed on the second opposable component instead of the first opposable component. In this alternative, the absorber comes into operable contact with the second end of the chromatographic medium when the first and second opposable components are placed in opposition. This allows for a larger absorber, which can be desirable when it is necessary to use a larger sample, such as in the detection of an analyte present only in low concentrations.

This alternative of the embodiment is shown in FIG. 4. The chromatographic assay device 80 comprises the first opposable component 81 and the second opposable component 82. The first opposable component 81 includes the sample preparation zone 83, the conductor 84 in operable contact with the sample preparation zone 83, and the chromatographic medium 85 having the first end 86 and the second end 87, with the detection zone 88 and the control zone 89. The second opposable component 82 contains the applicator 90 and the absorber 91; the applicator 90 is separated from the absorber 91 on the second opposable component 82. The first opposable component 81 and the second opposable component 82 are joined by a hinge 92. The second opposable component 82 also contains an aperture 93 to permit viewing of at least a part of the chromatographic medium 85. The first and second opposable components 81 and 82 also include engagers such as locks 94 and 95 and a gasket 96, as described above.

In use, the sample is applied to the sample preparation zone 83, where extraction or other treatment of the sample can occur. The sample then enters the first end 86 of the chromatographic medium 85 by flowing through the conductor 84, as described above. When the first opposable component 81 and the second opposable component 82 are brought into opposition, the applicator 90 is brought into operable contact with the conductor 84 to resolubilize the labeled specific binding partner in the applicator 90 and apply the resolubilized labeled specific binding partner to the conductor 84 and then to the first end 86 of the chromatographic medium 85, which causes the resolubilized labeled specific binding partner to enter the chromatographic medium 85. The absorber 91 is simultaneously brought into operable contact with the second end 87 of the chromatographic medium 85 to withdraw fluid from the chromatographic medium 85.

d. Device with Sample Preparation Zone and Absorber on Same Opposable Component

Another embodiment of a chromatographic assay device according to the present invention is a two-component device in which the sample preparation zone and the absorber are located on the same opposable component. This has the advantage in certain applications of being able to use a larger absorber to withdraw fluid more rapidly and efficiently from the second end of the chromatographic medium.

This embodiment of the two-component chromatographic assay device is shown in FIG. 5. The chromatographic device 100 has a first opposable component 101 and a second opposable component 102 connected by a hinge 103. The first opposable component 101 includes a chromatographic medium 104 having a first end 105 and a second end 106, and a conductor 107 in operable contact with the first end 105 of the chromatographic medium 104. The chromatographic medium 105 contains a detection zone 108 and, optionally, a control zone 109.

The second opposable component 102 includes a sample preparation zone 110 for receiving a sample to be assayed and an absorber 111 separated from the sample preparation zone 110. The sample preparation zone 110 can contain a labeled specific binding partner for the analyte in resolubilizable form. The second opposable component 102 has an aperture 112 therein to permit viewing of the chromatographic medium. The first and second opposable components 101 and 102 have engagers such as locks 113 and 114, and a gasket 115, as described above.

When the first 101 and second 102 opposable components are brought into opposition, the sample preparation zone 110 comes into operable contact with the conductor 107 to apply the sample to the conductor 107 and then to the first end 105 of the chromatographic medium 104. The absorber 111 comes into operable contact with the second end 106 of the chromatographic medium 104 to withdraw fluid from the second end 106 of the chromatographic medium 104. In other respects, the design and operation of this device is similar to that depicted in FIG. 4, above.

e. Device with Two Detector Application Pads on Different Opposable Components

Yet another embodiment of a two-component assay device according to the present invention incorporates two separate detector application pads on different opposable components. This arrangement is particularly useful when it is desired to use a large volume of a labeled specific binding partner, as when a labeled antibody is only available in dilute form and attempts to concentrate the antibody would denature or inactivate it.

Figure 6:
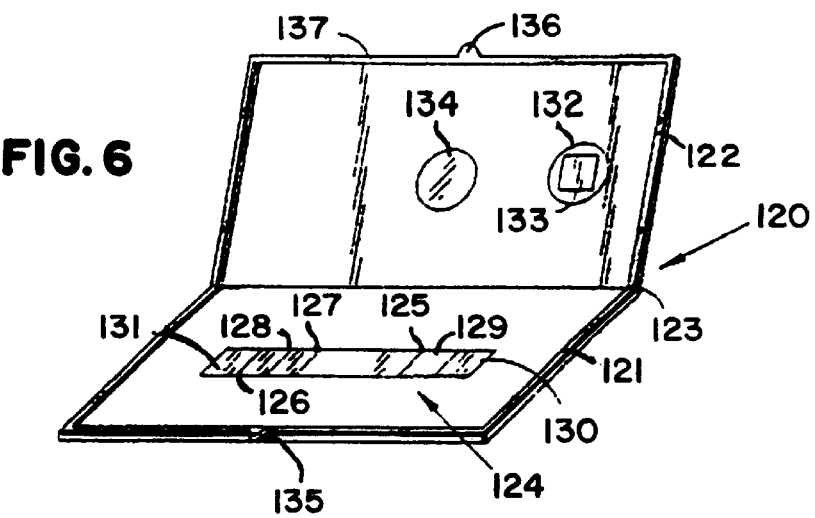
FIG. 6 is a drawing of yet another version of a two-component assay device according to the present invention with two detector application pads on different opposable components.

This embodiment of the two-component, chromatographic assay device is depicted in FIG. 6. The chromatographic assay device 120 has a first opposable component 121 and a second opposable component 122 connected by a hinge 123. The first opposable component 121 includes a chromatographic medium 124 having a first end 125 and a second end 126. The chromatographic medium 124 includes a detection zone 127, and, optionally, a control zone 128.

The first opposable component 121 also has a first detector application pad 129 in operable contact with the first end 125 of the chromatographic medium 124. The first detector application pad 129 contains a first specific binding partner to the analyte in a form that can be resolubilized by the addition of an aqueous liquid to the first detector application pad 129. The first specific binding partner is typically labeled with a detectable label. The first opposable component 121 also has a conductor 130 in operable contact with the first detector application pad 129 so that the first detector application pad 129 bridges the conductor 130 and the first end 125 of the chromatographic medium 124. The first opposable component 121 also has an absorber 131 in operable contact with the second end 126 of the chromatographic medium 124.

The second opposable component 122 includes a sample preparation zone 132 for receiving a sample to be assayed. The second opposable component 122 also contains a second detector application pad 133 in operable contact with the sample preparation zone 132, with the sample preparation zone 132 being placed over the second detector application pad 133. The sample preparation zone 132 and the second detector application pad 133 can be held together by a fastener or adhesive. The second detector application pad 133 and the sample preparation zone 132 are positioned so that a sample applied to the sample preparation zone 132 must pass through the sample preparation zone 132 before entering the second detector application pad 133. The second detector application pad 133 contains a second specific binding partner for the analyte in a form that can be resolubilized by the addition of a sample to the sample preparation zone 132. The second detector application pad 133 is positioned such that application of the sample to the sample preparation zone 132 resolubilizes the second specific binding partner so that the sample preparation zone 132 contains a mixture of the sample and the second specific binding partner.

The second specific binding partner is labeled with a detectable label. Preferably, the first and second specific binding partners are identical and the detectable labels labeling the first and the second specific binding partners are identical.

The second opposable component 122 also contains an aperture 134 therein to allow viewing of at least a portion of the chromatographic medium 124, including the detection zone 127 and, if present, the control zone 128. The first and second opposable components 121 and 122 also have engagers such as locks 135 and 136, and a gasket 137 as described above for the basic two-component device.

When the first and second 121 and 122 opposable components are brought into opposition, the sample preparation zone 132 is brought into contact with the conductor 130 to apply the sample and the second specific binding partner to the conductor 130 and then to the first end 125 of the chromatographic medium 124 through the first detector application pad 129. Thus, the sample sequentially contacts the second specific binding partner and then the first specific binding partner before being applied to the first end 125 of the chromatographic medium 124 for chromatography. This results in a greater volume of labeled specific binding partner being in contact with the sample to increase the sensitivity of the assay.

f. Device Including Two Separate Applicators on Same Opposable Component

Yet another embodiment of a chromatographic assay device according to the present invention including two separate applicators on the same opposable component. These two applicators are not in operable contact until they are bridged by a conductor on the opposing element when the elements are brought into opposition.

Figure 7:
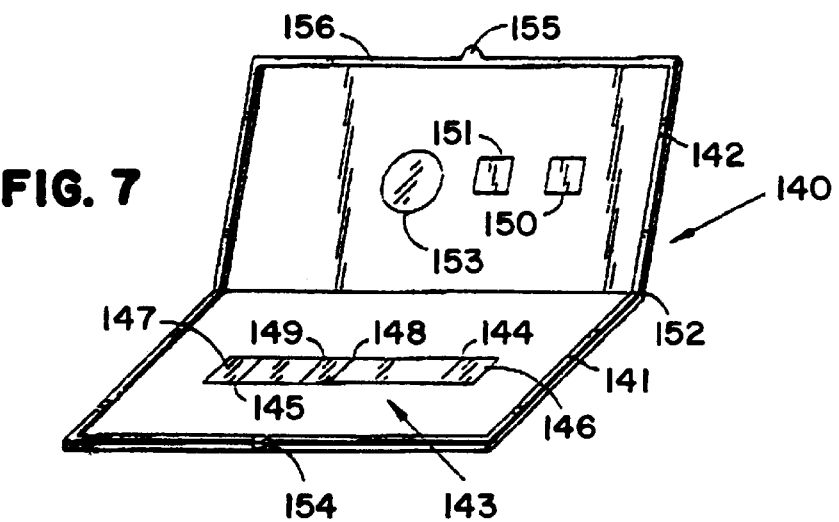
FIG. 7 is a drawing of yet another version of a two-component assay device according to the present invention incorporating two applicators on one of the components.

This embodiment of the chromatographic assay device is shown in FIG. 7. The chromatographic assay device 140 has a first opposable component 141 and a second opposable component 142. The first opposable component 141 includes a chromatographic medium 143 having a first end 144 and a second end 145, a conductor 146 in operable contact with the first end 144, and an absorber 147 in operable contact with the second end 145 of the chromatographic medium 143. The chromatographic medium 143 contains a detection zone 148 and a control zone 149. The second opposable component 142 contains a first applicator (sample application pad) 150 and a second applicator (detector application pad) 151. The first applicator 150 and the second applicator 151 are not in operable contact until the first opposable component 141 and the second opposable component 142 are brought into opposition. When the first opposable component 141 and the second opposable component 142 are brought into opposition, the first applicator 150 is brought into contact with the conductor 146 and the second applicator 151 is brought into contact with both the conductor 146 and the first end 144 of the chromatographic medium 143. The overlap is typically several millimeters; i.e., enough to ensure transfer of fluid. This results in the first applicator 150 and the second applicator 151 being bridged by the conductor 146 so that the contents of the first applicator 150 and the second applicator 151 are applied to the chromatographic medium 143. The first opposable component 141 and the second opposable component 142 are joined by a hinge 152. The second opposable component 142 contains a window 153 to allow viewing of the chromatographic medium 143. The first and second opposable components 141 and 142 also include engagers such as locks 154 and 155 and a gasket 156.

The first applicator 150 can comprise a sample application pad and the second applicator 151 can comprise a detector application pad, to which detecting reagent can be applied. When the first and second opposable components 141 and 142 are brought into opposition, the contents of the sample application pad and the detector application pad are applied to the chromatographic medium 143 via the conductor 146.

Preferably, the second applicator 151 (detector application pad) contains a specific binding partner for the analyte labeled with a detectable label in a form that can be resolubilized by the addition of an aqueous liquid to the second applicator 151. The aqueous liquid is typically the sample itself, which resolubilizes the labeled specific binding partner when the first 141 and second 142 opposable components are brought into opposition. In some assays, it may be desirable to add a separate reconstituting aqueous liquid to the detector application pad. Alternatively, the labeled specific binding partner can be applied in liquid form to the second applicator 151.

g. Device with Two Applicators and Absorber on Second Opposable Component

In another variation of this embodiment, the absorber can be relocated from the first opposable component (i.e., the opposable component containing the chromatographic medium) to the second opposable component (i.e., the opposable component containing the first and second applicators). This allows the use of a larger sample and can be desirable for detection of analytes present in low concentration.

Figure 8:
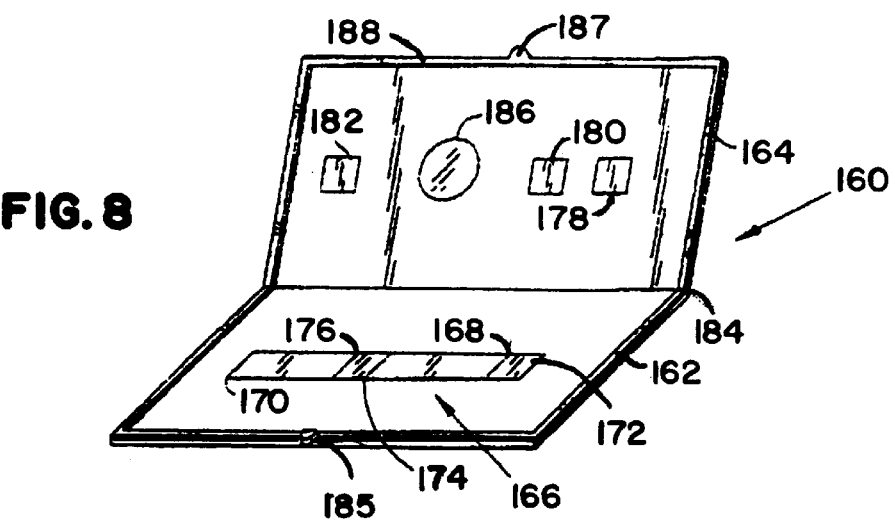
FIG. 8 is a drawing of an alternative of the version of FIG. 7 with an absorber on the second opposable component rather than on the first opposable component.

This variation is shown in FIG. 8. The chromatographic assay device 160 has a first opposable component 162 and a second opposable component 164. The first opposable component 162 includes a chromatographic medium 166 having a first end 168 and a second end 170 and a conductor 172 in operable contact with the first end 168 of the chromatographic medium 166. The chromatographic medium 166 contains a detection zone 174 and a control zone 176. The second opposable component 164 contains a first applicator (sample application pad) 178 and a second applicator (detector application pad) 180. The first applicator 178 and the second applicator 180 are not in operable contact until the first opposable component 162 and the second opposable component 164 are brought into opposition, and are then bridged as described above for the assay device depicted in FIG. 7. The second opposable component 164 also contains an absorber 182 that is separated from the first applicator 178 and the second applicator 180. When the first opposable component 162 and the second opposable component 164 are brought into opposition, the first applicator 178 and the second applicator 180 are bridged by the conductor 172 so that the contents of the first applicator 178 and the second applicator 180 are applied to the chromatographic medium 166. Simultaneously, the absorber 182 is brought into operable contact with the second end 170 of the chromatographic medium 166 to absorb fluid from the chromatographic medium 166. The first opposable component 162 and the second opposable component 164 are joined by a hinge 184. The second opposable component 164 contains a window 186 to allow viewing of the chromatographic medium 166. The first and second opposable components 162 and 164 also include engagers such as locks 185 and 187, and a gasket 188.

h. Device with Gap or Discontinuity Between Conductor and Chromatographic Medium A further variation of this device incorporates a gap or discontinuity between the conductor and the chromatographic medium so that the path of fluid flow is from the first applicator through the conductor, then through the second applicator, and finally through the chromatographic medium.

This variation of the device is shown in FIG. 9. The chromatographic assay device 190 has a first opposable component 191 and a second opposable component 192. The first opposable component 191 includes a chromatographic medium 193 having a first end 194 and a second end 195, a conductor 196 not in operable contact with the first end 194 of the chromatographic medium 193 when the device 190 is in open position, and an absorber 197 in operable contact with the second end 195 of the chromatographic medium 193. The chromatographic medium 193 contains a detection zone 198 and a control zone 199. The second opposable component 192 contains a first applicator (sample application pad) 200 and a second applicator (detector application pad) 201. The first applicator 200 and the second applicator 201 are not in operable contact until the first opposable component 191 and the second opposable component 192 are brought into opposition. When the first opposable component 191 and the second opposable component 192 are brought into opposition, by closing a hinge 203 connecting the first opposable component 191 and the second opposable component 192, the first applicator 200 and the second applicator 201 are bridged by the conductor 196 and the second applicator 201 contacts the chromatographic medium 193. Thus, the path of fluid flow is from the first applicator 200 through the conductor 196, then through the second applicator 201, and then into the chromatographic medium 193. The second opposable component 192 contains a window 202 to allow viewing of the chromatographic medium 193. The first and second opposable components 191 and 192 also include engagers such as locks 204 and 205, and a gasket 206, as described above.

i. Device with Pad for Labeled Specific Binding Partner on Same Opposable Component as Chromatographic Medium Yet another embodiment of a chromatographic assay device according to the present invention is a two-component device incorporating a pad for a labeled specific binding partner on the same opposable component as the chromatographic medium. In this device, the sample applicator is located on the other opposable component.

This embodiment of a chromatographic assay device according to the present invention is depicted in FIG. 10A. The chromatographic assay device 210 has a first opposable component 212 and a second opposable component 214. The first opposable component 212 has a chromatographic medium 216 having a first end 218 and a second end 220. The chromatographic medium has a detection zone 222 and, optionally, a control zone 224, as described above for other variations of assay devices suitable for sandwich immunoassays. The first opposable component 212 also has a conductor 226 in operable contact with the first end 218 of the chromatographic medium 216, and an absorber 228 in operable contact with the second end 220 of the chromatographic medium 216. The first opposable component 212 also has a detector application pad 230 in direct contact with the conductor 226 and positioned such that it is in indirect contact with the first end 218 of the chromatographic medium 216. The second opposable component 214 has a sample application pad 232. The first opposable component 212 and the second opposable component 214 are joined by a hinge 234. When the first opposable component 212 and the second opposable component 214 are brought into opposition, the sample application pad 232 is brought into contact with the detector application pad 230. The second opposable component 214 contains a window 236 to allow viewing of the chromatographic medium 216. The first and second opposable components 212 and 214 have engagers such as locks 233 and 235, and a gasket 237, as described above.

A sectional rear view of the device 210 is depicted in FIG. 10B. The section shown in FIG. 10B is taken from the view of FIG. 10A along the line 10B, between the chromatographic medium 216 and the hinge 234 looking toward the edge opposite the hinge 234. FIG. 10B shows the first opposable component 212 and second opposable component 214 in opposition. The sample application pad 232 is shown in contact with the detector application pad 230. The detector application pad 230 is in contact with the conductor 226, which is in turn in contact with the first end 218 of the chromatographic medium 216. The detection zone 222 and control zone 224 of the chromatographic medium 216 are shown. The second end 220 of the chromatographic medium 216, nearer the control zone 224, is in contact with the absorber 228.

Bringing the first and second opposable components 212 and 214 into opposition causes the sample application pad 232 to apply the sample to be tested to the detector application pad 230 and thus to the first end 218 of the chromatographic medium 216 though the conductor 226.

Preferably, the detector application pad 230 contains a first specific binding partner to the analyte in a form that can be resolubilized by addition of an aqueous liquid to the detector application pad 230, and the first specific binding partner is labeled with a detectable label.

Preferably, the contents of the sample application pad 232 after a sample is applied thereto comprises an aqueous liquid, and the aqueous liquid applied to the detector application pad 230 comprises the contents of the sample application pad. In this arrangement, there is no additional liquid needed to resolubilize the labeled specific binding partner.

In a variation of this device, the absorber is located on the second opposable component instead of being located on the first opposable component. The absorber is separated from the sample application pad also located on the second opposable component and is placed in operable contact with the second end of the chromatographic medium when the first opposable component and the second opposable component are brought into opposition, as shown above in FIG. 5.

j. Device with Detector Application Pad in Direct Contact with First End of Chromatographic Medium A further variation of this device omits the conductor between the detector application pad and the chromatographic medium, so that the detector application pad is in direct contact with the first end of the chromatographic medium. In this variation, when the first and second opposable components are brought into opposition, the detector application pad and the sample application pad are in contact except for the region of the detector application pad directly adjacent to the first end of the chromatographic medium. There is a slight gap or offset at that region of the detector application pad, so that sample cannot flow directly from the sample application pad to the chromatographic medium. This gap or offset is typically from about 0.5 mm to about 2 mm, more typically from about 0.5 mm to about 1 mm.

This variation is particularly suitable for the detection of fecal occult blood by use of a labeled anti-hemoglobin antibody, and can detect concentrations of hemoglobin corresponding to as much as 17 ml of blood per 100 g feces (13 mg hemoglobin per gram of feces), without the occurrence of false negatives due to a high dose "hook" effect.

This variation is depicted in FIG. 11A. The chromatographic assay device 250 has a first opposable component 252 and a second opposable component 254. The first opposable component 252 has a chromatographic medium 256 having a first end 258 and a second end 260. The chromatographic medium 256 has a detection zone 262 and a control zone 264. The first opposable component 252 also has an absorber 266 in operable contact with the second end 260 of the chromatographic medium 256. The first opposable component 252 also has a detector application pad 268 in direct contact with the first end 258 of the chromatographic medium 256. The second opposable component 254 has a sample application pad 270. The first opposable component 252 and the second opposable component 254 are joined by a hinge 272. When the first opposable component 252 and the second opposable component 254 are brought into opposition, the sample application pad 270 is brought into contact with the detector application pad 268, except for a narrow gap or offset 274 at the end of the detector application pad 268 in contact with the first end 258 of the chromatographic medium 256. This gap 274 prevents sample applied to the sample application pad 270 from flowing directly into the chromatographic medium 266. The second opposable component 254 has a window 276 to allow viewing of the chromatographic medium 256. The first and second opposable components 252 and 254 have engagers such as locks 278 and 280, and a gasket 282 as described above.

A sectional rear view of the device 250 of FIG. 11A along the line 11A is depicted in FIG. 11B. The section shown in FIG. 11B is taken from the view of FIG. 11A between the chromatographic medium 256 and the hinge 272 looking toward the edge opposite the hinge 272. FIG. 11B shows the first opposable component 252 and second opposable component 254 in opposition, with the hinge 272 in closed position. The sample application pad 270 is shown in contact with the detector application pad 268, except for the small gap 274 at the end of the detector application pad 268 nearest the chromatographic medium 256. The detector application pad 268 is in direct contact with the first end 258 of the chromatographic medium 256. The detection zone 262 and control zone 264 of the chromatographic medium 256 are shown. The second end 260 of the chromatographic medium 256, nearer the control zone 264, is in contact with the absorber 266.

k. Bidirectional Device Including Second Applicator and Absorber on Second Opposable Component Another embodiment of a chromatographic assay device according to the present invention comprises a device capable of carrying out bidirectional chromatography.

Figure 12A:
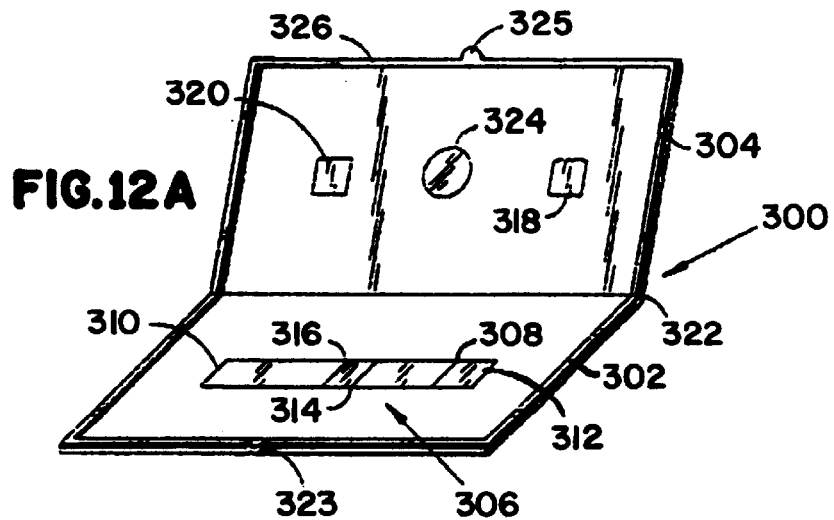
FIG. 12A is a drawing of a version of a two-component assay device according to the present invention suitable for carrying out bidirectional chromatography.

This embodiment of the chromatographic assay device is shown in FIG. 12A. The assay device 300 has a first opposable component 302 and a second opposable component 304. The first opposable component 302 has a chromatographic medium 306 having a first end 308 and a second end 310. The first opposable component 302 also has a first applicator 312 in operable contact with the first end 308 of the chromatographic medium 306. The chromatographic medium 306 also comprises a detection zone 314 and, optionally, a control zone 316 located between the detection zone 314 and the second end 310 of the chromatographic medium 306. The detection zone 314 and control zone 316 are constituted as discussed above for other embodiments of the device suitable for sandwich immunoassays. The second opposable component 314 includes an absorber 318, which can be an absorbent pad, and a second applicator 320. The first 312 and second 314 opposable components are joined by a hinge 322. The second opposable component 314 includes a window 324 to permit viewing of the chromatographic medium 306. The first and second opposable components 312 and 314 include engagers 323 and 325, and a gasket 326, as described above.

Figure 12B:
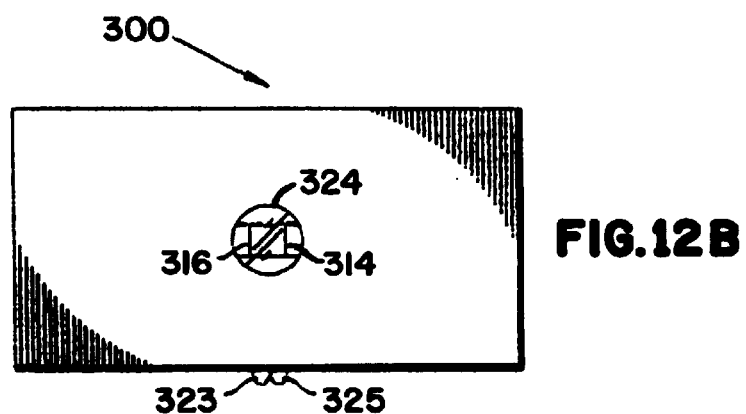
FIG. 12B is a top view of the two-component chromatographic assay device of FIG. 12A shown with the two components having been brought into opposition.

When the hinge 322 is closed, the device 300 appears as shown in a top view in FIG. 12B. The chromatographic medium 306, including the detection zone 314, and if present, the control zone 316, is visible through the window 324.

In this embodiment of the device, addition of a first liquid to the first applicator 312 causes the first liquid to be applied to the first end 308 of the chromatographic medium 306. Bringing the first and second opposable components 302 and 304 into opposition then causes the second applicator 320 to come into operable contact with the second end 310 of the chromatographic medium 306 so as to apply a second liquid to the second end 310 of the chromatographic medium 306, and causes the absorber 318 to come into operable contact with the first applicator 312 so as to withdraw fluid from the chromatographic medium 306 through the first applicator 312, thus reversing the flow. In the operation of this device, the sample is applied to the first applicator 312 and a solution of a labeled specific binding partner is applied to the second applicator 320. The sample then moves through the chromatographic medium 306 from the first end 308 toward the second end 310 so that any analyte present in the sample is bound to the immobilized antibody at the detection zone 314. When the first and second opposable components 302 and 304 are brought into opposition, the labeled specific binding partner is applied to the chromatographic medium 306 and moves through the chromatographic medium 306 from the second end 310 toward the first end 308. The labeled specific binding partner then binds to any analyte bound to the immobilized antibody at the detection zone 314, generating a detectable ternary complex. The labeled specific binding partner also binds to the immobilized analyte or analogue at the control zone 316, giving an indication of correct performance of the assay.

l. Bidirectional Device Including Two Applicators and Conductor

Another embodiment of a chromatographic assay device according to the present invention is a device suitable for bidirectional chromatography that includes an absorber to reverse the flow and a reagent pad in operable contact with the chromatographic medium.

Figure 13A:
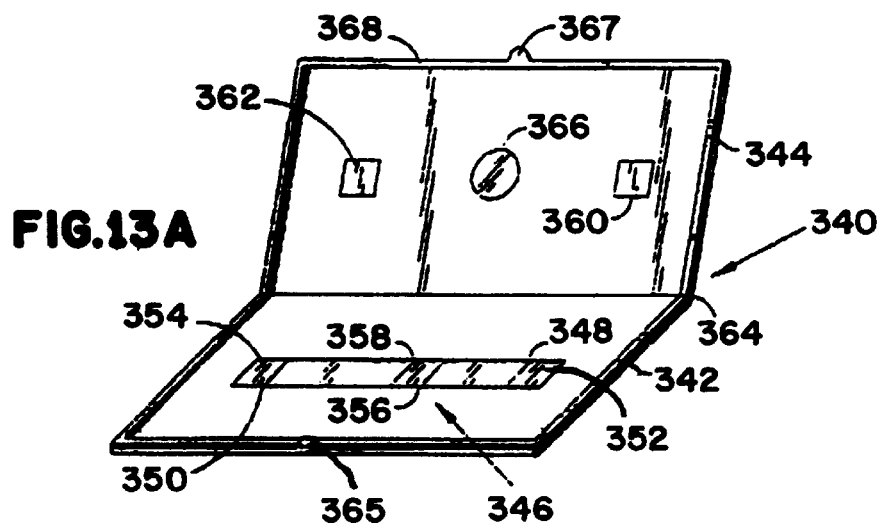
FIG. 13A is a drawing of another version of a two-component assay device suitable for carrying out bidirectional chromatography with two applicators and a conductor.

This embodiment of the chromatographic assay device is shown in FIG. 13A. The assay device 340 has a first opposable component 342 and a second opposable component 344. The first opposable component 342 has a chromatographic medium 346 having a first end 348 and a second end 350. Adjacent to and in operable contact with the first end 348 of the chromatographic medium 346 is a first applicator 352. Adjacent to and in operable contact with the second end 350 of the chromatographic medium 346 is a conductor 354. The chromatographic medium 346 contains a detection zone 356, and optionally, a control zone 358. The second opposable component 344 comprises an absorber 360 and a second applicator 362. The first and second opposable components 342 and 344 are joined by a hinge 364. The second opposable component 344 contains a window 366 to permit viewing of the chromatographic medium 346. The first and second opposable components 342 and 344 include engagers 365 and 367, and a gasket 368 as described above.

When the first and second opposable components 342 and 344 are brought into opposition, the absorber 360 is brought into operable contact with the first applicator 352, and the second applicator 362 is brought into operable contact with the conductor 354, thereby reversing the flow. The portion of the chromatographic medium 346, including the detection zone 356 and, if present, the control zone 358, can be viewed through the window 366 in the second opposable component 344 when the first 342 and second 344 opposable components are placed into opposition.

Figure 13B:
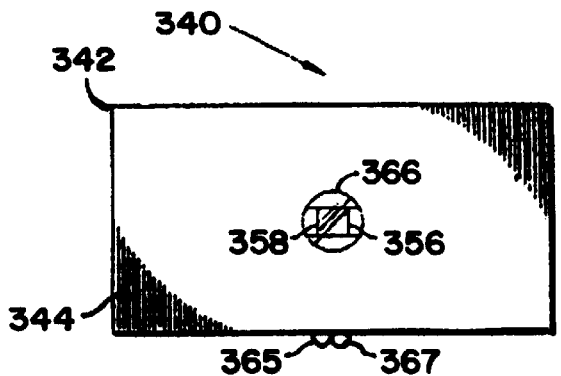
FIG. 13B is a top view of the two-component chromatographic assay device of FIG. 13A shown with the two components having been brought into opposition.

FIG. 13B shows a top view of the device 340 when the first and second opposable components 342 and 344 are placed into opposition; the detection zone 356 and the control zone 358 are visible through the window 366 in the second opposable component 344.

In this device, the first applicator 352 can comprise a sample application pad, to which the sample to be tested is applied, and the second applicator 362 can comprise a buffer application pad to which buffer is added. The first applicator 352 (sample application pad) can contain at least one reagent for treatment of the sample before it is applied to the chromatographic medium, as described above. The second applicator 362 (buffer application pad) typically contains a specific binding partner for the analyte in a form that can be resolubilized by the addition of an aqueous liquid, as described above.

The first applicator 352 (sample application pad) preferably further comprises an inert dye so that the flow of the sample through the chromatographic medium 346 can be monitored visually. Preferably, the inert dye is of a contrasting color to that of the detectable label. For example, when the detectable label is pink colloidal gold, the inert dye can be blue. The migration of sample is monitored by observing the inert dye. After the sample has migrated a sufficient distance, for example, two-thirds or three-fourths of the length of the chromatographic medium 346, the first and second opposable components 342 and 344 are brought into opposition and the absorber 360 is brought into contact with the first applicator 352. This reverses the flow of the sample through the chromatographic medium 346, allowing additional capture of the analyte at the detection zone 356. It also brings the second applicator 362 into contact with the conductor 354 and causes the buffer solution containing resolubilized labeled specific binding partner to the analyte to be applied to the chromatographic medium 346. The buffer solution migrates through the chromatographic medium 346 from the second end 350 toward the first end 348. When it reaches the detection zone 356, labeled specific binding partner to the analyte binds to the analyte already bound to the detection zone 356. Detection and/or determination of the analyte is then performed as described above.

Because the first and second opposable components 342 and 344 are not in contact when the sample is applied as the first liquid to the first applicator 352, it is possible to apply either the sample to the first applicator 352 first or to apply the buffer to the second applicator 362 first to reconstitute the labeled specific binding partner.

A variation of this bidirectional device replaces the conductor 354 on the first opposable component 342 with a first absorber of finite capacity 354a. The absorber 360 on the second opposable component 344 then is a second absorber. The absorber of finite capacity 354a on the first opposable component 344 has the property that liquid can be drawn back through it when the second applicator 362, containing a resolubilizable labeled specific binding partner, is placed in operable contact with it and the second absorber 360 is placed in operable contact with the first applicator 352.

m. Device with Detector Application Pad on First Component

Another embodiment of a two-component chromatographic assay device according to the present invention has a detector application pad located on the first opposable component and a sample preparation zone located on the second opposable component. In this device, the detector application pad is located so that it is in operable contact with the first end of the chromatographic medium. The detector application pad preferably contains a labeled specific binding partner to the analyte in a form that can be resolubilized by the addition of an aqueous liquid to the detector application pad. The device further comprises a conductor in operable contact with the detector application pad and in indirect contact with the first end of the chromatographic medium, as well as an absorber in operable contact with the second end of the chromatographic medium.

In the operation of this embodiment of the device, the sample is applied to the sample preparation zone on the second opposable component, after which the first and second opposable components are brought into opposition. This applies the contents of the sample preparation zone to the conductor, and then to the first end of the chromatographic medium through the detector application pad. When the sample reaches the detector application pad, the contents of the detector application pad are resolubilized. When the contents of the detector application pad include a specific binding partner for the analyte, the passage of the sample through the detector application pad results in the specific binding partner binding to any analyte present in the sample.

Figure 14:
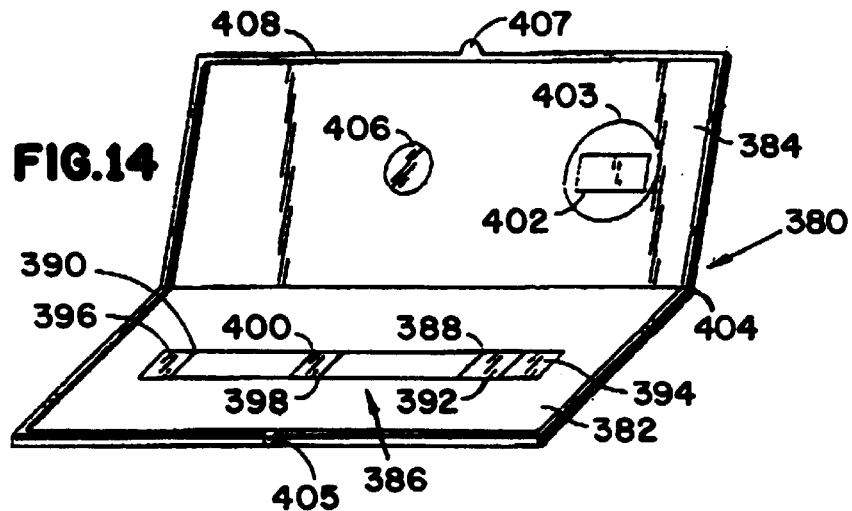
FIG. 14 is a drawing of another two-component assay device according to the present invention with a detector application pad on the first opposable component and a sample preparation zone on the second opposable component.

This embodiment of the device is shown in FIG. 14. The assay device 380 has a first opposable component 382 and a second opposable component 384. The first opposable component 382 includes a chromatographic medium 386 having a first end 388 and a second end 390. The first opposable component 382 also includes a detector application pad 392 in operable contact with the first end 388 of the chromatographic medium 386, a conductor 394 in operable contact with the detector application pad 392 and in indirect contact with the first end 388 of the chromatographic medium 386, and an absorber 396 in operable contact with the second end 390 of the chromatographic medium 386. The chromatographic medium 386 includes a detection zone 398 and a control zone 400. The second opposable component 384 includes a sample preparation zone 402. The first and second opposable components 382 and 384 are joined by a hinge 404. The second opposable component 384 has an aperture 406 to permit viewing of at least a portion of the chromatographic medium 386. The first and second opposable components include engagers 405 and 407, and a gasket 408 as described above.

A variation of this embodiment incorporates a specific binding partner for the analyte in a form that can be resolubilized on the second opposable component 384 as well as on the first opposable component 382. When the resolubilizable specific binding partner is located on the second opposable component 384, it is preferably not located directly in the sample preparation zone 402 itself. Rather, it preferably surrounds the sample preparation zone 402 in an area 403 such that the sample first passes through the sample preparation zone 402 and then moves into the area 403 surrounding the sample preparation zone 402, resolubilizing the specific binding partner. For example, the sample preparation zone 402 can comprise a piece of suitably treated filter paper placed on the surface of the second opposable component 384, adhered by an adhesive or a fastener. This allows for treatment of the sample, e.g., to adjust the pH, lyse intact cells, and/or remove particulates, before the sample contacts the resolubilizable specific binding partner. This variation of this embodiment can provide a wider dynamic range and can be useful when the available antibody has a low affinity or low concentrations of analytes are to be detected.

n. Device with Two-Sector Applicator to Provide Wash

Another embodiment of a two-component assay device according to the present invention has a two-sector applicator to provide a wash of sample unreacted with the labeled specific binding partner after the mixture of the sample and the labeled specific binding partner has passed through the chromatographic medium. This embodiment has the advantage of providing a clearer background and making it easier to read a weakly positive result.

In this embodiment, the first opposable component includes a chromatographic medium having first and second ends, a conductor in operable contact with the first end of the chromatographic medium, and an absorber in operable contact with the second end of the chromatographic medium. The second opposable component includes an applicator divided into two sectors: a first sector containing a labeled specific binding partner for the analyte in resolubilizable form, and a second sector without the labeled specific binding partner. Bringing the first and second opposable components into opposition places the first sector, but not the second sector, of the applicator into direct contact with the conductor, to apply the contents of the first sector of the applicator to the conductor and then to the first end of the chromatographic medium. The second sector is placed in indirect contact with the conductor, as the contents of the second sector flow through the first sector and then to the conductor. Thus, subsequent to the application of the contents of the first sector of the applicator to the conductor, the contents of the second sector are applied to the conductor. The contents of the second sector, which includes sample but no labeled specific binding partner, serve to wash out unbound labeled specific binding partner from the chromatographic medium, thereby reducing the background of visible label seen in the chromatographic medium and improving the reading of the assay device. This is particularly advantageous for weakly positive assays.

Figure 15:
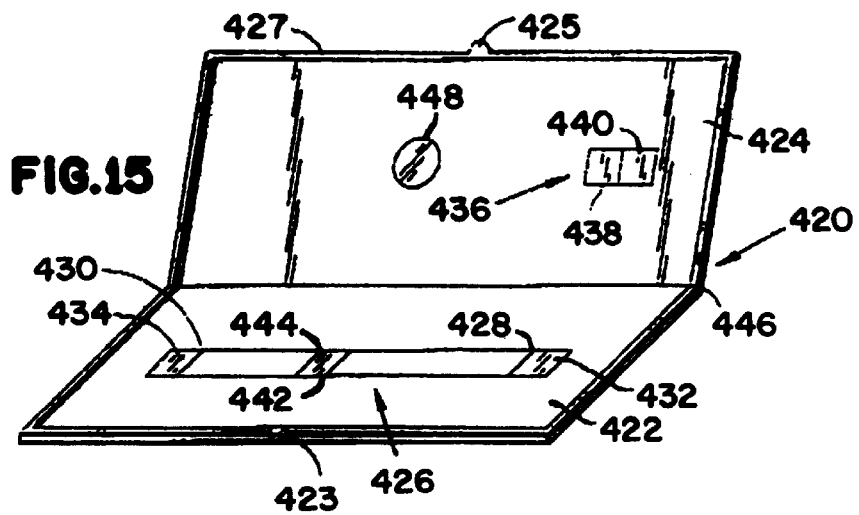
FIG. 15 is a drawing of another two-component assay device according to the present invention with the applicator divided into sectors, providing for a wash of the chromatographic medium with sample free of label.

This embodiment of the assay device is shown in FIG. 15. The assay device 420 has a first opposable component 422 and a second opposable component 424. The first opposable component 422 includes a chromatographic medium 426 with a first end 428 and a second end 430, a conductor 432 in operable contact with the first end 428 of the chromatographic medium 426, and an absorber 434 in operable contact with the second end 430 of the chromatographic medium 426. The second opposable component 424 has an applicator 436 divided into two sectors: a first sector 438 in direct contact with the conductor 432 when the first and second opposable components 422 and 424 are brought into opposition, and a second sector 440 in indirect contact with the conductor 432 when the first and second opposable components 422 and 424 are brought into opposition. The chromatographic medium 426 has a detection zone 442 and a control zone 444. The first and second opposable components 422 and 424 are joined by a hinge 446. The second opposable component 424 has a window 448 to permit viewing of at least a portion of the chromatographic medium 426. The first and second opposable components 422 and 424 also include engagers 423 and 425 and a gasket 427, as described above.

B. Two-Component Device with Cover

Another embodiment of a chromatographic assay device according to the present invention is a two-component device with a cover.

This embodiment of the assay device is shown in FIG. 16A. The assay device 460 has a first opposable component 462, a second opposable component 464, and a cover 466. The second opposable component 464 is hingedly attached to one side of the first opposable component 462 by a first hinge 468. The cover 466 is hingedly attached to the opposite side of the first opposable component 462 by a second hinge 470. The first opposable component 462 has a chromatographic medium 472 having a first end 474 and a second end 476. Adjacent to and in operable contact with the first end 474 of the chromatographic medium 472 is a first applicator or sample pad 478 which is located in a recess 480. The first applicator 478 can include a sample preparation zone that can contain at least one reagent for treatment of the sample before it is applied to the chromatographic medium, as described above. The first applicator 478 can also contain an inert dye to indicate the progress of chromatography as described above. A first absorber 482 is adjacent to and in operable contact with the second end 476 of the chromatographic medium 472. The chromatographic medium 472 contains a detection zone 484 and a control zone 486 and is optionally marked with a limit line 488. The limit line 488 can be optionally marked on the first opposable component 462 as well. The second opposable component 464 comprises a second applicator 490, typically containing a labeled specific binding partner for the analyte, and a second absorber 492. The cover 466 contains a first aperture 494. Preferably, the second opposable component 462 contains a second aperture 496. In this device, the second opposable component 464 and the cover 466 also include engagers 491 and 493. The device 460 is surrounded by a gasket 495 as described above. The cover 466 can also include an engager 497 to hold it in place.

FIG. 16B depicts a top view of this device 460 when the second opposable component 464 is folded over the first opposable component 462 and the cover 466 is folded over the second opposable component 464. A portion of the chromatographic medium 472 is visible through the first aperture 494 of the cover 466 and through the second aperture 496 of the second opposable component 464, including the detection zone 484 and the control zone 486.

In the operation of this device, the addition of a first liquid to the first applicator 478 causes the first liquid to be applied to the first end 474 of the chromatographic medium 472. Typically, the first liquid is a sample that may contain an analyte.

In this device, the function of the recess 480 in the first opposable component 462 is to position the second absorber 492 so that it can be placed at least partially in direct contact with the chromatographic medium 472 in order to remove excess sample, while keeping the first applicator 478 from blocking this contact.

In use, the sample is added to the first applicator 478 so that chromatography can proceed in the chromatographic medium 472 from the first end 474 toward the second end 476. When the dye reaches the limit line 488, the first and second opposable components 462 and 464 are brought into opposition, which causes the second applicator 490 to come into operable contact with the first absorber 482 so as to apply the second liquid to the second end 476 of the chromatographic medium 472 and causes the second absorber 492 to come into operable contact with the first applicator 478 so as to withdraw fluid from the chromatographic medium 472 via the first applicator 478. This reverses chromatographic flow and draws the labeled specific binding partner back through the chromatographic medium 472 from the second end 476 toward the first end 474. This device is therefore useful for bidirectional chromatography.

The cover 466 can be folded over the second opposable component 464 to more securely lock and hold the second opposable component 464 against the first opposable component 462. This allows more convenient storage of the device, after use, as in a medical record.

C. Three-Component Device

Another embodiment of a chromatographic assay device according to the present invention is a three-component assay device utilizing bidirectional chromatography.

This embodiment of the three-component assay device is shown in FIG. 17A. The assay device 520 has a first opposable component 522, a second opposable component 524, and a third opposable component 526. The second opposable component 524 is hingedly attached to one side of the first opposable component 522 by a first hinge 528; the third opposable component 526 is hingedly attached to the opposite side of the first opposable component 522 by a second hinge 530. The first opposable component 522 has a chromatographic medium 532 having a first end 534 and a second end 536. The chromatographic medium 532 has a detection zone 538 and a control zone 540. In operable contact with the first end 534 of the chromatographic medium 532 is a first conductor 542 and in operable contact with the second end 536 of the chromatographic medium 532 is a second conductor 544. The second opposable component 524 comprises a first absorber 546 and a first applicator 548, intended for application of the sample. Typically, the first applicator 548 contains a first specific binding partner for the analyte in a form that can be resolubilized by the application of an aqueous sample to the first applicator 548. A first aperture 550 is cut in the second opposable component 524 to allow viewing of at least a portion of the chromatographic medium 532. The first aperture 550 is between the first absorber 546 and the first applicator 548. The third opposable component 526 comprises a second applicator 552, intended for a labeled secondary specific binding partner, and a second absorber 554. A second aperture 556 is cut in the third opposable component 526 to allow viewing of at least a portion of the chromatographic medium 532. The second aperture 556 is between the second applicator 552 and the second absorber 554. When the device 520 is closed, with the second opposable component 524 folded over the first opposable component 522 and the third opposable component 526 folded over the first opposable component 522, at least a portion of the chromatographic medium 532 is visible through the first aperture 550 and the second aperture 556 (FIG. 17B). The second and third opposable components 524 and 526 includes engagers 551 and 555 to hold the components together. A flexible ridge or gasket 557 surrounds the edges of the components to retain reagents or samples within the device 520. A similar arrangement of engagers and a ridge or gasket is used for other three-component devices, as described below.

In this device, bringing the first and second opposable components 522 and 524 into opposition causes the first absorber 546 to come into operable contact with the second conductor 544 and the first applicator 548 to come into operable contact with the first conductor 542 to apply fluid to the chromatographic medium 532, so that a first liquid applied to the first applicator 548 is drawn through at least a portion of the chromatographic medium 532, including the detection zone 538 and control zone 540.

The first and second opposable components 522 and 524 are then withdrawn from opposition and the first and third opposable components 522 and 526 are brought into opposition. This causes the second absorber 554 to come into operable contact with the first conductor 542 to withdraw fluid from the chromatographic medium 532 and causes the second applicator 552 to come into operable contact with the second conductor 544 to apply fluid to the chromatographic medium 532. This causes a reversal of flow so that a second liquid applied to the second applicator 552 is drawn through at least a portion of the chromatographic medium through which the first liquid has been drawn in the direction opposite to the direction in which the first liquid was drawn through the chromatographic medium 532. The first 522, second 524, and third 526 opposable components are in such a configuration that, when the third opposable component 526 is brought into opposition with the first opposable component 522, the second opposable component 524 can be folded over the first and third opposable components 522 and 526 to form a cover.

In the performance of a serological assay using this device, firm pressure between the second absorber 554 and the first conductor 542 is important to assure that non-specific immunoglobulin is withdrawn from the chromatographic medium 532 before the advancing front of labeled secondary specific binding partner, or to assure the withdrawal of free analyte before advance of labeled specific anti-analyte. If mixing between anti-immunoglobulin label and non-specific immunoglobulin occurs, the non-specific immunoglobulin neutralizes the anti-immunoglobulin label (conjugate) leaving less or none available for labeling the specifically captured immunoglobulin. The third opposable component 526 of the device helps keep consistent pressure applied to reliably effect this function. This is one of the advantages of assay devices according to the present invention.

The first specific binding partner can be directly labeled with a detectable label. Alternatively, indirect labeling of the first specific binding partner can be used. In indirect labeling, the first specific binding partner is not labeled, but is detected by application of a labeled secondary specific binding partner that specifically binds the first specific binding partner by means of the second applicator. Indirect labeling is particularly useful for testing for Giardia or other antigens for which commercially available antibodies are directly labeled only with difficulty. When the first specific binding partner is not directly labeled, the second applicator 552 preferably contains a labeled secondary specific binding partner for the first specific binding partner, as discussed below in Section III.

Another embodiment of a three-component device employs an absorber on the third component that is positioned to remove fluid from the entire chromatographic medium and components in operable contact with it. This serves the purpose of removing excess sample that may create a background color, thus reducing sensitivity.

This embodiment is shown in FIG. 18. The assay device 560 has a first opposable component 561, a second opposable component 562, and a third opposable component 563. The second opposable component 562 is hingedly attached to one side of the first opposable component 561 by a first hinge 564. The third opposable component 563 is hingedly attached to the other side of the first opposable component 561 by a second hinge 565. The first opposable component 561 has a chromatographic medium 566 having a first end 567 and a second end 568.

Adjacent to and in operable contact with the first end 567 of the chromatographic medium 566 is a first applicator 569. Adjacent to and in operable contact with the second end 568 of the chromatographic medium 566 is a conductor 570. The chromatographic medium contains a detection zone 571, and, optionally, a control zone 572. The second opposable component 562 comprises a first absorber 573 and a second applicator 574, typically incorporating a labeled specific binding partner to the analyte in resolubilizable form. The third opposable component 563 comprises a second absorber 575 that extends substantially along the length of the chromatographic medium 566 in order to absorb fluid from the chromatographic medium 566, the first applicator 569, and the conductor 570 when the third opposable component 563 is brought into opposition with the first opposable component 561. The first opposable component 561 has an aperture 576 behind the chromatographic medium 566 for viewing at least a portion of the chromatographic medium 566 at the back of the first opposable component 561. The second and third opposable components 562 and 563 also include engagers 577 and 579, and a gasket 580 as described above.

In use, the sample to be tested is applied to the first applicator 569 and a buffer solution is applied to the second applicator 574. The sample is then allowed to flow through the chromatographic medium 566, including the detection zone 571 and control zone 572. The first and second opposable components 561 and 562 are then brought into opposition, so that the second applicator 574 contacts the first applicator 569 and the first absorber 573 contacts the conductor 570 at the second end 568 of the chromatographic medium 566. This causes the resolubilized labeled specific binding partner originally in the second applicator 574 to flow through the chromatographic medium. After completion of flow of the sample and the resolubilized specific binding partner through the chromatographic medium 566, the third opposable component 563 is brought into opposition with the first opposable component 561 so that the second absorber 575 can remove fluid from the chromatographic medium 566, the first applicator 569, and the conductor 570. The second opposable component 562 is then folded back over the third opposable component 563, and the chromatographic medium 566, including the detection zone 567 and the control zone 568, is viewed through the apertures 576 located behind the chromatographic medium 566.

D. Multiplex Devices

Another embodiment of a chromatographic assay device according to the present invention is a multiplex assay device that can perform multiple assays simultaneously. The assays can be performed on the same analyte or different analytes. In general, all versions of the device described above are suitable for multiplex use by providing first and second opposable components, and third opposable components if necessary, with multiple chromatographic media, sample preparation zones, applicators, conductors, absorbers, and other required elements.

1. Basic Multiplex Device

Figure 19:
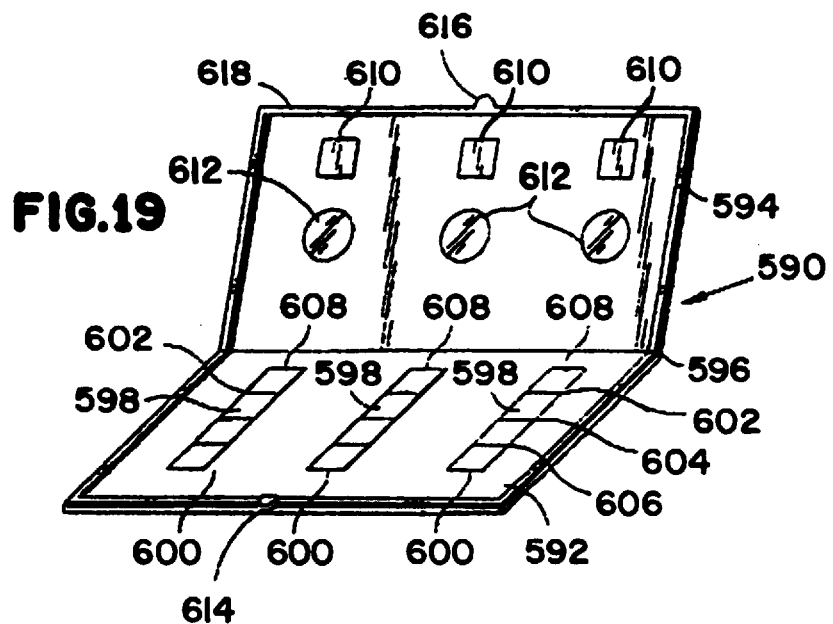
FIG. 19 is a drawing of a multiplex assay device according to the present invention, suitable for the simultaneous assay of one or more samples.

One version of a multiplex assay device according to the present invention is shown in FIG. 19. The assay device 590 has a first opposable component 592 and a second opposable component 594. The second opposable component 594 is hingedly attached to the first opposable component 592 by a hinge 596. The first opposable component 592 comprises a plurality of chromatographic media 598. Each of the chromatographic media 598 has a first end 600 and a second end 602, and comprises a detection zone 604 and a control zone 606. The second end 602 of each chromatographic medium 598 is in operable contact with an absorber 608 to drive flow through the chromatographic medium 598. There is a separate absorber 608 for each chromatographic medium 598. The second opposable component 594 comprises a plurality of sample preparation zones 610, one for each chromatographic medium 598. Typically, each sample preparation zone 610 contains labeled specific binding partner for the analyte to be tested in a form that can be resolubilized by the addition of a liquid sample to the sample preparation zone 610. Alternatively, the labeled specific binding partner in a liquid form can be added to the sample preparation zone 610 before or after the addition of the sample thereto. Bringing the first and second opposable components 592 and 594 into opposition causes each of the sample preparation zones 610 to be applied to the corresponding chromatographic medium 598 at the first end 600. The second opposable component 594 contains a plurality of apertures 612, one for each chromatographic medium 598. The first opposable component 592 and second opposable component 594 include engagers 614 and 616 and a gasket 618, as described above.

This multiplex device can contain from 2 to 12 or more sample preparation zones and chromatographic media, depending upon the assay for which the device is to be employed. Typically, the device contains from 2 to 5 separate sample preparation zones and chromatographic media.

This embodiment of the device can be used to assay a number of different analytes in different aliquots of the same sample, or can be used to assay the same analyte in a number of different samples. This latter mode is particularly useful in assaying for a condition for which samples taken at different times from the same patient must be assayed for the analyte of interest, such as fecal occult blood. The presence of fecal occult blood is frequently determined by means of a series of stool samples taken once a day or at other intervals for a prescribed period. Alternatively, one or more of the assays can be used for controls or reference standards.

2. Multiplex Device with Collapsible Well

In yet another variation of the multiplex device, at least one sample preparation zone could comprise a collapsible well, to which an extraction swab or other sample-containing device can be added. In this variation, the first opposable component can further comprise hingedly foldable wings that fold over the second opposable component when the first opposable component and second opposable component are brought into opposition.

Figure 20:
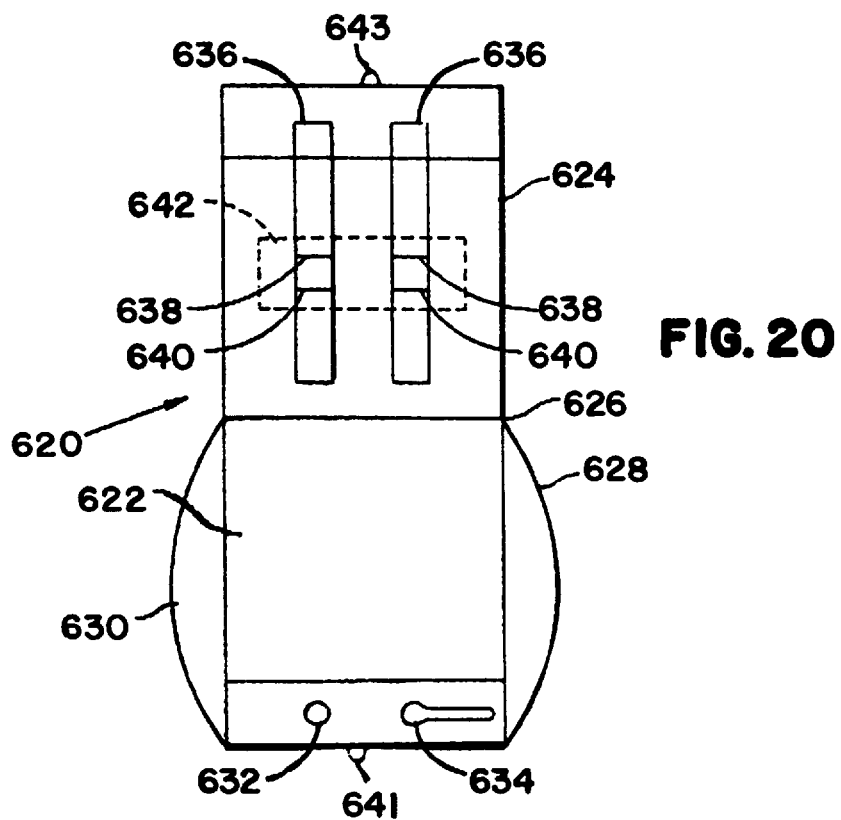
FIG. 20 is a drawing of a version of a multiplex assay device according to the present invention, containing a collapsible well to accommodate a sample.

This variation of the multiplex device is shown in FIG. 20. The device 620 has a first opposable component 622 and a second opposable component 624. The second opposable component 624 is hingedly attached to the first opposable component 622 by a hinge 626. Hingedly attached to the first opposable component 622 are two foldable wings 628 and 630. The first opposable component 622 has a control well 632 and a collapsible sample well 634, i.e., made of a sponge-like material. The second opposable component 624 has a plurality of chromatographic media 636, in this example, two, each with a detection zone 638 and a control zone 640. The second opposable component has an aperture 642 for viewing of a portion of each of the chromatographic media 636, including the detection zone 638 and the control zone 640. The first and second opposable components 622 and 624 include engagers 641 and 643. When the first opposable component 622 and the second opposable component 624 are opposed, samples in the control well 632 and the collapsible sample well 634 are applied to the corresponding chromatographic media 636 for chromatography.

3. Multiplex Devices Adapted to Receive Test Card

Yet another variation of the multiplex device is particularly useful for determination of hemoglobin in fecal occult blood. This device is adapted to receive a test card that includes several dried fecal samples, typically taken on consecutive days.

This device is shown in FIG. 21. The assay device 660 comprises a first opposable component 662, a second opposable component 664 hingedly attached to the first opposable component 662 by a first hinge 666, and a third opposable component 668 hingedly attached to the first opposable component 662 by a second hinge 670. The first opposable component 662 is adapted to receive a test card 672 that has a plurality of dried specimens 674 mounted thereon. The second opposable component 664 has a reagent pad 676 incorporated therein. The third opposable component 668 has a plurality of chromatographic media 678 each with a detection zone 680 and a control zone 682 as described above. There is a separate chromatographic medium 678 for each sample to be tested. The third opposable component 668 has an aperture 684 to permit viewing of at least a portion of the chromatographic media 678, including each detection zone 680 and control zone 682. The second and third opposable components include engagers 681 and 685, with the device 660 including a gasket 686 as described above for three-component devices.

In use, the test card 672 containing the plurality of dried specimens 674 is inserted into the second opposable component 664. The second opposable component 664 is folded over the first opposable component 662, containing the reagent pads 676, so that the reagent pads 676 contact the plurality of dried specimens 674 in the test card 672 and extracts analyte from the dried specimens 674. The second opposable component 664 is then unfolded from the first opposable component 662. Finally, the third opposable component 668 is folded over the first opposable component 662 to apply the contents of the reagent pads 676 and the analyte extracted from the dried specimens 674 to the chromatographic media 678 so that chromatography can occur.

In this device, the reagent pad 676 comprises a specific binding partner for the analyte labeled with a detectable label in a form that can be resolubilized by the addition of an aqueous reagent to the reagent pad 676. The reagent added is an extraction reagent for the analyte to be assayed, such as hemoglobin.

When the second opposable component 664 is opposed to the first opposable component 662, the analyte is extracted from the samples on the test card 672 and binds to the labeled specific binding partner. When the third opposable component 668 is subsequently opposed to the second opposable component, any analyte bound to the labeled specific binding partner migrates through the chromatographic media 668, and binds to the detection zone 680 in each of the chromatographic media 678.

Yet another variation of a multiplex device according to the present invention is a multiplex device similar to that shown in FIG. 19, but adapted to receive a test card. The test card can contain a plurality of samples, such as dried fecal samples when a fecal occult blood test is performed.

This variation is shown in FIG. 22. The assay device 700 has a first opposable component 702 and a second opposable component 704. The second opposable component 704 is hingedly attached to the first opposable component 702 by a hinge 706. The first opposable component 702 comprises a plurality of chromatographic media 708. Each of the chromatographic media 708 has a first end 710 and a second end 712, and comprises a detection zone 718 and a control zone 720. The first end 710 of each chromatographic medium 708 is in operable contact with a conductor 714, and the second end 712 of each chromatographic medium 708 is in operable contact with an absorber 716. There is a separate conductor 714 and absorber 716 for each chromatographic medium 708. The first opposable component 702 is adapted to receive a test card 722 containing a plurality of dried specimens 724 positioned so that they are in operable contact with each conductor 714. The second opposable component 704 comprises a plurality of applicators 726, one for each chromatographic medium 708. Preferably, each applicator 726 contains labeled specific binding partner for the analyte in resolubilizable form.

In use, a buffer or other aqueous liquid is applied to each applicator 726 to reconstitute the labeled specific binding partner. Bringing the first and second opposable components 702 and 704 into opposition causes each of the applicators 726 to be applied to the corresponding dried specimen 724 so that the contents of each dried specimen 724 and each applicator 726 are applied to each conductor 714, and thus to each chromatographic medium 708. The test card 722 holds each of the specimens 724 in position so that they can receive the contents of the applicators 726, and so that analyte in the specimens 724 is extracted, reacts with the labeled specific binding partner, is applied to the conductors 714. The second opposable component 704 contains a plurality of apertures 728, one for each chromatographic medium 708, for viewing of each chromatographic medium 708. The first and second opposable components 702 and 704 each includes engagers 725 and 727 and a gasket 730 to retain samples and reagents.

II. CHROMATOGRAPHIC ASSAY DEVICES FOR COMPETITIVE ASSAYS

Assay devices similar in construction to those disclosed above can be used for competitive assays for monovalent analytes. The monovalent analytes are typically haptens, but the same principles could be used to assay any analyte that is monovalent, such as a normally multivalent antigen on which the additional antibody-binding sites are blocked or modified. Assayable analytes include the following: theophylline, digoxin, disopyramide, lidocaine, procainamide, propranolol, quinidine, amikacin, penicillin and other β-lactam antibiotics, chloramphenicol, gentamicin, kanamycin, netilmycin, tobramycin, tricyclic antidepressants, ethosuximide, phenobarbital, diazepam, phenytoin, primidone, valproic acid, acetaminophen, acetylsalicylic acid, ibuprofen, methotrexate, drugs of abuse such as morphine, codeine, cocaine, fentanyl, 3-methylfentanyl, amphetamines, lysergic acid diethylamide, phencyclidine, and heroin and their metabolites, DNP, 1-substituted-4-hydroxy-2-nitrobenzenes, 4-substituted-2-nitro-trialkylanilinium salts, and environmental contaminants such as benzene, toluene, xylene, ethylbenzene, chlordane, DDT and its metabolites, 2,4-D, 2,4,5-T, and atrazine.

Specific binding partners suitable for the performance of these assays include, but are not limited to, antibodies and specific binding proteins. An example of the latter is the penicillin binding protein (PBP) isolated from *Bacillus stearothermophilus*.

Unlike previous assay devices adapted for carrying out competitive immunoassays, devices according to the present invention have the advantage that the presence of analyte in the sample gives a positive or detectable result, each as a colored line in the detection zone of the device. Typically, in competitive immunoassays, the development of a detectable signal indicates a negative result (no analyte present). Thus, an inverse relationship exists between the observed result and detection. The devices of the present invention, which yield a direct relationship between the analyte concentration and the detectable signal, are less likely to yield false negative results. These devices also possess an expanded dynamic range.

A. Three-Component Bidirectional Flow Device

One embodiment of a chromatographic assay device for competitive assays according to the present invention is a three-component bidirectional flow device.

The device has three opposable components. The first opposable component includes a chromatographic medium having a first end and a second end; the flow in the first direction is from the first end to the second end and in the second direction, from the second end to the first end. The chromatographic medium has immobilized thereon in a discrete area substantially smaller than the area of the chromatographic medium analyte or an immunological analogue thereof.

An immunological analogue is, preferably, an analyte covalently linked to a protein lacking specific binding activity for the analyte, such as normal IgG or other non-immune IgG. Such IgG is preferably is absorbed against the analyte of interest to remove any immunoglobulin fractions with specific binding activity, either natural antibodies for the analyte or antibodies capable of cross-reacting with the analyte.

The conjugation of haptens to proteins, including non-immune IgG, is well-known in the art and is described, for example, in P. Tijssen, "Practice and Theory of Enzyme Immunoassays" (Elsevier, Amsterdam, 1985) pp. 279–296, incorporated herein by this reference. Briefly, haptens containing carboxyl groups or that can be carboxylated, can be coupled by the mixed anhydride reaction, by reaction with a water-soluble carbodiimide, or esterification with N-hydroxysuccinimide. Carboxylation can be performed by reactions such as alkylation of oxygen or nitrogen substituents with haloesters, followed by hydrolysis of the ester, or the formation of hemisuccinate esters or carboxymethyloximes on hydroxyl or ketone groups of steroids.

Haptens with amino groups or nitro groups reducible to amino groups can be converted to diazonium salts and reacted with proteins at mildly alkaline pH, for aromatic amines. Haptens with aliphatic amines can be conjugated to proteins by various methods, including reaction with carbodiimides, reaction with the homobifunctional reagent tolylene-2,4-diisocyanate, or reaction with maleimide compounds. Aliphatic amines can also be converted to aromatic amines by reaction with p-nitrobenzoylchloride and subsequent reduction to a p-aminobenzoylamide, which can then be coupled to proteins after diazotization. Also, bifunctional imidate esters such as dimethylpimelimidate, dimethyladipimidate, or dimethylsuberimidate, can be used to conjugate amino group-containing haptens to proteins.

Thiol-containing haptens can be conjugated to proteins with malemides, such as 4-(N-maleimidomethyl) cyclohexane-1-carboxylic acid N-hydroxysuccinimide ester.

For haptens with hydroxyl groups, an alcohol function can be converted to the hemisuccinate, which introduces a carboxyl group available for conjugation. Alternatively, the bifunctional reagent sebacoyldichloride converts an alcohol to an acid chloride, which then reacts with proteins.

Phenols can be activated with diazotized p-aminobenzoic acid, which introduces a carboxyl group, and can then be reacted with the proteins by the mixed anhydride reaction. Sugars can be activated by forming a p-nitrophenyl glycoside, followed by reduction of the nitro group to an amino group and conjugation by diazotization. Other methods include the cleavage of vicinal glycols of sugars to aldehydes by reaction with periodate, followed by coupling to amines by reductive alkylation with sodium borohydride. Alternatively, hydroxyl containing haptens can be conjugated after conversion to chlorocarbonates by reaction with phosgene.

For haptens with aldehyde or ketone groups, carboxyl groups can be introduced through the formation of O-carboxymethyloximes. Ketone groups can also be derivatized with p-hydrazinobenzoic acid to produce carboxyl groups. Haptens containing aldehydes can be directly conjugated through the formation of Schiff bases that are stabilized by reaction with a reducing agent such as sodium borohydride.

The chromatographic medium is preferably nitrocellulose, to which the analyte analogue is bound non-covalently by a hydrophobic interaction. Other chromatographic media can be used, and the analyte analogue can alternatively be coupled covalently to the chromatographic medium.

The first opposable component further comprises a first conductor in operable contact with the first end of the chromatographic medium, and a second conductor in operable contact with the second end of the chromatographic medium.

The second opposable component includes a first applicator containing a first specific binding partner to the analyte in a form that can be resolubilized by addition of a first aqueous liquid to the first applicator. The first application liquid can be the sample; preferably, however, it is a combination of the sample and a first reconstitution fluid, with the first reconstitution fluid being applied first.

The third opposable component includes a second applicator containing a second specific binding partner to the analyte in a form that can be resolubilized by addition of a second reconstitution fluid to the second applicator. The second specific binding partner is labeled with a detectable label, preferably a visually detectable label such as a gold sol label as disclosed above. The third opposable component also includes an absorber separated from the second applicator on the third opposable component.

The first and second specific binding partners are typically antibodies to the analyte. They can be identical, but need not be. In place of intact bivalent antibodies, monovalent antibody fragments such as Fab or Fab' fragments can be used. This may be preferable for some applications, inasmuch as there is no requirement in such competitive assays for any antibody molecule to react with more than one corresponding analyte.

In use, the first specific binding partner on the first applicator is resolubilized, preferably by the application of the sample alone, or, alternatively, by the application of a first reconstitution fluid followed by the addition of the sample. The second specific binding partner on the second applicator is also reconstituted by addition of a second reconstitution fluid. Typically, the first and second reconstitution fluids are the same. The reconstitution fluid is preferably a buffer solution that can contain additional components such as chelating agents, detergents, antibacterials, and preservatives. A suitable reconstitution fluid is prepared by mixing equal volumes of phosphate buffered saline, 0.1M, pH 7.2, containing 0.8% Tween-20 and 2.5 mM HEPES buffer, pH 7.5, containing 0.005% Triton X-100, 0.003% tetrasodium EDTA, and 0.05% sodium azide. Preferably, the volume of the reconstitution fluid applied to each of the first and second applicator is from about 5 $\mu$l to about 200 $\mu$l, more preferably from about 10 $\mu$l to about 100 $\mu$l, most preferably about 20 $\mu$l. The volume of sample applied is preferably from about 5 $\mu$l to about 40 $\mu$l, most preferably about 30 $\mu$l.

After application of the sample to the first applicator, the device is incubated to allow resolubilization of the resolubilizable specific binding partner and to allow reaction of the first specific binding partner with the analyte. Preferably, this incubation is from about 5 minutes to about 30 minutes; most preferably, about 15 minutes. The incubation is typically performed at room temperature, but can be at lower or higher temperatures. Incubation at higher temperatures can speed the reaction; incubation at lower temperatures may be desirable to prevent oxidation or other breakdown of sensitive samples.

After the incubation, the first opposable component and the second opposable component are brought into opposition, applying the sample and the resolubilized first specific binding partner to the analyte to the first conductor and then into the first end of the chromatographic medium. The sample and the resolubilized specific binding partner are then allowed to move through at least a portion of the chromatographic medium and past the analyte or immunological analogue immobilized in the discrete area on the chromatographic medium. This typically requires about 10 to about 20 seconds.

At this point, the first and second opposable components are separated by opening, and the first and third opposable components are brought into opposition to bring the absorber into contact with the first conductor and to bring the second applicator into contact with the second conductor. This causes the absorber to withdraw fluid from the first end of the chromatographic medium and causes the second applicator to apply fluid, including the resolubilized labeled specific binding partner, to the second end of the chromatographic medium. Preferably, the second opposable component is then folded back over the first and third opposable components to ensure that sufficient liquid is forced out of the second applicator and absorbed by the absorber so that reversal of flow is efficient. The pressure exerted on the chromatographic medium by the folding back of the second component enhances the flow reversal.

The labeled resolubilized specific binding partner is then allowed to move through at least a portion of the chromatographic medium overlapping the portion of the chromatographic medium through which the sample and the first specific binding partner migrated, and including the discrete area containing the immobilized analyte or immunological analog. If analyte is present in the sample, the labeled specific binding partner binds in the discrete area and is detected. If the detectable label is a visually detectable label, a line is visible in the discrete area.

The assay can be performed as a qualitative assay, i.e., an on/off assay. In such an assay, the first specific binding partner is present at a concentration that binds virtually all immobilized analyte or immunological analogue thereof in the discrete area. The sites in the discrete area that are bound to the first specific binding partner are blocked to further binding. If the analyte is present in the sample, the analyte binds the first specific binding partner, which prevents the first specific binding partner from binding to the immobilized analyte or analyte analogue in the discrete area. Thus, the second, labeled, specific binding partner can bind to the analyte or immunological analogue thereof in the discrete area, giving a detectable signal.

A quantitative version can employ two or more chromatographic media within one housing, at least one being designed for a control standard to be used as a reference.

A device suitable for this version of a competitive assay is shown in FIG. 23. The chromatographic assay device 740 has a first opposable component 742, a second opposable component 744, and a third opposable component 746. The second opposable component 744 is hingedly attached to one side of the first opposable component 742 by a first hinge 748. The third opposable component 746 is hingedly attached to the other side of the first opposable component 742 by a second hinge 750. The first opposable component 742 has a chromatographic medium 752 with a first end 754 and a second end 756, with a first conductor 758 in operable contact with the first end 754 of the chromatographic medium 752 and a second conductor 760 in operable contact with the second end of the chromatographic medium 756. The chromatographic medium 752 also has a discrete area 762 of analyte or immunological analogue thereof immobilized thereon, as discussed above, which is read as the signal.

The second opposable component 744 has a first applicator 764 containing a first specific binding partner for the analyte in resolubilizable form, to which the sample preferably is applied.

The third opposable component 746 has a second applicator 766 that contains a second specific binding partner for the analyte that is labeled with a detectable label and is present in a form which can be resolubilized by addition of a second aqueous liquid to the second applicator 766. The third opposable component 746 has an absorber 768 separated from the second applicator 766. The third opposable component 746 also has an aperture 770 for viewing of at least a portion of the chromatographic medium 752, including the discrete area 762. Alternatively, an aperture 772 is located behind the discrete area 762 of the chromatographic medium 752 in the first opposable component 742 for viewing from the rear side of the device 740 when it is closed. The second and third opposable components 744 and 746 have engagers 769 and 773, and the device 740 includes a gasket 774 to contain reagents.

When the first opposable component 742 and the second opposable component 744 are brought into opposition, the first applicator 764 is brought into operable contact with the first conductor 758 to apply the contents of the first applicator 764 to the first conductor 758 and then to the first end 754 of the chromatographic medium 752. When the third opposable component 746 and the first opposable component 742 are brought into opposition, the absorber 768 is brought into operable contact with the first conductor 758 adjacent to the first end 754 of the chromatographic medium 752 and the second applicator 766 is brought into operable contact with the second conductor 760 adjacent to the second end 756 of the chromatographic medium 752, reversing the direction of fluid flow within the chromatographic medium 752.

B. Two-Component Bidirectional Flow Device with Cover

A second embodiment of a chromatographic assay device for competitive assays according to the present invention is a two-component bidirectional flow device with cover. In this embodiment, the sample to be tested is not preincubated with antibody but is applied directly to a conductor in direct contact with a chromatographic medium.

The second embodiment of the chromatographic assay device for competitive immunoassays can comprise a first opposable component and a second opposable component. The first opposable component has a chromatographic medium having a first end and second end. The chromatographic medium has immobilized thereon: (1) a first specific binding partner for the analyte; and (2) a secondary specific binding partner that is capable of binding a specific binding pair member that lacks affinity for the analyte. These components are placed on the chromatographic medium in separate discrete and non-overlapping areas. The secondary specific binding partner is located closer to the first end of the chromatographic medium than the first specific binding partner for the analyte. Preferably, the first specific binding partner is located about 0.25 inch (6.35 mm) from the secondary specific binding partner in the chromatographic medium to increase efficiency.

The first specific binding partner for the analyte is typically an antibody for the analyte or an antibody fragment, as disclosed above.

The secondary specific binding partner is typically an antibody that is capable of binding another immunoglobulin on the basis of a species-specific determinant and not on the basis of the antibody specificity, if any, of the immunoglobulin to be bound. For example, the secondary specific binding partner can be goat anti-rabbit IgG antibody, which binds all rabbit immunoglobulin G molecules, regardless of their immunological specificity.

The first opposable component also includes a first conductor in operable contact with the first end of the chromatographic medium and a second conductor in operable contact with the second end of the chromatographic medium. Preferably, the first opposable component is marked with a limit line indicating the point at which flow reversal is to occur in the bidirectional chromatographic process.

The second opposable component includes: (1) an applicator containing an analyte analogue in a form that can be resolubilized by the addition of a reconstitution fluid to the applicator; and (2) an absorber separated from the applicator.

The analyte analogue is analyte covalently linked to a member of a specific binding pair bindable by the secondary specific binding partner. The member of the specific binding pair in the analyte analogue is labeled with a detectable label. Preferably, the detectable label is a visually detectable label. Most preferably, the visually detectable label is a metal sol, such as gold, silver, or copper sol.

For example, when the secondary specific binding partner is goat anti-rabbit IgG, the member of the specific binding pair conjugated to the analyte is normal rabbit IgG without antibody activity for the analyte.

An example of an analyte analogue suitable for this version of the assay, when penicillin is the analyte, is 7-aminocephelosporanic acid covalently linked to rabbit IgG, with the rabbit IgG being labeled with colloidal gold.

Bringing the first and second opposable components into opposition places a second conductor into operable contact with the applicator so that the contents of the applicator are applied to the second conductor and are drawn through at least a portion of the chromatographic medium. It also places the absorber in operable contact with the first conductor to withdraw fluid from the first end of the chromatographic medium to reverse the flow in the chromatographic medium.

During the first phase of downward flow, the analyte present in a positive specimen passes the area of the secondary specific binding partner on the chromatographic medium unhindered and then binds the area of the first specific binding partner for the analyte. For a positive sample, during the second phase of upward flow, the labeled analyte analogue is blocked from binding to the first specific binding partner for the analyte and then binds the secondary specific binding partner. If the sample lacks analyte, there is no binding of analyte to the first specific binding partner during the downward flow phase, and the analyte analogue is bound to the first specific binding partner during the second, upward flow phase and does not reach the secondary specific binding partner, so that no signal is developed at the secondary specific binding partner.

Preferably, the device further comprises a cover hingedly attached to the first opposable component so that it can be folded over the first and second opposable components when they are opposed. The cover can have a aperture cut therein to permit viewing of at least a portion of the chromatographic medium in the first and second opposable components are opposed. Alternatively, an aperture is located behind the chromatographic medium and viewing occurs on the back side of the closed device.

This device can also contain two or more chromatographic media in one housing, at least one being designed for a control standard to be used as a reference to give a semi-quantitative or quantitative indication of the concentration of analyte present in the sample.

In another version of this embodiment, the secondary specific binding partner can be immobilized in the detection zone in multiple bands so that the labeled analyte analogue available for binding to the secondary specific binding partner is titrated. The quantity of secondary specific binding partner in each band is determined so that the quantity of analyte analogue binding to the detection zone, and thus the concentration of analyte in the test sample, is indicated by the number of bands to which the analyte analogue binds. This gives a semiquantitative estimate of analyte concentration. Typically, in this version, the band of secondary specific binding partner closest on the chromatographic medium to the first specific binding partner to the analyte has the lowest concentration of secondary specific binding partner, with each successive band having a greater concentration of secondary specific binding partner than the concentration in the lowest band.

If the concentration of analyte were sufficiently high that enough unbound labeled analyte analogue were present to saturate the first band of secondary specific binding partner, some of the labeled analyte analogue would bind to the second band of secondary specific binding partner. Thus, two lines would be visible at the detection zone of the chromatographic medium. A range of analyte concentrations is accordingly indicated by the appearance of one, two, or three lines in the detection zone.

The expected range of concentrations of the analyte to be assayed determines the concentrations that trigger the appearance of one or more lines in the detection zone. For example, using the nicotine metabolite cotinine, a 10 ppb concentration in a body fluid can indicate significant passive exposure to cigarette smoke, a 500 ppb concentration can indicate an active smoker, and a 10,000 ppb concentration can indicate a very heavy smoker. The assay device can be arranged so that one line appears at the detection zone at 10 ppb of cotinine, two lines at 500 ppb, and three lines at 10,000 ppb.

In operation, reconstitution fluid, as described above, is applied to the applicator to resolubilize the analyte analogue. The sample is then applied to the first conductor and allowed to migrate to the limit line. Typically, the chromatography in the first direction takes about 5 to about 25 seconds, more typically about 10 seconds. The second opposable component is then folded over the first opposable component so that they are in opposition. The cover is then folded over the first and second opposable components. After a period of incubation from about 30 seconds to about 10 minutes, typically about 2 minutes, a visible line is seen at the secondary specific binding partner if analyte is present in the sample. Preferred volumes of samples and reconstitution fluids are described above for the first embodiment of the competitive immunoassay device.

A device suitable for this embodiment of the competitive immunoassay is shown in FIG. 24. The chromatographic assay device 780 has a first opposable component 782, a second opposable component 784, and a cover 786. The second opposable component 784 is hingedly attached to one side of the first opposable component 782 by a first hinge 788. The cover 786 is hingedly attached to the other side of the first opposable component 782 by a second hinge 790. The first opposable component 782 has a chromatographic medium 792 with a first end 794 and a second end 796. The chromatographic medium 792 has an area of a first specific binding partner for the analyte 798 immobilized thereon, and a non-overlapping area of a secondary specific binding partner 800 immobilized thereon. The first opposable component 782 also includes a first conductor 802 in operable contact with the first end 794 of the chromatographic medium 792 and a second conductor 804 in operable contact with the second end 796 of the chromatographic medium 792. The first opposable component 782 also includes a limit line 806 to indicate the point at which the first 782 and second 784 opposable components are to be brought into opposition to reverse the direction of fluid flow during the performance of the assay.

The second opposable component 784 includes an applicator 808 containing the analyte analogue in a form that can be resolubilized by the addition of the reconstitution fluid. The second opposable component 784 also includes an absorber 810 separated from the applicator 808, and an aperture 814. When the first 782 and the second 784 opposable components are brought into opposition, the applicator 808 is placed in operable contact with the second conductor 804 and the absorber 810 is placed in operable contact with the first conductor 802 to reverse the direction of fluid flow. The cover 786 has an aperture 812 cut therein to allow viewing of a portion of the chromatographic medium 792. Preferably, the aperture 812 allows viewing of the area of the secondary specific binding partner 800 and not of the area of the first specific binding partner to the analyte 798. The second opposable component 784 and the cover 786 also include engagers 811 and 813. The device is surrounded by a gasket 815.

C. Three-Component Unidirectional Flow Device with Absorber

Another device suitable for this embodiment of the competitive immunoassay is shown in FIG. 25. This device has a third component that contains an absorber or blotter that withdraws fluid from the chromatographic medium and both conductors. The absorber extends across a substantial portion of the chromatographic medium when it is in operable contact with it. The chromatographic assay device 820 has a first opposable component 822, a second opposable component 824, and a third opposable component 826. The second opposable component 824 is hingedly attached to one side of the first opposable component 822 by a first hinge 828. The third opposable component 826 is hingedly attached to the other side of the first opposable component 822 by a second hinge 830. The first opposable component 822 has a chromatographic medium 832 with a first end 834 and a second end 836. The chromatographic medium has an area of a first specific binding partner for the analyte 840 and a non-overlapping area of a secondary specific binding partner 838 immobilized thereon. The first opposable component 822 also includes a first conductor 842, which serves as an applicator, in operable contact with the first end of the chromatographic medium 832 and a second conductor 844 in operable contact with the second end 836 of the chromatographic medium 832. The first opposable component 822 also includes a limit line to indicate the point at which the first 822 and second 824 opposable components are to be brought into opposition.

The second opposable component 824 includes a second applicator 850 containing the analyte analogue. Typically, an aqueous liquid is added to the second applicator 850 to resolubilize the analyte analogue on the second applicator 850. The second opposable component 824 also includes a first absorber 848 separated from the second applicator 850. When the first 822 and second 824 opposable components are brought into opposition, the second applicator 850 is placed in operable contact with the first conductor 842 and the first absorber 848 is placed in operable contact with the second conductor 844 to withdraw fluid. An aperture 852 is located behind the chromatographic medium allowing viewing of a portion of the chromatographic medium 832 from behind. The second and third opposable components 824 and 826 include engagers 849 and 853. The device 820 also includes a gasket 858.

The third opposable component 826 includes a second absorber 854 positioned such that it is in operable contact with a substantial area of the chromatographic medium 832 when the third 826 and first 822 opposable components are brought into opposition. This removes excess fluid from the first conductor 842 and from the second conductor 844 as well as from the chromatographic medium 832.

In use, sample is applied to the first conductor or applicator 842 and allowed to travel through the chromatographic medium 832. The third opposable component 826 is brought into opposition with the first opposable component 822 to bring the second absorber 854 into direct contact with the first conductor or applicator 842 and the chromatographic medium 832 drawing excess liquid into the second absorber 854. The second opposable component 824 and the first opposable component 822 are then opposed bringing the second applicator 850 containing resolubilized labeled analyte analogue into contact with the conductor or applicator 842 at the first end 834 of the chromatographic medium 832. Also, the first absorber 848 is brought into contact with the second conductor 844 on the second end of the chromatographic medium 832. The third opposable component 826 is then closed over the second opposable component 824 as a cover. A portion of the chromatographic medium is visible from the aperture 856 located behind the chromatographic medium 832.

Detection and/or determination of the analyte occurs in the same manner as discussed in Section II(B), above, for the bidirectional flow device.

D. Three-Component Bidirectional Flow Device Using Specificity Of Biotin

Another embodiment of a chromatographic device according to the present invention is a three-component bidirectional flow device using the specificity of the biotin-avidin link.

The first opposable component has a chromatographic medium having a first end and a second end, as described above. The chromatographic medium has immobilized thereon: (1) a substance capable of specifically binding biotin, selected from the group consisting of avidin, streptavidin, anti-biotin antibody, and derivatives thereof; and (2) a secondary specific binding partner. The secondary specific binding partner is capable of specifically binding a three-component complex, where the three-component complex comprises: (a) analyte; (b) a member of a specific binding pair lacking specific binding affinity for the analyte covalently conjugated to the analyte; and (c) a detectable label bound to the member of the specific binding pair. This three-component complex is disposed on a third opposable component as described below.

The binding components are immobilized on the chromatographic medium in separate discrete non-overlapping areas, with each area being substantially smaller than the area of the chromatographic medium. The secondary specific binding partner is immobilized in the first discrete area and is located closer to the first end of the chromatographic medium than is the substance capable of binding biotin (referred to generically herein as "avidin"), which is immobilized in the second discrete area.

The first opposable component also includes a first conductor in operable contact with the first end of the chromatographic medium and a second conductor in operable contact with the second end of the chromatographic medium.

The second opposable component includes a first applicator containing a first specific binding partner to the analyte in a form that can be resolubilized by the addition of aqueous liquid to the applicator. As disclosed above, the aqueous liquid can be, preferably, the sample alone, or a first reconstitution fluid, followed by the sample. The first specific binding partner is not capable of being bound by the secondary specific binding partner. The first specific binding partner is conjugated to biotin.

Methods for linking biotin to globular proteins, including antibodies, are well-known in the art and are described, for example, in P. Tijssen, supra, at pp 25–31, incorporated herein by this reference. Biotin can be conjugated to protein as a reactive ester, either directly or by introduction of a spacer such as ε-aminocaproic acid. Typical reactive esters are biotinyl-p-nitrophenyl ester, biotinyl-N-hydroxysuccinimide ester, and caproylamidobiotinyl-N-hydroxysuccinimide ester, the last of which provides a spacer between the biotin moiety and the protein. Biotin can also be activated by other groups.

The third opposable component includes: (1) a second applicator containing the three-component complex as described above comprising the analyte, the member of the specific binding pair lacking affinity for the analyte, and the detectable label and (2) an absorber separated from the first applicator.

In the device, bringing the first and second opposable components into opposition places the first conductor in operable contact with the first applicator so that the contents of the first applicator are applied to the first conductor and into the first end of the chromatographic medium. Thus, the contents of the first applicator migrate through at least a portion of the chromatographic medium. Bringing the first and third opposable components into opposition causes the second applicator to come into operable contact with the second conductor to apply the contents of the second applicator to the second end of the chromatographic medium, and causes the absorber to come into operable contact with the first conductor to withdraw fluid from the first end of the chromatographic medium and reverse the flow.

An example of a suitable combination of antibodies for use in this embodiment of the chromatographic assay device, with theophylline as the analyte, is biotinylated murine monoclonal anti-theophylline IgG antibody as the biotinylated first specific binding partner, goat anti-rabbit IgG antibody as the immobilized secondary specific binding partner, and rabbit IgG lacking anti-theophylline activity as the member of the specific binding pair in the three-component complex.

Another example of an analyte that can be assayed by a device according to this embodiment is penicillin, using penicillin binding protein (PBP) as the specific binding partner, and a three-component complex comprising 7-aminocephelosporanic acid covalently linked to rabbit IgG, with the rabbit IgG being labeled with colloidal gold. Other β-lactam antibiotics can be assayed similarly.

In operation, the biotinylated first specific binding partner on the first applicator is resolubilized, either, preferably by the application of the sample alone or by the application of a first reconstitution fluid followed by the application of the sample as discussed above. The three-component complex on the second applicator is resolubilized by a second reconstitution fluid, as described above in Section II(A). After a period of incubation sufficient to allow any analyte in the sample to bind to the first specific binding partner, the first and second opposable components are brought into opposition, to apply the sample and the resolubilized first specific binding partner to the first conductor and then to the first end of the chromatographic medium. The sample and the first specific binding partner migrate through the chromatographic medium and past the two discrete non-overlapping areas of immobilized reagents in the chromatographic medium. The first biotinylated specific binding partner binds the component capable of binding biotin in the second discrete area. If the analyte is present in the sample, this biotinylated specific binding partner bound to the solid support via the biotin-avidin link is itself bound to analyte. If analyte is absent from the sample, analyte is not bound to the bound biotinylated specific binding partner.

After the sample and the resolubilized first specific binding partner pass the second discrete area, the first and second opposable components are separated and the first and third opposable components are brought into opposition, reversing the flow and applying the three-component complex to the second conductor. The three-component complex then migrates through the chromatographic medium beginning at the second end toward the first end. If analyte was present in the test sample, the biotinylated specific binding partner bound to the avidin in the second discrete area cannot bind the analyte in the three-component complex, so the three-component complex reaches the secondary specific binding partner. The secondary specific binding partner then binds the member of the specific binding pair in the three-component complex, where it is detected. Typically, the third opposable component of the device has an aperture so that only the first discrete area of the secondary specific binding partner, and not the second discrete area of the avidin, is visible on the chromatographic medium when the third opposable component is in opposition with the first opposable component. However, when no analyte is in the sample, the three-component complex is bound by the first specific binding partner which is bound to the avidin, whose antigen-binding site is unoccupied. The three-component complex then does not reach the first discrete area containing the secondary specific binding partner for detection.

A chromatographic assay device suitable for performing this version of the competitive immunoassay is shown in FIG. 26. The chromatographic assay device 860 has a first opposable component 862, a second opposable component 864, and a third opposable component 866. The second opposable component 864 is hingedly attached to one side of the first opposable component 862 by a first hinge 868, and the third opposable component 866 is hingedly attached to the other side of the first opposable component 862 by a second hinge 870. The first opposable component 862 has a chromatographic medium 872 with a first end 874 and a second end 876, with a first conductor 878 in operable contact with the first end 874 of the chromatographic medium 872 and a second conductor 880 in operable contact with the second end 876 of the chromatographic medium 872. The chromatographic medium 872 has a first discrete area of a secondary specific binding partner 882 and a second discrete area of avidin 884. The first 882 and second 884 discrete areas are non-overlapping, with the first discrete area 882 being located closer to the first end 874 of the chromatographic medium 872. The second opposable component 864 has a first applicator 886 containing a resolubilizable first specific binding partner for the analyte. The third opposable component 866 has a second applicator 888 containing a resolubilizable three-component complex and an absorber 890 separated from the second applicator 888. The second opposable component 864 and the third opposable component 866 also have apertures 892 and 894 therein for viewing a portion of the chromatographic medium 872. Preferably, the apertures 892 and 894 permit viewing of the first discrete area 882 containing the secondary specific binding partner but not of the second discrete area 884 containing the avidin. The second and third opposable components 864 and 866 also include engagers 891 and 895. the device 860 also includes a gasket 896.

Bringing the first 862 and second 864 opposable components into opposition causes the first applicator 886 to come into operable contact with the first conductor 878 to begin flow through the chromatographic medium 872. Subsequently, bringing the first 862 and third 864 opposable components into opposition causes the second applicator 888 to come into operable contact with the second conductor 880 and the absorber 890 to come into operable contact with the first conductor 878, reversing direction of the flow through the chromatographic medium 872.

In a variation of this embodiment of the device, the detection zone can include two or more bands of secondary specific binding partner, as described above in Section II(B). This can titrate the quantity of labeled three-component complex available for binding to give an indication of the quantity of analyte present in the test sample by the number of visible bands in the detection zone.

E. Two-Component Device for Competitive Inhibition Immunoassays

Another embodiment of a chromatographic assay device according to the present invention is suitable for performing competitive immunoassays. This device gives a positive indication of analyte concentration by providing a detectable signal when analyte is present in the test sample.

This embodiment is a two-component device and flow is unidirectional throughout the device. The first opposable component includes a chromatographic medium having a first end and a second end. The chromatographic medium has immobilized thereon: (1) an analyte analogue capable of binding a specific binding partner for the analyte; and (2) a secondary specific binding partner that is capable of binding a specific binding pair member that has affinity for the analyte, the secondary specific binding partner itself lacking affinity for the analyte. The components are placed on the chromatographic medium in separate discrete and non-overlapping areas. The analyte analogue is located closer to the first end of the chromatographic medium than is the secondary specific binding partner.

The analyte analogue is analyte covalently linked to a protein molecule, such as a nonspecific immunoglobulin, that can be bound to the chromatographic medium. The protein molecule should not have binding affinity for analyte or for a specific binding partner to the analyte.

The secondary specific binding partner specifically binds a specific binding partner for the analyte on the basis of a species-specific determinant, as described above. The interaction between the secondary specific binding partner and the specific binding partner for the analyte does not involve the antigen-combining sites of the specific binding partner for the analyte.

The first opposable component also includes a conductor in operable contact with the first end of the chromatographic medium. Preferably, the first opposable component also includes an absorber in operable contact with the second end of the chromatographic medium.

The second opposable component includes an applicator containing a specific binding partner for the analyte labeled with a detectable label. Preferably, the detectable label is a visually detectable label such as a metal sol. In one alternative, the second opposable component can further include an absorber separated from the applicator if the first opposable component lacks an absorber. Preferably, the second opposable component also includes an aperture to allow viewing of a portion of the chromatographic medium. Preferably, the aperture allows viewing of the area of the secondary specific binding partner and not of the area of the analyte analogue.

In use, the sample to be tested is applied to the applicator to resolubilize the labeled specific binding partner. Typically, the sample is incubated with the specific binding partner for about 1 minute to about 3 minutes, although this time period can be increased if greater sensitivity is desired.

The first and second opposable components are then brought into opposition, applying the contents of the applicator to the conductor and then to the first end of the chromatographic medium. Analyte present in a positive test sample occupies the analyte-binding sites on the labeled specific binding partner, so the labeled specific binding partner does not bind to the analyte analogue on the chromatographic medium. Instead, the labeled specific binding partner proceeds to the region of the secondary specific binding partner, where it is bound, forming a detectable line that gives a positive indication of the presence of analyte.

In the absence of analyte in the test sample, all of the labeled specific binding partner for the analyte is bound by the analyte analogue and does not reach the secondary specific binding partner. The quantities of reagents used can be titrated so that the concentration of analyte required to give a positive response can be adjusted to suit clinical or pharmacological requirements.

A device suitable for this embodiment of the competitive immunoassay is shown in FIG. 27. The device 900 has a first opposable component 902 and a second opposable component 904 hingedly attached by a hinge 906. The first opposable component 902 has a chromatographic medium 908 with a first end 910 and a second end 912. The chromatographic medium 908 has an area of an analyte analogue 914 immobilized thereon, and a non-overlapping area of a secondary specific binding partner 916 immobilized thereon. The first opposable component 902 also has a conductor 918 in operable contact with the first end 910 of the chromatographic medium 908 and an absorber 920 in operable contact with the second end 912 of the chromatographic medium 908.

The second opposable component 904 includes an applicator 922 containing the labeled specific binding partner for the analyte in a form that can be resolubilized by the addition of the sample. The second opposable component 904 also includes an aperture 924 to allow viewing of at least a portion of the chromatographic medium 908. Preferably the aperture 924 allows viewing of the area of the secondary specific binding partner 916 and not of the area of the analyte analogue 914. The first and second opposable components also include engagers 923 and 925, and a gasket 926 as described above for two-component devices.

In another version of this embodiment of the device, the detection zone can include two or more bands of secondary specific binding partner to give a semiquantitative indication of analyte concentration in the test sample, as described above in Section II(B). This titrates the quantity of labeled specific binding partner available for binding to give an indication of the quantity of analyte present in the test sample by the number of bands visible in the detection zone.

III. ANALYTES AND ANTIBODIES FOR USE WITH ASSAY DEVICES

The analytes suitable for detection with an assay device according to the present invention include antigens, haptens, and antibodies. Antigens detectable with the device include hemoglobin, Streptococcus A and B antigens, antigens specific for the protozoan parasite Giardia, and viral antigens, including antigens specific for HIV and the Australia antigen specific for hepatitis. Antibodies that can be assayed include antibodies to bacteria such as *Helicobacter pylori* and to viruses, including HIV. Haptens detectable include the haptens enumerated above in Section III, supra, as well as other haptens to which antibodies of sufficient specificity can be prepared.

If the analyte is an antigen or a hapten and a sandwich procedure is used, the first and second specific binding partners are preferably antibodies. In many applications, it is preferable that the first and second specific binding partners are antibodies to different epitopes on the analyte, but this is not required. The antibodies can be polyclonal or monoclonal, and can be IgG, IgM or IgA. In many applications, polyclonal antibodies are preferred, as their natural variability may allow more accurate detection in systems where antigenic polymorphisms exist or may exist.

When the analyte is a hapten and a sandwich assay procedure is used, it is strongly preferred that the first and second specific binding partners be antibodies to different epitopes; otherwise, there may be an undesirable competition reaction set up that may interfere with binding of the complex of the labeled specific binding partner and the analyte to the immobilized second specific binding partner. It is recognized that not all haptens are large enough to accommodate more than one epitope; however, some haptens, though not large enough to induce antigen formation when injected by themselves, are nevertheless large enough that they possess more than one epitope. In cases where antibodies to more than one epitope of a hapten cannot be obtained, competitive assay procedures are generally preferred.

Where the analyte is an antibody and a sandwich assay procedure is used, the first specific binding partner is typically a labeled antibody that binds to the analyte on the basis of species, class, or subclass (isotype) specificity. It is highly preferred that the first specific binding partner to an antibody analyte binds to the constant region of the antibody analyte, in order to prevent interference. When the analyte is antibody, the second specific binding partner is preferably an antigen or hapten for which the antibody analyte is specific.

In some applications, it is desirable to employ indirect labeling. For example, in testing for Giardia antigen, an IgM antibody can be used that may be difficult to label directly. In that case, a secondary specific binding partner specific for the mobile first specific binding partner can be labeled. Typically, the labeled secondary specific binding partner binds to the antibody that is the first specific binding partner on the basis of species, class, or subclass specificity.

As an alternative to the use of a secondary specific binding partner, the first specific binding partner can be conjugated to biotin and an avidin-conjugated label can be used.

These relationships between analytes, specific binding partners, and labels for sandwich immunoassays are summarized in Table I below.

TABLE I

SCHEMES OF BINDING FOR SANDWICH IMMUNOASSAYS

| LYTE | 1ST SBP (MOBILE) | 2ND SBP (FIXED) | SECONDARY SBP | COMPLEX FORMED |
|---|---|---|---|---|
| Ag | $Ab_1$. | $Ab_2$ | — | $Ab_2$—Ag—$Ab_1$* |
| H | $Ab_1$* | $Ab_2$ | — | $Ab_2$—H—$Ab_1$*[(1)] |
| Ab | $Ab_c$* | Ag | — | Ag—Ab—$Ab_c$* |
| Ag | $Ab_1$ | $Ab_2$ | $Ab_c$* | $Ab_2$—Ag—$Ab_1$—$Ab_c$* |
| Ab | $Ab_{c1}$ | Ag | $Ab_{c2}$* | Ag—Ab—$Ab_{c1}$—$Ab_{c2}$* |
| Ag | $Ab_1$—Bi | $Ab_2$ | Av—L | $Ab_2$—Ag—$Ab_1$—Bi—Av—L |

Ag = Antigen
H = Hapten
Ab = Antibody
$Ab_1$ = 1st Antibody
$Ab_2$ = 2nd Antibody
$Ab_c$, $Ab_{c1}$, $Ab_{c2}$ = Antibody specific for another antibody
Bi = Biotin
Av = Avidin
L = Label
*Indicates labeled component
[(1)]$Ab_2$ and $Ab_1$* preferred to bind to different epitopes; not all haptens possess such different epitopes.

The relationships between analytes, specific binding partners, labels, and other participants in the reaction schemes for competitive immunoassays are shown in Table II below.

TABLE II

SCHEMES OF BINDING FOR COMPETITIVE ASSAYS

| | APPLIED TO CHROMATOGRAPHIC MEDIUM: | | FIXED TO CHROMATOGRAPHIC MEDIUM: | | BOUND IF ANALYTE PRESENT: | | BOUND IF ANALYTE ABSENT | |
|---|---|---|---|---|---|---|---|---|
| | FIRST DIRECTION | SECOND DIRECTION | FIRST SITE | SECOND SITE | FIRST SITE | SECOND SITE | FIRST SITE | SECOND SITE |
| I | H—$Ab_1$ or $Ab_1$ | $Ab_2$=L | H | — | H—$Ab_2$=L | — | H—$Ab_1$ | — |
| II | H or — | H=Ig=L | Abs | $Ab_1$ | Abs \| H=Ig=L | H—$Ab_1$ | Abs | $Ab_1$—H=Ig=L |
| III | H—$Ab_1$=Bi or $Ab_1$=Bi | H=Ig=L | Abs | Av | Abs \| H=Ig=L | H—$Ab_1$=Bi—Av | Abs | L=Ig=H—$Ab_1$ Bi=Av |
| IV | H—$Ab_1$=L or $Ab_1$=L | — | Abs | H | Abs \| H—$Ab_1$=L | H | Abs | H—$Ab_1$=L |

H: Hapten
$Ab_1$, $Ab_2$: First and second antibodies specific for hapten
Ig: Immunoglobulin lacking specific binding activity
Abs: Secondary antibody binding $Ab_1$ or $Ab_2$
Bi: Biotin
Av: Avidin
L: Label
—: Noncovalent bond
=: Covalent bond

IV. TEST KITS

Another aspect of the present invention is test kits that can be used to detect particular analytes. A test kit comprises, in separate containers:

(1) a chromatographic assay device according to the present invention;

(2) any necessary reagents required to treat or extract the sample; and (3) optionally, if the assay device does not incorporate a labeled specific binding partner to the analyte in a form that can be resolubilized, the required specific binding partner.

The components required in (2) and (3) are packaged separately and can be in liquid or solid form (freeze-dried, crystallized, precipitated, or aggregated). If the latter, they are resolubilized by the user, typically with distilled or purified water, with physiological saline, or a buffer solution.

In some cases, test kits can also include a reconstitution fluid for a reagent present on the device in resolubilizable form, either a specific binding partner or an analyte analogue. Specific examples are disclosed above, with the disclosure of the operation of each type of device.

Still other variations of test devices according to the present invention are possible. For example, any of the two-component devices described can have a cover hingedly attached to one of the opposable components. This cover can have an aperture cut therein to allow viewing of at least a portion of the chromatographic medium.

The invention is illustrated by the following Examples. The Examples are for illustrative purposes only and are not to be construed as limiting the scope of the invention in any manner.

EXAMPLES

Example 1

Construction of Device for Detecting Streptococcal Antigen

A device was constructed for detecting Streptococcus A antigen using labeled antibody to Streptococcus A antigen. The device was constructed essentially as depicted in FIG. 28.

FIG. 28 shows a chromatographic assay device 940 according to the present invention with a first opposable component 942, a second opposable component 944 hingedly attached to the first opposable component 942, and a cover 946 hingedly attached to the second opposable component 944. The first opposable component 942 includes a chromatographic medium 948. The second opposable component 944 includes a ribbon 952 that holds in place a teardrop-shaped receptacle 950 by the tension of the ribbon 952 stretched across the second opposable component 944. The teardrop-shaped receptacle 950 forms a well when held in place by the tension of the ribbon 952. The first opposable component 942 contains a first window 954 and the cover 946 contains a second window 956.

The opposable components were made of a hard, impervious plastic such as polycarbonate. The first and second opposable components, as well as the cover, each were about 3" in length; the first opposable component was about 2.25" in width, while the second opposable component and the cover was each about 2.375" in width. The second opposable component was lined with a foam rubber receptacle, into which a teardrop-shaped well was cut to accept a swab or other sampling device. The swab was held in place with a ribbon separately inserted into the second opposable component across the well.

The chromatographic medium was a nitrocellulose strip of 8 $\mu$m pore size and 0.5" in length, (MSI, Westborough, Mass.), affixed to the plastic backing by means of double-sided tape (3M, Minneapolis, Minn.). The conductor and absorber were cellulose strips (Ahlstrom Filtration, Holly Springs, Pa.), 17/32" in length for the absorber, which was Ahlstrom Grade 939, and 0.25" in length for the conductor, which was Ahlstrom Grade 1281. The detector application pad was also Ahlstrom Grade 1281, and was 0.375" wide. The detector application pad overlapped slightly with the conductor, which in turn overlapped slightly with the chromatographic medium at its first end. The chromatographic medium overlapped slightly at its second end with the absorber.

The required reagents were first incorporated in the chromatographic medium and the detector application pad, after which the device was assembled using double-sided tape to hold the components to the backing.

The detection zone comprised rabbit anti-Streptococcus A antibody at 2 mg/ml in 0.001 mole/l phosphate buffered saline, pH 7.2. The control zone comprised goat anti-rabbit IgG at a similar concentration in the same buffer. The antibody solutions were applied to the appropriate regions of the chromatographic medium and dried at 100° F. in a low humidity environment. The chromatographic medium was wet in excess blocking solution (Blocking Reagent for ELISA, Boehringer Mannheim, Mannheim, Germany, diluted 1:10 with distilled water containing 0.2% Tween 20) and again dried at 100° F.

The detector application pad contained rabbit anti-Streptococcus antibody labeled with 40-nm colloidal gold particles. To apply the labeled antibody to the detector application pad, the labeled antibody was diluted 1:1.5 with DBN (1.5 mole/l Tris-HCl, pH 7.4, 1% (v/v) Tween 20, 0.4% (v/v) Brij 35, 0.02% (w/v) sodium azide, 3 mg/ml rabbit IgG). Per test, 15 $\mu$l of diluted labeled antibody was added to the detector application pad. The detector application pad was dried for 30 minutes at 100° F.

Example 2

Detection of Streptococcal Antigen Using Device of Example 1

The device of Example 1 was used to detect Streptococcus A antigen. A woven dacron swab to which varying quantities of Streptococcus type A bacteria had been added was inserted into the sample well. Three drops of Extraction Reagent A (0.25% acetic acid, 5% Tween 20), and three drops of Extraction Reagent B (2 mole/l sodium nitrite, 5% Tween 20) were added to the swab, mixed by gently rotating the swab, and incubated for one minute. The device was then closed, so that the first and second opposable components were brought into contact, and the cover was then folded over the first opposable component. The result was read after an incubation period of from 2 minutes to 5 minutes. The development of a pink-red band in the detection zone of the chromatographic medium indicated the detection of Streptococcus A antigen.

The device of Example 1 could detect $1 \times 10^5$ Streptococcus A organisms after a 2-minute incubation, and could detect $5 \times 10^4$ Streptococcus A organisms after a 5-minute incubation. For a comparison, the Concise™ immunoassay of Hybritech (La Jolla, Calif.) could detect $1 \times 10^5$ Streptococcus A organisms only after a 5-minute incubation, and could not detect 5×10⁴ Streptococcus A organisms even after a 20-minute incubation. Similarly, the Smart™ immunoassay of New Horizons could detect 1×10⁵ Streptococcus A organisms only after a 7-minute incubation, and gave an equivocal result with 5×10⁴ Streptococcus A organisms after a 7-minute incubation.

Example 3

Device for Detecting Hemoglobin in Fecal Occult Blood (Prospective Example)

An assay device for the detection of hemoglobin in fecal occult blood is constructed according to FIGS. 1A and 1B, incorporating the optional conductor at the first end of the chromatographic medium. A labeled specific binding partner is applied to the sample application pad in resolubilizable form. The labeled specific binding partner is goat anti-human antibody labeled with colloidal gold. A fecal sample of 60 µl is applied to the sample application pad and allowed to mix with conjugate. The device is closed and the combination of the fecal sample and reconstituted antibody contacts the conductor and moves through the chromatographic medium. Chromatography is allowed to proceed for a period of about 1 minute to about 5 minutes. The chromatographic medium contains a detection zone of immobilized anti-human Hb antibody, and a control zone of immobilized rabbit anti-goat IgG antibody. Color appearing at both the detection zone and the control zone indicates a positive result, i.e., the presence of occult blood in the fecal sample. Color appearing at the control zone, but not at the detection zone, indicates the absence of occult blood and the correct performance of the test.

This device is capable of detecting hemoglobin in fecal occult blood in a concentration range of from about 0.2 ml blood/100 g feces to about 17 ml blood/100 g feces. This device is free from interference caused by peroxidase and dietary (non-human) hemoglobin.

Example 4

Competitive Immunoassay for Theophylline Using Three-Component Assay Device

A competitive immunoassay device was constructed to detect the bronchodilator theophylline. A 12-micron nitrocellulose membrane from Schleicher and Schuell (Keene, N.H.) was secured on a double-backed adhesive in 2.5 inch by ¹¹⁄₁₆ inch blocks. A theophylline analogue capable of hydrophobically binding to nitrocellulose was prepared by covalently coupling theophylline to normal rabbit immunoglobulin G by the following procedure: A solution of 8-(3-carboxypropyl)-1,3-dimethylxanthine (18 mg, 0.068 mM) in 2 ml tetrahydrofuran and 1 ml dimethylformamide was treated with N-hydroxysuccinimide (17 mg, 0.15 mM), and dicyclohexylcarbodiimide (27 mg, 0.13 mM). After standing at room temperature overnight, the reaction mixture was refrigerated for two hours and then filtered through glass wool. The crystals from the reaction mixture were washed with tetrahydrofuran and the solutions were combined. The solvents were removed under vacuum and the residue was washed with 3–4 ml diethyl ether to remove excess carbodiimide. The washed residue was washed in 1 ml dimethylformamide. Normal rabbit IgG (3.75 ml of 13.7 mg/ml solution) was then diluted to 10 ml with water. The active N-hydroxysucciminide ester was slowly added to the immunoglobulin G solution, followed by 10 µl of triethylamine. Thus the reaction mixture contained about 190 equivalents of active ester per mole of protein. The reaction mixture was allowed to stand in the refrigerator for 3 days.

Ten µl of a solution of the theophylline-rabbit IgG conjugate (1 mg/ml in 0.05M phosphate buffer) was uniformly applied via a Hamilton syringe across the upper region of the 2.5 inch length of the membranes. The membranes were dried in a dehydrator for 15 minutes, then dipped in a protein blocking solution (0.2% nonfat dried milk, 0.2% Tween-20) and redried for another 15 minutes. The line of theophylline-rabbit immunoglobulin G was designated the top of the membrane. A ¼ inch strip of Ahlstrom Cytosep 799-13 (Ahlstrom Filtration) was adhered to the top of the membrane to act as a conducting region. A second conductant band of Ahlstrom 992 membrane was secured to the lower region of the membrane. The membrane blocks were then cut into strips of ¼ inch, and stored desiccated.

For reagent pads, squares of ¼ inch×¼ inch of Lipore (Grade 9254 glass fiber filter, Lydall Technical Papers, Rochester, N.H.) were cut. For the first reagent pad, 40 µl of antitheophylline antibody (murine monoclonal, O.E.M. Concepts, Toms River, N.J.) in a concentration of 180 µg/ml of drying/stabilizing buffer (0.5M Tris-HCl, pH 7.2, 0.1% Tween-20, 0.1% Brij-35, 1.0% bovine serum albumin) was applied to the pad and dried for 2 hours. For the second reagent pad, 20 µl of a working dilution of anti-theophylline gold conjugate (E-Y Laboratories) using monoclonal anti-theophylline antibody was applied to the pad; the second reagent pad was also dried for two hours.

The membrane strips were secured in a cardboard housing such that the theophylline-rabbit IgG line was visible through the housing windows, as shown in FIG. 23. The first reagent pad containing anti-theophylline antibody was placed in the upper region of the left third of the housing so that when closed it would contact the upper conductant region on the membrane, like applicator 764 in FIG. 23. The second reagent pad containing the anti-theophylline-gold conjugate was placed in the lower region of the right third of the housing so that it would contact the lower conductant region of the membrane, like applicator 768 in FIG. 23. A 2 cm×2 cm square of Ahlstrom 270 was used as an absorbent pad and was placed in the upper region of the right third of the housing such that when the right third was closed over the center, it made contact with the upper conductant region.

Example 5

Performance Of Theophylline Assay Using Competitive Assay Device Of Example 4

(Prospective Example)

For an assay procedure 40 µl of reconstitution buffer (1 volume of phosphate buffered saline, 0.1M, pH 7.2 containing 0.8% Tween-20 and 1 volume of 2.5 mM HEPES buffer, pH 7.5 containing 0.005% Triton X-100, 0.003% tetrasodium EDTA, and 0.05% sodium azide) is added to the first reagent pad. The same volume (40 µl) of reconstitution buffer is added to the second reagent pad. The sample (10 µl) of the sample to be tested is added to the first reagent pad and incubated for 15 minutes at room temperature. The left third of the housing is closed over the center so that the contents of the first reagent pad, including the sample and the anti-theophylline antibody, are applied to the chromatographic medium. A liquid front is soon visible through the window. When the front travels half way down the membrane, in approximately 10–20 seconds, the housing is opened and the right third of the assay device, including the second reagent pad and the absorbent pad, is closed over the chromatographic medium. The left third of the device, containing the first reagent pad, is also closed over the right third and center of the device. If theophylline is present in the sample at concentrations of 1.25 μg/ml serum or greater, a visibly discernable line appears within 1 minute at the line of theophylline-rabbit immunoglobulin G.

Example 6

Conjugate Of Atrazine With Rabbit And Goat Immunoglobulin G

To demonstrate the feasibility of the conjugation of haptens to immunoglobulin G, conjugates of atrazine with rabbit and goat immunoglobulin G were prepared. For the conjugate with rabbit immunoglobulin G, rabbit IgG (34.1 mg in 5 ml of phosphate buffered saline) was treated with 12 mg thiolacetylsuccinic anhydride and 20 μl triethylamine (approximately 300 equivalents of anhydride per mole of protein). The solution was allowed to stand in the refrigerator overnight and was then dialyzed once against 2 liters of water and 4 times against 2 liters of phosphate buffered saline. A solution of hydroxylamine hydrochloride was prepared at a concentration of 63 mg/ml. To the rabbit IgG as prepared above in 8 ml PBS, was added 52 μl of the hydroxylamine solution (3.3 mg, approximately 200 equivalents). The solution was allowed to stand at room temperature for 45 minutes.

An atrazine derivative (formula I below), in which the terminal methyl group of the substituent on the nitrogen is activated, was dissolved in acetonitrile at a concentration of 19.7 mg/ml. A portion of this solution (200 eq, 16.6 mg, 844 μl) was added to the rabbit IgG-thiol solution. The solution was allowed to stand overnight at room temperature.

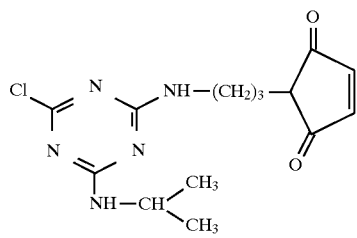

(I)

A similar procedure was used to couple the atrazine to goat immunoglobulin G. Goat IgG (7.8 mg in 1.5 ml PBS) was treated with 8 mg of thiolacetylsuccinic anhydride and 10 μl of triethylamine. The solution was allowed to stand in the refrigerator overnight and then dialyzed as for the rabbit IgG. The dialyzed goat IgG solution was treated with 10 μl hydroxylamine solution (0.75 mg, approximately 200 eq). The solution was allowed to stand at room temperature for 45 minutes. A second portion of the atrazine derivative (200 eq, 3.8 mg, 190 μl) was added to the goat IgG-thiol solution and reacted overnight. An ELISA, in which the goat IgG-atrazine conjugate was immobilized on polystyrene microtiter plates, showed that the reaction was successful.

Example 7

Competitive Immunoassay Device Using Labeled Three-Component Conjugate

A competitive immunoassay device according to the present invention for the detection of theophylline using a labeled three-component conjugate was constructed. The device was a two-component device with a cover similar to the device shown in FIG. 24, above. The orientations described here are with respect to the device oriented laterally, as shown in that figure.

Nitrocellulose membrane (12 μm pore size) (Schleicher and Schuell) was secured on double back adhesive (3M) in 2.5 inch×1 1/16 inch blocks. A block of clear plastic had already been positioned to the back side of the adhesive. Monoclonal antitheophylline antibody (see Example 4) in phosphate buffered saline (10 μl) was uniformly applied with a Hamilton syringe across the upper region of the 2.5 inch length of the nitrocellulose membrane, 5/16 inch from the designated top. Goat anti-rabbit IgG was obtained from Pel-Freez Biologicals (Rogers, Ark.). Pure IgG was obtained from the serum by precipitation with caprylic acid and ammonium sulfate. Ten μl of purified goat anti-rabbit IgG (3.5 mg/ml in phosphate buffered saline) was applied above the first line of antitheophylline antibody, 1/8 inch from the top. The membranes were dried in a circulating dehydrator for 10 minutes, then dipped in blocking solution (see Example 4) and redried for 15 minutes. A 1/4 inch band of Ahlstrom 1281 (Ahlstrom Filtration) was adhered to the top of the membrane to act as a conductant region. A second conductant band, Ahlstrom 992, was secured to the lower region. The membrane blocks were then cut into 1/4 inch strips.

For the reagent pads, 1/4×1/4 inch squares of Ahlstrom 1281 were cut. Prediluted theophylline-rabbit IgG-gold (E. Y. Laboratories) was applied to each square. The squares were dried for 2 hours. Membrane strips were secured in the housing such that the top goat anti-rabbit IgG line only was visible through the windows. The reagent pad was placed in the lower region of the left third of the housing such that when closed over the center panel it would make contact with the lower conductant region on the membrane. A 2 cm×2 cm square of Ahlstrom 270 was placed in the upper region of the left third of the housing, just above the window, where it would serve as an absorbent pad. It was positioned to contact the upper conductant region of the membrane when closed.

Example 8

Use Of Assay Device Of Example 7 For Detection Of Theophylline (Prospective Example)

For a theophylline assay using the assay device of Example 7, 40 μl of reconstitution buffer (see Example 5) was added to the reagent pad. Fifteen μl of the sample, e.g., a theophylline standard in human serum is applied to the upper conductant region on the membrane strip. The liquid front is allowed to travel to a line scored approximately 3/4 of the way down the chromatographic medium, which takes about 10 seconds. The left third of the housing is closed over the center followed by the right third over the left third to reverse the fluid flow. If theophylline is present at a threshold concentration, a visible line appears within 2 minutes.

Example 9

Two-Component Device for Competitive Inhibition Immunoassay

A two-component device was constructed using the nitrocellulose membrane strips, adhesive, and reagent pads of Example 4, supra. The device was similar to that depicted in FIG. 27, supra. The orientations described here are with respect to the device oriented laterally, as shown in that figure. Two lines were immobilized on the nitrocellulose chromatographic membrane. The first line contained 10 μl of affinity-purified goat anti-mouse IgG (O.E.M. Concepts) diluted in drying buffer (0.01M phosphate, 3.0% sucrose, 0.5% bovine serum albumin, 0.5% Tween-20, 0.05% sodium azide (pH 7.4)). The second line contained 10 μl of the theophylline-rabbit IgG conjugate of Example 4 in 0.05M phosphate buffer at 1 μg/ml. The membranes were dried in a dehydrator and dipped in protein blocking solution (0.1M Tris-HCl, 0.1% BSA, pH 7.4), then redried. For the applicator on the second opposable component, 20 μl of a working dilution of murine monoclonal anti-theophylline antibody (O.E.M. Concepts) conjugated with colloidal gold (E-Y Laboratories) was applied in drying buffer and dried for 2 hours.

For the assay, theophylline (Aldrich Chemical, Milwaukee, Wis.) was dissolved in methanol to form a stock solution and subsequent dilations were made in PBS or serum. The sample (30 μl) was added to the applicator on the second opposable component to resolubilize the anti-theophylline-gold conjugate. After a 1-minute incubation, the two opposable components were brought into opposition so that the applicator came into contact with the lower conductor on the test strip. Within 2 to 5 minutes a visually detectable line appeared at the zone of goat anti-mouse IgG antibody, the only line visible through the aperture of the housing. Concentrations as low as 1 ppb of theophylline could be detected.

Example 10

Two-Component Device for Competitive Immunoassay Yielding Semiquantitative Results A two-component device for competitive immunoassay of atrazine was constructed according to Example 9, except that the detection zone contained three lines of affinity-purified goat anti-mouse IgG (GAM) (O.E.M. Concepts), in addition to a line of atrazine-goat IgG conjugate (Example 6). The line closest on the chromatographic medium to the goat IgG-atrazine conjugate contained the most dilute antibody, at a concentration of 0.5 mg/ml; the other two lines contained more concentrated antibody, each at a concentration of 1.0 mg/ml. Murine monoclonal anti-atrazine antibody was purchased from Agri-Diagnostics (Cinnaminson, N.J.). The drying/stabilizing buffer for the anti-atrazine-gold conjugate applied to the second opposable component was 4% sucrose, 10 mM phosphate, 0.5% bovine serum albumin, 0.25% Tween-20, 0.05% sodium azide, pH 7.4.

For the assay, atrazine (Supelco, Inc., Bellefonte, Pa.) was dissolved as a standard in methanol, and subsequent dilutions were prepared in deionized water for use as working standards. Thirty μl of sample was added to the applicator on the second opposable component. After a 1 minute incubation, the two opposable components were brought together to apply the sample and the resolubilized anti-atrazine-gold to the chromatographic medium. Within three minutes, an atrazine concentration in the sample of 1 to 10 ppb gave one line on the chromatographic medium; a concentration of 11 to 100 ppb, two lines, and a concentration of 101 to 1000 ppb, three lines.

ADVANTAGES OF THE INVENTION

Chromatographic assay devices according to the present invention provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by ensuring that reagents are not wasted by being sequestered in dead volumes of apparatus. Finally, the use of opposable components provides optimum containment of possibly contaminated blood samples, each as those containing HIV or hepatitis virus.

Another advantage of assay devices according to the present invention lies in the ability of the devices to use pressure to drive fluid from one opposable component to another and through the chromatographic medium and to control the pressure applied so that it is optimum for each assay to be carried out. This accelerates the assay process and allows the performance of operations such as extraction within the assay device. It also reduces the dead volumes of reagents remaining in components, allowing the use of smaller samples and smaller quantities of expensive or hard-to-purify reagents such as labeled antibodies.

Additionally, chromatographic assay devices according to the present invention allow the rapid and accurate detection of clinically important analytes, such as Streptococcus A and B antigen, hemoglobin for the determination of fecal occult blood, and antibody to *Helicobacter pylori*, as well as clinically important i haptens. The construction of the devices allows more even application of the samples to the chromatographic medium, and reduces interference that might otherwise be introduced by particulates or colored samples. The use of colloidal metal labels in a resolubilizable form provides extremely rapid kinetics of labeling and allows substantially complete formation of binary analyte-label complexes before the sample is applied to the chromatographic medium. This aids in the separation of contaminants and improves the performance of the assay. Additionally, the construction and arrangement of the housing of the device aids in the performance of the assay by assuring the withdrawal of excess mmunoglobulin-containing sample that could otherwise create interference.

Extraction of biological samples such as blood, sputum, or feces can be performed directly in the devices, reducing the quantity of contaminated material that must be disposed and reducing the likelihood of accidental infection of physicians, technicians, or the public by such contaminated material. Additionally, the devices are capable of performing bidirectional chromatography to further increase accuracy and reduce interference. Test methods using devices according to the present invention have a wide dynamic range and are substantially free from false negatives that may occur in other test methods at high concentrations of analyte.

Although the present invention has been described with considerable detail, with reference to certain preferred versions thereof, other versions and embodiments are possible. These versions include other arrangements of two- or three-component devices that operate by the basic principles described herein and utilize any of: (a) in situ extraction of samples; (b) resolubilization of a labeled specific binding partner and rapid binding to analyte; and (c) arrangement of the chromatographic medium and absorber to remove excess sample that could otherwise create interference. These versions include assay devices adapted for competitive immunoassays as well as sandwich immunoassays, in various arrangements. In particular, devices according to the present invention can be adapted to make use of radial or circumferential flow through a chromatographic medium rather than linear flow. The present invention further encompasses variations in which the two or three components of the device are not held in a permanently fixed arrangement, but can be separated and brought together to perform the assay, such as by electrical or magnetic forces or by using a separable fastener such as a hook-and-eye fabric, for example Velcro™. Therefore, the scope of the invention is determined by the following claims.

We claim:

1. A chromatographic assay device for detection or determination of an analyte in a sample comprising:
   (a) a first opposable component including:
      (i) a chromatographic medium having first and second ends and a detection zone, the chromatographic medium having a reagent bound at the detection zone, the reagent binding specifically to an analyte to be detected or determined;
      (ii) a detector application pad either containing a mobile reagent for detection or determination of the analyte, the mobile reagent to be subsequently applied to the chromatographic medium during the performance of an assay or for application of the mobile reagent to the pad during the performance of the assay, in operable contact with the first end of the chromatographic medium;
      (iii) a conductor for allowing the passage of fluid in operable contact with the detector application pad and in direct contact with the first end of the chromatographic medium; and
      (iv) an absorber for absorbing fluid in operable contact with the second end of the chromatographic medium; and
   (b) a second opposable component including a sample preparation zone for receiving a sample, the second opposable component being attachable to the first opposable component so that the first and second opposable components are brought into opposition from a position in which they are not in opposition and fluid is transferred from the second opposable component to the first opposable component by pressure;
wherein the first and second opposable components are configured so that a sample can be applied to the sample preparation zone when the first and second opposable components are not in opposition and bringing the first and second opposable components into opposition results in the sample preparation zone being in contact with the conductor to apply the sample to be tested to the conductor for flow through the conductor and then to the first end of the chromatographic medium through the detector application pad to add the reagent for detection of the analyte to the sample, the fluid flow being aided by absorption of fluid from the absorber, so that the analyte is detected or determined within the chromatographic medium at the detection zone after migration by binding of the reagent for detection of the analyte to the analyte bound to the detection zone, the assay being either a sandwich assay or a competitive assay and the reagent for detection of the analyte being an analyte analog for a competitive assay and a labeled primary or second antibody for a sandwich assay.

2. The chromatographic assay device of claim 1 wherein the sample preparation zone on the second opposable component contains at least one reagent for treatment of the sample.

3. The chromatographic assay device of claim 1 wherein the reagent for detection is a first specific binding partner to the analyte in a form that can be resolubilized by addition of an aqueous liquid to the detector application pad, the first specific binding partner being labeled with a detectable label, and the detection zone is substantially smaller in area than the area of the chromatographic medium, the detection zone containing a second specific binding partner to the analyte immobilized thereto, such that a ternary complex comprising the first specific binding partner, the analyte, and the second specific binding partner forms at the detection zone if analyte is present in the sample.

4. The chromatographic assay device of claim 3 wherein the detectable label is a visually detectable label.

5. The chromatographic assay device of claim 1 wherein the first and second opposable components are joined by a hinge that is impermeable to an aqueous liquid.

6. A test kit for the detection and/or the determination of an analyte in a sample comprising, in separate containers:
   (a) the chromatographic assay device of claim 1; and
   (b) the reagent for detection of the analyte that is a specific binding partner for the analyte labeled with a detectable label to be applied to the detector application pad.

7. A test kit for the detection and/or the determination of an analyte in a sample comprising, in separate containers:
   (a) the chromatographic assay device of claim 3; and
   (b) an aqueous liquid for resolubilizing the first specific binding partner to the analyte labeled with a detectable label, to be applied to the detector application pad.

8. A method for the detection or the determination of an analyte in an aqueous sample comprising the steps of:
   (a) applying the aqueous sample to the sample application pad of the chromatographic assay device of claim 3;
   (b) bringing the first and second components of the chromatographic assay device into opposition, such that the sample comprises an aqueous liquid resolubilizing the labeled specific binding partner in the detector application pad, and such that the sample and the resolubilized labeled specific binding partner are applied to the conductor;
   (c) allowing the sample and the labeled specific binding partner to move through the conductor and then through at least a portion of the chromatographic medium to reach the detection zone so that the labeled specific binding partner gives a detectable indication of the presence or quantity of the analyte in the test sample; and
   (d) observing or measuring the labeled specific binding partner at the detection zone in order to detect or determine the analyte as a ternary complex at the detection zone.

9. A chromatographic assay device for detection or determination of an analyte in a sample comprising:
   (a) a first opposable component including:
      (i) a chromatographic medium having first and second ends and a detection zone and having a reagent binding specifically to an analyte to be detected or determined, the reagent being bound at the detection zone;
      (ii) a first detector application pad in operable contact with the first end of the chromatographic medium, the first detector application pad containing a first specific binding partner to the analyte in a form that can be resolubilized by the addition of an aqueous liquid to the first detector application pad, the first specific binding partner being labeled with a detectable label;
      (iii) a conductor for allowing the passage of fluid in operable contact with the first detector application pad so that the first detector application pad bridges the conductor and the first end of the chromatographic medium to allow fluid flow from the conductor through the first detector application pad and to the first end of the chromatographic medium; and (iv) an absorber for absorbing fluid in operable contact with the second end of the chromatographic medium; and (b) a second opposable component attachable to the first opposable component so that the first and second opposable components are brought into opposition and fluid is transferred from the second opposable component to the first opposable component by pressure, the second opposable component including:

(i) a sample preparation zone for receiving a sample; and (ii) a second detector application pad in operable contact with the sample preparation zone, the second detector application pad containing a second specific binding partner for the analyte in a form that can be resolubilized by the addition of a sample to the sample preparation zone, the second specific binding partner being labeled with a detectable label, the second detector application pad being located adjacent to the sample preparation zone on the second opposable component such that application of the sample to the sample preparation zone resolubilizes the second specific binding partner so that the sample preparation zone contains a mixture of the sample and the second specific binding partner;

wherein the first and second opposable components are configured so that a sample can be applied to the sample preparation zone on the second opposable component when the first and second opposable components are not in opposition and so that bringing the first and second opposable components into opposition results in the sample preparation zone on the second opposable component being in contact with the conductor on the first opposable component to apply the sample to be tested and the second specific binding partner to the conductor for flow through the conductor and then to the first end of the chromatographic medium through the first detector application pad to add the first specific binding partner to the sample and the second specific binding partner, the flow being aided by absorption of fluid by the absorber, the analyte being detected or determined at the detection zone by binding of the labeled first or second specific binding partners to the analyte bound to the detection zone.

10. The chromatographic assay device of claim 9 wherein the sample preparation zone on the second opposable component contains at least one reagent for treatment of a sample.

11. The chromatographic assay device of claim 9 wherein the first and second specific binding partners for the analyte in the first and second detector application pads are identical and the detectable labels labeling the first and second specific binding partners are identical.

12. The chromatographic assay device of claim 11 wherein the identical detectable labels are visually detectable labels.

13. The chromatographic assay device of claim 9 wherein the detection zone is substantially smaller in area than the chromatographic medium, the detection zone containing a third specific binding partner to the analyte immobilized thereto, such that a ternary complex comprising: (1) one of the first and second specific binding partners; (2) the analyte; and (3) the immobilized third specific binding partner forms at the detection zone if analyte is present in the sample.

14. A test kit for the detection and/or the determination of an analyte in a sample comprising, in separate containers:

(a) the chromatographic assay device of claim 9; and (b) an aqueous liquid for resolubilizing at least one of the first specific binding partner to the analyte and the second specific binding partner to the analyte, the aqueous liquid to be applied to at least one of the first detector application pad on the first opposable component and the second detector application pad on the second opposable component.

15. A method for the detection or the determination of an analyte in an aqueous sample comprising the steps of:

(a) applying the sample to the sample preparation zone on the second opposable component of the chromatographic assay device of claim 9 when the first and second opposable components are not in opposition;

(b) subsequent to applying the sample, brining the first and second opposable components of the chromatographic assay device into opposition, such that:

(i) the sample preparation zone on the second opposable component applies the mixture of the sample and the second specific binding partner to the conductor on the first opposable component;

(ii) the mixture of the sample and the second specific binding partner flows through the conductor to reach the first detector application pad on the first opposable component; and (iii) the mixture of the sample and the second specific binding partner is applied to the first detector application pad to resolubilize the first specific binding partner to form a mixture of the sample, the first specific binding partner, and the second specific binding partner;

(c) then allowing the mixture of the sample, the first labeled specific binding partner, and the second labeled specific binding partner to move from the first detector application pad and then through at least a portion of the chromatographic medium to reach the detection zone so that at least one of the first and second labels specific binding partners gives a detectable indication of the presence or quantity of analyte in the test sample by binding to the detection zone, the flow through the chromatographic medium being aided by absorption of fluid by the absorber; and (d) then observing or measuring at least one of the first or second specific binding partners bound to the detection zone in order to detect or determine the analyte as a ternary complex.

16. A chromatographic assay device for detection determination of an analyte in a sample comprising:

(a) a first opposable component including:

(i) a chromatographic medium having first and second ends and having a reagent binding specifically to an analyte to be detected or determined, the reagent being bound to the detection zone; and (ii) a conductor for allowing the passage of fluid in operable contact with the first end of the chromatographic medium; and (b) a second opposable component attachable to the first opposable component so that the first and second opposable component are brought into opposition from a position in which they are not in opposition and fluid is transferred from the second opposable component to the first opposable component, the second opposable component including:

(i) a sample preparation zone for receiving a sample; and (ii) an absorber for absorbing fluid separated from the sample preparation zone on the second opposable component;

wherein the first and second opposable components are configured so that a sample can be applied to the sample preparation zone on the second opposable component when the first and second opposable components are not in opposition and so that bringing the first and second opposable components into opposition results in the sample preparation zone on the second opposable component coming into operable contact with the conductor on the first opposable component to apply the sample to be tested to the conductor for flow therethrough and into the first end of the chromatographic medium, and results into the absorber coming into operable contact with the second end of the chromatographic medium to withdraw fluid from the second end of the chromatographic medium to aid fluid flow so that the analyte is detected or determined by binding of the labeled reagent to the analyte bound to the detection zone.

17. A chromatographic assay device for detection or the determination of an analyte in a sample comprising:
    (a) a first opposable component including:
        (i) a sample preparation zone for receiving a sample;
        (ii) a chromatographic medium having first and second ends and a detection zone and having a reagent binding specifically to an analyte to be detected or determined, the reagent being bound to the detection zone; and
        (iii) a conductor allowing the passage of fluid in operable contact with the sample preparation zone and with the first end of the chromatographic medium so that the conductor bridges the sample preparation zone and the chromatographic medium to allow fluid flow from the sample preparation zone through the conductor and to the first end of the chromatographic medium; and
    (b) a second opposable component attachable to the first opposable component so that the first and second opposable components are brought into opposition from a position in which they are not in opposition and fluid is transferred from the second opposable component to the first opposable component by pressure, the second opposable component including:
        (i) an applicator for applying fluid to the sample preparation zone on the first opposable component when the first and second opposable components are brought into opposition and containing a specific binding partner for an analyte labeled with a detectable label in a form that can be resolubilized by the addition of an aqueous liquid to the applicator; and
        (ii) an absorber for absorbing fluid therein separated from the applicator when the first and second opposable components are not in opposition;

wherein the first and second opposable components are configured so that a sample can be applied to the sample preparation zone on the first opposable component when the first and second opposable components are not in opposition and so that bringing the first and second opposable components into opposition results in the applicator on the second opposable component coming into operable contact with the sample preparation zone on the first opposable component such that, when a sample has been added to the sample preparation zone, the labeled specific binding partner for the analyte is resolubilized, and results in the absorber on the second opposable component coming into operable contact with the second end of the chromatographic medium on the first opposable component to withdraw fluid from the chromatographic medium to aid fluid flow so that the analyte is detected or determined by binding of the labeled specific binding partner for the analyte to the analyte bound to the detection zone.

18. A chromatographic assay device for the detection or determination of an analyte in a sample comprising:
    (a) a first opposable component including:
        (i) a chromatographic medium having first and second ends and a detection zone and having a reagent binding specifically to an analyte to be detected bound at the detection zone;
        (ii) a conductor for allowing the passage of fluid in operable contact with the first end of the chromatographic medium; and
    (b) a second opposable component attachable to the first opposable component so that the first and second opposable components are brought into opposition from a position in which they are not in opposition and fluid is transferred from the second opposable component to the first opposable component by pressure, the second opposable component including:
        (i) a first applicator for applying fluid to the conductor on the first opposable component when the first and second opposable components are brought into opposition;
        (ii) a second applicator separated on the second opposable component from the first applicator for applying fluid to the conductor on the first opposable component when the first and second opposable components are brought into opposition; and
        (iii) an absorber for absorbing fluid therein separated on the second opposable component from the first applicator and the second applicator, the first applicator and the second applicator being located on the second opposable component so that they are not in operable contact with the each other when the first and second opposable components are not in opposition, the absorber being located on the second opposable component such that it is in operable contact with the second end of the chromatographic medium when the first and second opposable components are brought into opposition;

wherein the first and second opposable components are configured so that bringing the first and second opposable components into opposition results in the conductor on the first opposable component coming into operable contact with the first applicator on the second opposable component and results in the conductor coming into operable contact with the second applicator on the second opposable component, thereby resulting in the first and second applicators coming into operable indirect contact with each other, so that the contents of the first and second applicators flow through the conductor and the chromatographic medium, the fluid flow being aided by absorption of fluid by the absorber, so that the analyte is detected or determined by binding of a labeled reagent to the analyte bound to the detection zone.

19. The chromatographic assay device of claim 18 wherein the first applicator on the second opposable component includes a sample application pad for receiving a sample when the first and second opposable components are not in opposition and the second applicator on the second opposable component includes a detector application pad either containing a labeled reagent that binds specifically to the analyte for application of the labeled reagent that binds specifically to the analyte to the conductor on the first opposable component or for application of the labeled reagent that binds specifically to the analyte to the detector application pad during the performance of the assay, whereby, when the first and second opposable components are brought into opposition, the contents of the sample application pad and the detector application pad are applied to the conductor on the first opposable component.

20. The chromatographic assay device of claim 19 wherein the reagent for detection of the analyte is a first specific binding partner to the analyte in a form that can be resolubilized by addition of an aqueous liquid to the detector application pad, the first specific binding partner being labeled with a detectable label, and the detection zone is substantially smaller in area than the chromatographic medium, the detection zone containing a second specific binding partner to the analyte immobilized thereto, such that a ternary complex comprising the first specific binding partner, the analyte, and the second specific binding partner forms at the detection zone if analyte is present in the sample.

21. The chromatographic assay device of claim wherein the detectable label is a visually detectable label.

22. A test kit for the detection and/or determination of an analyte in a sample comprising, in separate containers:
(a) the chromatographic assay device of claim 19; and
(b) the reagent for detection of the analyte, to be applied to the second applicator on the second opposable component.

23. A test kit for the detection and/or the determination of an analyte in a sample comprising, in separate containers:
(a) the chromatographic assay device of claim 20; and
(b) an aqueous liquid for resolubilizing the specific binding partner for the analyte labeled with a detectable label, to be applied to the detector application pad.

24. A method for the detection or determination of an analyte in an aqueous sample comprising the steps of:
(a) applying the sample to the first applicator of the chromatographic assay device of claim 20;
(b) bringing the first and second opposable components of the chromatographic assay device into opposition such that:
  (i) the sample comprises the aqueous liquid resolubilizing the specific binding partner in the detector application pad;
  (ii) the sample and the resolubilized labeled specific binding partner are applied to the first end of the chromatographic medium; and
  (iii) the absorber is placed in operable contact with the second end of the chromatographic medium;
(c) allowing the sample and the labeled specific binding partner to move through at least a portion of the chromatographic medium to reach the detection zone so that the labeled specific binding partner gives a detectable indication of the presence or quantity of the analyte; and
(d) observing or measuring the labeled specific binding partner at the detection zone in order to detect or determine the analyte as a ternary complex.

25. A chromatographic assay device for the detection or the determination of an analyte in a sample comprising:
(a) a first opposable component including:
  (i) a chromatographic medium having first and second ends and a detection zone and having a reagent binding specifically to an analyte to be detected or determined, the reagent being bound at the detection zone;
  (ii) a conductor for allowing the passage of fluid in operable contact with the first end of the chromatographic medium; and
  (iii) a detector application pad containing a labeled reagent that binds specifically to the analyte for detection of the analyte in direct contact with the conductor and located on the first opposable component such that it is in indirect contact with the first end of the chromatographic medium for applying the reagent for detection of the analyte to the chromatographic medium; and
(b) a second opposable component attachable to the first opposable component so that the first and second opposable components are brought into opposition from a position in which they are not in opposition and fluid is transferred from the second opposable component to the first opposable component by pressure, the second opposable component including:
  (i) a sample application pad for application of a sample thereto; and
  (ii) an absorber for absorbing fluid separated from the sample application pad on the second opposable component; wherein the first and second opposable components are configured so that a sample can be applied to the sample application pad on the second opposable component when the first and second opposable components are not in opposition and so that bringing the first and second opposable components into opposition results in:
    (1) the sample application pad on the second opposable component applying the sample to the detector application pad on the first opposable component and thus to the first end of the chromatographic medium through the conductor on the first opposable component in direct contact with the detector application pad; and
    (2) the absorber on the second opposable component being in operable contact with the second end of the chromatographic medium on the first opposable component so that the fluid flow is aided by absorption of fluid by the absorber, the analyte being detected or determined on the chromatographic medium after migration by binding of the labeled reagent to the analyte bound to the detection zone.

26. The chromatographic assay device of claim 25 wherein the reagent for detection of the analyte is a first specific binding partner to the analyte in a form that can be resolubilized by addition of an aqueous liquid to the detector application pad, the first specific binding partner being labeled with a detectable label, and the chromatographic medium further comprises a detection zone substantially smaller in area than the chromatographic medium, the detection zone containing a second specific binding partner to the analyte immobilized thereto, such that a ternary complex comprising the first specific binding partner, the analyte, and the second specific binding partner forms in the detection zone if analyte is present in the sample.

27. A method for the detection or determination of an analyte in an aqueous sample comprising the steps of:
(a) applying the sample to the sample application pad of the chromatographic assay device of claim 26;
(b) bringing the first and second components of the chromatographic assay device into opposition, such that:
  (i) the sample comprises the aqueous liquid resolubilizing the specific binding partner in the detector application pad;
  (ii) the sample and the resolubilized label specific binding partner are applied to the first end of the chromatographic medium; and (iii) the absorber of the second opposable component is brought into operable contact with the second end of the chromatographic medium;

(c) allowing the sample and the labeled specific binding partner to move through at least a portion of the chromatographic medium to reach the detection zone so that the label specific binding partner gives a detectable indication of the presence or quantity of the analyte; and (d) observing or measuring the labeled specific binding partner at the detection zone in order to detect or determine the analyte as a ternary complex.

28. A chromatographic assay device for the detection or the determination of an analyte in a sample comprising:

(a) a first opposable component including:
  (i) a chromatographic medium having first and second ends and a detection zone and having a reagent binding specifically to an analyte to be detected or determined, the reagent being bound to the detection zone; and
  (ii) a detector application pad containing a labeled reagent for detection of the analyte that binds specifically to the analyte in direct contact with the first end of the chromatographic medium for applying the reagent for detection of the analyte to the chromatographic medium; and (b) a second opposable component attachable to the first opposable component so that the first and second opposable components are brought into opposition from a position in which they are not in opposition and fluid is transferred from the second opposable component to the first opposable component by pressure, the second opposable component including:
  (i) a sample application pad for receiving a sample; and
  (ii) an absorber for absorbing fluid separated on the second opposable component from the sample application pad;

wherein the first and second opposable components are configured so that a sample can be applied to the sample application pad on the second opposable component when the first and second opposable components are not in opposition so that bringing the first and second opposable components into opposition causes the detector application pad on the first opposable component and the sample application pad on the second opposable component to come into contact except for the region of the detector application pad directly adjacent to the first end of the chromatographic medium to transfer fluid from the sample application pad to the detector application pad while minimizing the transfer of fluid from the sample application pad directly to the chromatographic medium; and wherein bringing the first and second opposable components into opposition causes:

(1) the sample to be tested to be applied to the detector application pad on the first opposable component and then to the first end of the chromatographic medium; and (2) the absorber on the second opposable component to be brought into operable contact with the second end of the chromatographic medium so that fluid flow is aided by absorption of fluid by the absorber, the analyte being detected or determined after migration by binding of the labeled reagent to the analyte bound to the detection zone.

29. The chromatographic assay device of claim 28 wherein the labeled reagent for detection of the analyte is a first specific binding partner to the analyte in a form that can be resolubilized by addition of an aqueous liquid to the detector application pad, the first specific binding partner being labeled with a detectable label, and the chromatographic medium further comprises a detection zone substantially smaller in area than the chromatographic medium, the detection zone containing a second specific binding partner to the analyte immobilized thereto, such that a ternary complex comprising the first specific binding partner, the analyte, and the second specific binding partner forms at the detection zone if analyte is present in the sample.

30. A method for the detection or determination of an analyte in an aqueous test sample comprising the steps of:

(a) applying the sample to the sample application pad on the second opposable component of the chromatographic assay device of claim 29 when the first and second opposable components are not in opposition;

(b) subsequent to applying the sample, bringing the first and second opposable components of the chromatographic assay device into opposition, such that:
  (i) the sample comprises the aqueous liquid resolubilizing the labeled specific binding partner in the detector application pad on the first opposable component;
  (ii) the sample and the resolubilized labeled specific binding partner are applied to the first end of the chromatographic medium as a result of the contact between the sample application pad and the detector application pad on the first opposable component; and
  (iii) the absorber on the second opposable component is brought into operable contact with the second end of the chromatographic medium on the first opposable component to aid fluid flow from the sample application pad and the detector application pad through the chromatographic medium;

(c) then allowing the sample and the labeled specific binding partner to move through at least a portion of the chromatographic medium to reach the detection zone so that the labeled specific binding partner gives a detectable indication of the presence or quantity of the analyte in the test sample by binding to the detection zone; and (d) then observing or measuring the labeled specific binding partner bound at the detection zone in order to detect or determine the analyte as a ternary complex.

31. A chromatographic assay device for detection or determination of an analyte in a sample comprising:

(a) a first opposable component including:
  (i) a chromatographic medium having first and second ends and a detection zone and having a reagent binding specifically to an analyte to be detected or determined, the reagent being bound to the detection zone; and
  (ii) a conductor located on the first opposable component for allowing the passage of fluid such that it is not in operable contact with the first end of the chromatographic medium when the first opposable component and the second opposable component are not in opposition; and (b) a second opposable component attachable to the first opposable component so that the first and second opposable components are brought into opposition from a position in which they are not in opposition and fluid is transferred by pressure from the second opposable component to the first opposable component, the second opposable component including:

(i) a first applicator for applying fluid to the conductor on the first opposable component when the first and second opposable components are brought into opposition;

(ii) a second applicator separated on the second opposable component from the second applicator for applying fluid to the conductor on the first opposable component when the first and second opposable components are brought into opposition; and (iii) an absorber for absorbing fluid separated on the second opposable component from the first and second applicators, the first and second applicators being positioned on the second opposable component such that they are not in operable contact with each other when the first and second opposable components are not in opposition; wherein the first and second opposable components are configured so that bringing the first and second opposable components into opposition;

(1) results in the conductor on the first opposable component coming into operable contact with the first applicator on the second opposable component, results in the conductor coming into operable contact with the second applicator on the second opposable component, and results in the second applicator coming into operable contact with the first end of the chromatographic medium, thereby placing the first and second applicators into operable indirect contact with each other to apply the contents of the first and second applicators to the chromatographic medium so that the contents of the first and second applicators flow through the chromatographic medium; and (2) results in the absorber on the second opposable component coming into operable contact with the second end of the chromatographic medium so that absorption of fluid by the absorber aids fluid flow, the analyte being detected or determined on the chromatographic medium after migration by binding of the labeled reagent to the analyte bound to the detection zone.

32. The chromatographic assay device of claim 31 wherein the first applicator on the second opposable component includes a sample application pad for application of a sample thereto when the first and second opposable components are not in opposition and the second applicator on the second opposable component includes a detector application pad either containing a detection reagent including a labeled reagent binding specifically to the analyte or for application of the detection reagent including the labeled reagent binding specifically to the analyte during the performance of the assay for application of the detection reagent to the chromatographic medium, whereby, when the first and second opposable components are brought into opposition, the contents of the sample application pad and the detector application pad are applied to the chromatographic medium through the conductor.

33. The chromatographic assay device of claim 32 wherein the detection reagent is a first specific binding partner to the analyte in a form that can be resolubilized by addition of an aqueous liquid to the detector application pad, the first specific binding partner being labeled with a detectable label, and the chromatographic medium further comprises a detection zone substantially smaller in area than the chromatographic medium, the detection zone containing a second specific binding partner to the analyte immobilized thereto, such that a ternary complex comprising the first specific binding partner, the analyte, and the second specific binding partner forms at the detection zone if analyte is present in the sample.

34. The chromatographic assay device of claim 33 wherein the detectable label is a visually detectable label.

35. A test kit for the detection and/or determination of an analyte in a sample comprising, in separate containers:

(a) the chromatographic assay device of claim 32; and (b) the labeled reagent binding specifically to the analyte, to be applied to the second applicator on the second opposable component.

36. A method for the detection or determination of an analyte in an aqueous test sample comprising the steps of:

(a) applying the sample to the first applicator on the second opposable component of the chromatographic assay device of claim 32 when the first and second opposable components are not in opposition;

(b) subsequent to applying the sample, bringing the first and second opposable components of the chromatographic assay device into opposition such that:

(i) the sample comprises the aqueous liquid resolubilizing the labeled specific binding partner in the detector application pad on the second opposable component;

(ii) the sample and the resolubilized labeled specific binding partner are applied to the first end of the chromatographic medium through the conductor on the first opposable component; and (iii) the absorber on the second opposable component is brought into operable contact with the second end of the chromatographic medium to aid fluid flow from the sample application pad and the detector application pad through the conductor and the chromatographic medium;

(c) then allowing the sample and the labeled specific binding partner to move through at least a portion of the chromatographic medium to reach the detection zone so that the labeled specific binding partner gives a detectable indication of the presence or quantity of the analyte by binding to the detection zone; and (d) then observing or measuring the labeled specific binding partner bound to the detection zone in order to detect or determine the analyte as a ternary complex.

37. A chromatographic assay device for the detection or determination of an analyte in a sample comprising:

(a) a first opposable component including:

(i) a chromatographic medium having first and second ends and a detection zone and having a reagent binding specifically to an analyte to be detected or determined bound to the detection zone;

(ii) a conductor for allowing the passage of fluid in operable contact with the first end of the chromatographic medium; and (iii) an absorber for absorbing fluid in operable contact with the second end of the chromatographic medium; and (b) a second opposable component attachable to the first opposable component so that the first and second opposable components are brought into opposition and fluid is transferred by pressure from the second opposable component to the first opposable component, the second opposable component including an applicator for applying fluid to the conductor on the first opposable component when the first and second opposable components are brought into opposition, the applicator divided into two sectors:

(i) a first sector containing a first specific binding partner for the analyte in a form that can be resolubilized by the addition of an aqueous liquid to the applicator where the first and second opposable components are not in opposition, the first specific binding partner being labeled with a detectable label; and (ii) a second sector lacking the first specific binding partner for the analyte;

wherein the first and second opposable components are configured so that bringing the first and second opposable components into opposition places the first sector, but not the second sector of the applicator on the second opposable component into direct contact with the conductor on the first opposable component, the second sector of the applicator being in indirect contact with the conductor through the first sector, to apply the contents of the first sector of the applicator to the chromatographic medium, and subsequent to the application of the contents of the first sector of the applicator to the chromatographic medium, to apply the content of the second sector of the applicator to the chromatographic medium, the absorber withdrawing fluid from the chromatographic medium to aid fluid flow, the analyte being detected or determined on the chromatographic medium after migration by binding of the labeled specific binding partner to the analyte bound to the detection zone.

38. The chromatographic assay device of claim 37 wherein the detection zone is substantially smaller in area than the chromatographic medium, the detection zone containing a second specific binding partner to the analyte immobilized thereto, such that a ternary complex comprising the first specific binding partner, the analyte, and the second specific binding partner forms at the detection zone if analyte is present in the sample.

39. The chromatographic assay device of claim 38 wherein the detectable label is a visually detectable label.

40. A method for the detection or determination of an analyte in an aqueous test sample comprising the steps of:

(a) applying the sample to the applicator on the second opposable component of the chromatographic assay device of claim 38 when the first and second opposable components are not in opposition so that the sample is applied to both the first and second sectors of the applicator;

(b) subsequent to applying the sample to the applicator, bringing the first and second opposable components of the chromatographic assay device into opposition, such that:

(i) the sample applied to the first sector of the applicator on the second opposable component comprises the aqueous liquid resolubilizing the labeled specific binding partner in the first sector of the applicator;

(ii) the sample and the resolubilized labeled specific binding partner present in the first sector of the applicator are applied to the first end of the chromatographic medium through the conductor on the first opposable component; and (iii) subsequent to the application of the sample and the resolubilized labeled specific binding partner from the first sector of the applicator to the first end of the chromatographic medium, the sample present in the second sector of the applicator is applied to the first end of the chromatographic medium through the conductor;

(c) then allowing the sample and the resolubilized labeled specific binding partner from the first sector of the applicator, followed by the sample from the second sector of the applicator, to move through at least a portion of the chromatographic medium to reach the detection zone so that the label of the labeled specific binding partner gives a detectable indication of the presence or quantity of the analyte by binding to the detection zone and so that the sample from the second sector of the applicator washes at least some labeled specific binding partner unbound to analyte from at least a portion of the chromatographic medium, the flow of fluid through the chromatographic medium being aided by withdrawal of fluid from the chromatographic medium by the absorber; and (d) then observing or measuring the label bound to the detection zone in order to detect or determine the analyte as a ternary complex.

41. A chromatographic assay device for the detection and/or determination of an immunologically monovalent analyte in a sample by a competitive immunoassay comprising:

(a) a first opposable component including:

(i) a chromatographic medium having a first end and a second end and a detection zone, the detection zone being a discrete area substantially smaller than the area of the chromatographic medium, and having immobilized in the detection zone, analyte or an immunological analog thereof;

(ii) a first conductor for allowing the passage of fluid in operable contact with the first end of the chromatographic medium; and (iii) a second conductor for allowing the passage of fluid in operable contact with the second end of the chromatographic medium;

(b) a second opposable component attachable to the first opposable component so that the first and second opposable components are brought into opposition from a position in which they are not in opposition and fluid is transferred from the second opposable component to the first opposable component, the second opposable component including a first applicator for applying fluid to the first conductor on the first opposable component when the first and second opposable components are brought into opposition, the first applicator containing a first specific binding partner to the analyte in a form that can be resolubilized by addition of a first aqueous liquid to the first applicator; and (c) a third opposable component attachable to the first opposable component so that the first and third opposable components are brought into opposition from a position in which they are not in opposition and fluid is transferred from the third opposable component to the first opposable component, the third opposable component including:

(i) a second applicator for applying fluid to the second conductor on the first opposable component when the first and third opposable components are brought into opposition, the second applicator containing a second specific binding partner to the analyte in a form that can be resolubilized by the addition of a second aqueous liquid to the second applicator, the second specific binding partner being labeled with a detectable label; and (ii) an absorber for absorbing fluid separated on the third opposable component from the second applicator; wherein the first and second opposable components are configured so that bringing the first and second opposable components into opposition places the first conductor on the first opposable component in operable contact with the first applicator on the second opposable component so that the contents of the first applicator are applied to the chromatographic medium through the first conductor and are drawn through at least a portion of the chromatographic medium; and wherein the first and third opposable components are configured so that bringing the first and third opposable components into opposition places the absorber on the third opposable component in operable contact with the first conductor on the first opposable component to withdraw fluid from the chromatographic medium through the first conductor and causes the second applicator on the third opposable component to come into operable contact with the second conductor on the first opposable component so that the contents of the second applicator are applied to the chromatographic medium and are drawn through at least a portion of the chromatographic medium overlapping the portion through which the contents of the first applicator applied to the chromatographic medium are drawn, the chromatographic assay being performed so that the analyte is detected at the detection zone by binding of the labeled reagent to the detection zone.

42. The chromatographic assay device of claim 41 wherein the first and second specific binding partners are each antibody specific for the analyte.

43. The chromatographic assay device of claim 41 wherein the immobilized analyte or analogue thereof comprises analyte covalently linked to a protein lacking specific binding activity for the analyte.

44. The chromatographic assay device of claim 41 wherein the detectable label is a visually detectable label.

45. A test kit for the detection and/or determination of an immunologically monovalent analyte in a sample comprising, in separate containers:
    (a) the chromatographic assay device of claim 41; and
    (b) an aqueous liquid for resolubilizing the second specific binding partner to the analyte.

46. A method for detecting and/or determining an immunologically monovalent analyte in an aqueous sample, comprising the steps of:
    (a) applying the sample to the first applicator of the chromatographic assay device of claim 41, the sample comprising the first aqueous liquid;
    (b) applying a reconstitution fluid to the second applicator, the reconstitution fluid comprising the second aqueous liquid;
    (c) bringing the first and second opposable components of the chromatographic assay device into opposition, such that the sample and the resolubilized first specific binding partner to the analyte are applied to the first conductor and then to the first end of the chromatographic medium;
    (d) allowing the sample and the resolubilized first specific binding partner to move through at least a portion of the chromatographic medium to reach the detection zone;
    (e) separating the first and second opposable components so that they are no longer in opposition;
    (f) bringing the first and third opposable components into opposition such that the resolubilized labeled second specific binding partner is applied to the second conductor and then to the second end of the chromatographic medium;
    (g) allowing the resolubilized labeled second specific binding partner to move through at least a portion of the chromatographic medium overlapping the portion of the chromatographic medium through which the sample and the resolubilized first specific binding partner are drawn and including the detection zone so that, in the presence of analyte in the test sample, the labeled second specific binding partner binds to the analyte or immunological analog thereof immobilized in the detection zone; and
    (h) observing and/or measuring the labeled second specific binding partner bound to the detection zone to detect and/or determine the analyte.

47. The method of claim 46 further comprising the step of incubating the chromatographic assay device following applying the sample of the first applicator in order to promote the reaction between the analyte and the first specific binding partner.

48. A method for detecting and/or determining an immunologically monovalent analyte in an aqueous sample, comprising the steps of:
    (a) applying a first reconstitution fluid to the first applicator of the chromatographic assay device of claim 41;
    (b) applying the sample to the first applicator of the chromatographic assay device of claim 45, the combination of the first reconstitution fluid and the sample comprising the first aqueous liquid;
    (c) applying a second reconstitution fluid to the second applicator, the second reconstitution fluid comprising the second aqueous liquid;
    (d) bringing the first and second opposable components of the chromatographic assay device into opposition, such that the sample and the resolubilized first specific binding partner to the analyte are applied to the first conductor and then to the first end of the chromatographic medium;
    (e) allowing the sample and the resolubilized first specific binding partner to move through at least a portion of the chromatographic medium to reach the detection zone;
    (f) separating the first and second opposable components so that they are no longer in opposition;
    (g) bringing the first and third opposable components into opposition, such that the resolubilized labeled second specific binding partner is applied to the second conductor and then to the second end of the chromatographic medium;
    (h) allowing the resolubilized labeled second specific binding partner to move through at least a portion of the chromatographic medium overlapping the portion of the chromatographic medium through which the sample and the resolubilized first specific binding partner are drawn and including the detection zone, so that, in the presence of analyte in the test sample, the labeled second specific binding partner binds the analyte or immunological analog thereof immobilized in the detection zone; and
    (i) observing and/or measuring the labeled second specific binding partner bound to the detection zone in order to detect and/or determine the analyte.

49. The method of claim 48 further comprising the step of incubating the chromatographic assay device following applying the sample to the first applicator in order to promote the reaction between the analyte and the first specific binding partner.

50. A chromatographic assay device for the detection and/or determination of an immunologically monovalent analyte in a sample by a competitive immunoassay comprising:
    (a) a first opposable component including:
        (i) a chromatographic medium having a first end and a second end and having immobilized thereon, in separate discrete and non-overlapping areas, each area being substantially smaller than the area of the chromatographic medium;
    (A) a specific binding partner for the analyte; and
    (B) a secondary specific binding partner, the secondary specific binding partner capable of binding a first member of an additional specific binding pair that specifically binds a second member of the additional specific binding pair that is covalently linked to an analyte analog. neither member of the additional specific binding pair having affinity for the analyte, the secondary specific binding partner being located closer to the first end of the chromatographic medium than the first specific binding partner;
  (ii) a first conductor in operable contact with the first end of the chromatographic medium; and
  (iii) a second conductor in operable contact with the second end of the chromatographic medium;
(b) a second opposable component including:
  (i) an applicator containing an analyte analog, the analyte analog comprising analyte covalently linked to a second member of the additional specific binding pair lacking affinity for the analyte and bindable by the secondary specific binding partner, the member of the additional specific binding pair being labeled with a detectable label, the analyte analog being in a form that can be resolubilized by the addition of an aqueous liquid to the applicator; and
  (ii) an absorber separated from the applicator;
wherein the first and second opposable components are configured so that bringing the first and second opposable components into opposition places the second conductor in operable contact with the applicator so that the contents of the applicator are applied to the chromatographic medium and are drawn through at least a portion of the chromatographic medium, and places the absorber in operable contact with the first conductor to withdraw fluid from the chromatographic medium.

51. The chromatographic assay device of claim 50 further comprising a cover hingedly attached to the first opposable component so that it can be folded over the first and second opposable components when they are opposed, the cover having an aperture cut therein to permit viewing of at least a portion of the chromatographic medium when the first and second opposable components are opposed and the cover is folded over the first and second opposable components.

52. The chromatographic assay device of claim 50 wherein the first specific binding partner is an antibody specific for the analyte and additional specific binding pair members are both antibodies.

53. The chromatographic assay device of claim 50 wherein the detectable label is a visually detectable label.

54. The chromatographic assay device of claim 50 wherein the analyte analogue comprises analyte covalently linked to an immunoglobulin.

55. The chromatographic assay device of claim 50 wherein the area of the secondary specific binding partner immobilized on the chromatographic medium is divided into at least two discrete and non-overlapping bands, with the quantity of secondary specific binding partner in each band being determined so that the quantity of analyte analogue binding to the detection zone, and thus the concentration of analyte in the test sample, is indicated by the number of bands to which the analyte analogue binds.

56. A test kit for the detection and/or determination of an immunologically monovalent analyte in a sample comprising, in separate containers:

(a) the chromatographic assay device of claim 50; and
  (b) an aqueous liquid for resolubilizing the second specific binding partner for the analyte.

57. A method for detecting and/or determining an immunologically monovalent analyte in an aqueous sample, comprising the steps of:
  (a) applying a reconstitution fluid to the applicator of the chromatographic assay device of claim 50, the reconstitution fluid comprising the aqueous liquid for reconstituting the second specific binding partner;
  (b) applying the sample to the first conductor of the chromatographic assay device;
  (c) allowing the sample to move through at least a portion of the chromatographic medium, including the first specific binding partner for the analyte immobilized in a discrete area of the chromatographic medium;
  (d) bringing the first and second opposable components into opposition such that the resolubilized labeled analyte analogue is applied to the second conductor and then to the second end of the chromatographic medium;
  (e) allowing the resolubilized labeled analyte analogue to move through at least a portion of the chromatographic medium overlapping the portion of the chromatographic medium through which the sample is drawn, including both discrete areas of immobilized reagents, so that when analyte is present in the test sample, the labeled analyte analogue binds the secondary specific binding partner; and
  (f) observing and/or measuring the labeled analyte analogue in the discrete area containing the immobilized secondary specific binding partner to detect and/or determine the analyte.

58. A method for detecting and/or determining an immunologically monovalent analyte in an aqueous sample, comprising the steps of:
  (a) applying a reconstitution fluid to the applicator of the chromatographic assay device of claim 55, the reconstitution fluid comprising the aqueous liquid for resolubilizing the second specific binding partner;
  (b) applying the sample to the first conductor of the chromatographic assay device;
  (c) allowing the sample to move through at least a portion of the chromatographic medium, including the first specific binding partner for the analyte immobilized in a discrete area of the chromatographic medium;
  (d) bringing the first and second opposable components into opposition such that the resolubilized labeled analyte analogue is applied to the second conductor and then to the second end of the chromatographic medium;
  (e) allowing the resolubilized labeled analyte analogue to move through at least a portion of the chromatographic medium overlapping the portion of the chromatographic medium through which the sample is drawn, including both discrete areas of immobilized reagents, so that when analyte is present in the test sample, the labeled analyte analogue binds the secondary specific binding partner; and
  (f) observing and/or measuring the labeled analyte analogue in the two or more bands within the discrete area containing the immobilized secondary specific binding partner to detect and/or determine the analyte, the number of bands to which labeled analyte analogue is bound increasing with analyte concentration.

59. A chromatographic assay device for the detection and/or determination of an immunologically monovalent analyte in a sample by a competitive immunoassay comprising:

(a) a first opposable component including:
  (i) a chromatographic medium having a first end and a second end and having immobilized thereon, in separate discrete and non-overlapping areas, each area being smaller than the area of the chromatographic medium:
    (A) a specific binding partner for the analyte; and
    (B) a secondary specific binding partner, the secondary specific binding partner capable of binding a first member of an additional specific binding pair that specifically binds a second member of the additional specific binding pair that is covalently linked to an analyte analog neither member of the additional specific binding pair having affinity for the analyte, the specific binding partner for the analyte being located closer to the first end of the chromatographic medium;
  (ii) a first conductor in operable contact with the first end of the chromatographic medium, the first conductor capable of functioning as a first applicator; and
  (iii) a second conductor in operable contact with the second end of the chromatographic medium;
(b) a second opposable component including:
  (i) a second applicator containing an analyte analog, the analyte analog comprising analyte covalently linked to a second member of the additional specific binding pair lacking affinity for the analyte and bindable by the secondary specific binding partner, the member of the specific binding pair being labeled with a detectable label, the analyte analog being in a form that can be resolubilized by the addition of an aqueous liquid to the applicator; and
  (ii) a first absorber separated from the second applicator; and
(c) a third opposable component including a second absorber;
wherein the first and second opposable components are configured so that bringing the first and second opposable components into opposition places the second applicator into operable contact with the first conductor and places the first absorber into operable contact with the second conductor; and
wherein the first and third opposable components are configured so that bringing the first and third opposable components into opposition places the second absorber into direct contact with the first conductor and with the chromatographic medium to withdraw fluid therefrom.

60. The assay device of claim 59 wherein the detectable label is a visually detectable label.

61. A method for detecting and/or determining an immunologically monovalent analyte in an aqueous sample, comprising the steps of:
  (a) applying the sample to the first conductor of the chromatographic assay device of claim 59;
  (b) applying a reconstitution fluid to the second applicator of the chromatographic assay device to resolubilize the labeled analyte analogue in the second applicator;
  (c) allowing the sample to move through at least a portion of the chromatographic medium, including the specific binding partner for the analyte and the secondary specific binding partner immobilized thereon;
  (d) bringing the third and first opposable components into opposition to place the second absorber into direct contact with the first conductor and with the chromatographic medium to withdraw fluid therefrom;
  (e) bringing the second and first opposable components into opposition to place the second applicator into operable contact with the first conductor to place the first absorber into operable contact with the second conductor to apply the resolubilized labeled analyte analogue to the first conductor and then to the first end of the chromatographic medium;
  (f) allowing the resolubilized labeled analyte analogue to move through at least the portion of the chromatographic medium including the specific binding partner for the analyte and the secondary specific binding partner; and
  (g) observing and/or measuring the labeled analyte analogue bound to the secondary specific binding partner in order to detect and/or determine the analyte.

62. A chromatographic assay device for the detection and/or determination of an immunologically monovalent analyte in a sample by a competitive immunoassay comprising:
(a) a first opposable component including
  (i) a chromatographic medium having a first end and a second end and having immobilized thereon, in separate discrete non-overlapping areas, each area being substantially smaller than the area of the chromatographic medium:
    (A) a substance capable of specifically binding biotin selected from the group consisting of avidin, streptavidin, anti-biotin antibody, and derivatives thereof; and
    (B) a secondary specific binding partner capable of specifically binding a three-component complex, the three-component complex comprising:
      (1) analyte;
      (2) a member of a specific binding pair lacking specific binding affinity for the analyte and capable of binding the secondary specific binding partner, the member covalently conjugated to the analyte; and
      (3) a detectable label bound to the member of the specific binding pair, the secondary specific binding partner binding the member of the specific binding pair lacking specific binding affinity for the analyte within the three-component complex;
  (ii) a first conductor in operable contact with the first end of the chromatographic medium; and
  (iii) a second conduction in operable contact with the second end of the chromatographic medium;
(b) a second opposable component including a first applicator containing a first specific binding partner to the analyte in a form that can be resolubilized by the addition of an aqueous sample to the first applicator, the first specific binding partner being covalently linked to biotin, the first specific binding partner not capable of being bound by the secondary specific binding partner; and
(c) a third opposable component including:
  (i) a second applicator containing the three-component complex, the complex being in a form that can be resolubilized by the addition of a second aqueous liquid to the second applicator; and
  (ii) an absorber separated from the second applicator;
wherein the first and second opposable components are configured so that bringing the first and second opposable components into opposition places the first conductor in operable contact with the first applicator so that the contents of the first applicator are applied to the chromatographic medium and are drawn through at least a portion of the chromatographic medium; and wherein the first and third opposable components are configured so that bringing the first and third opposable components into opposition places the absorber in contact with the first conductor to withdraw fluid from the chromatographic medium, and causes the second applicator come into operable contact with the second conductor so that the contents of the second applicator are applied to the chromatographic medium and are drawn through at least a portion of the chromatographic medium overlapping the portion through which the contents of the first applicator are drawn.

63. The chromatographic assay device of claim 62 wherein the first specific binding partner is an anti-analyte antibody.

64. The chromatographic assay device of claim 63 wherein the member of the specific binding pair in the three-component complex is rabbit immunoglobulin G and the second specific binding partner is goat anti-rabbit IgG.

65. The chromatographic assay device of claim 62 wherein the detectable label is a visually detectable label.

66. The chromatographic assay device of claim 62 wherein the substance capable of specifically binding biotin is streptavidin.

67. The chromatographic assay device of claim 62 wherein the area of the secondary specific binding partner immobilized on the chromatographic medium is divided into at least two discrete and non-overlapping bands, with the quantity of secondary specific binding partner in each band being determined so that the quantity of three-component complex binding to the detection zone, and thus the original analyte concentration in the test sample, is indicated by the number of bands to which the three-component complex binds.

68. A test kit for the detection and/or determination of an immunologically monovalent analyte in a sample comprising, in separate containers:
   (a) the chromatographic assay device of claim 62; and
   (b) an aqueous liquid for resolubilizing the three-component complex.

69. A method for detecting and/or determining an immunologically monovalent analyte in an aqueous sample, comprising the steps of:
   (a) applying the sample to the first applicator of the chromatographic assay device of claim 62, the sample comprising the first aqueous liquid;
   (b) applying a reconstitution fluid to the second applicator, the reconstitution fluid comprising the second aqueous liquid;
   (c) bringing the first and second opposable components of the chromatographic assay device into opposition such that the sample and the resolubilized first specific binding partner to the analyte are applied to the first conductor and then to the first end of the chromatographic medium;
   (d) allowing the sample and the resolubilized first specific binding partner to move through at least a portion of the chromatographic medium to at least the area of immobilized substance that specifically binds biotin;
   (e) separating the first and second opposable components so that they are no longer in opposition;
   (f) bringing the first and third opposable components into opposition, such that the resolubilized three-component complex is applied to the second conductor and then to the second end of the chromatographic medium;
   (g) allowing the resolubilized three-component complex to move through at least a portion of the chromatographic medium overlapping the portion of the chromatographic medium through which the sample and the resolubilized first specific binding partner were drawn so that, in the presence of analyte in the test sample, the three-component complex is bound to the secondary specific binding partner immobilized in one of the separate discrete non-overlapping areas; and
   (h) observing and/or measuring the labeled specific binding partner in the one of the separate discrete non-overlapping areas in order to detect and/or determine the analyte.

70. The method of claim 69 further comprising the step of incubating the chromatographic assay device following applying the sample to the first applicator in order to promote the reaction between the analyte and the first specific binding partner.

71. A method for detecting and/or determining an immunologically monovalent analyte in an aqueous sample, comprising the steps of:
   (a) applying a first reconstitution fluid to the first applicator of the chromatographic assay device of claim 62;
   (b) applying the sample to the first applicator of the chromatographic assay device of claim 62, the combination of the first reconstitution fluid and the sample comprising the first aqueous liquid;
   (c) applying a second reconstitution fluid to the second applicator, the second reconstitution fluid comprising the second aqueous liquid;
   (d) bringing the first and second opposable components of the chromatographic assay device into opposition such that the sample and the resolubilized first specific binding partner to the analyte are applied to the first conductor and then to the first end of the chromatographic medium;
   (e) allowing the sample and the resolubilized first specific binding partner to move through at least a portion of the chromatographic medium to at least the area of immobilized substance that specifically binds biotin;
   (f) separating the first and second opposable components so that they are no longer in opposition;
   (g) bringing the first and third opposable components into opposition, such that the resolubilized three-component complex is applied to the second conductor and then to the second end of the chromatographic medium;
   (h) allowing the resolubilized three-component complex to move through at least a portion of the chromatographic medium overlapping the portion of the chromatographic medium through which the sample and the resolubilized first specific binding partner are drawn so that, in the presence of analyte in the test sample, the three-component complex is bound to the secondary specific binding partner immobilized in one of the separate discrete non-overlapping areas; and
   (i) observing and/or measuring the labeled specific binding partner in one of the separate discrete non-overlapping areas in order to detect and/or determine the analyte.

72. The method of claim 71 further comprising the step of incubating the chromatographic assay device following applying the sample to the first applicator in order to promote the reaction between the analyte and the first specific binding partner.

73. A method for the detection and/or determination of an immunologically monovalent analyte in a test sample comprising the steps of:

(a) applying the sample to the first applicator of the chromatographic assay device of claim 67, the sample comprising the first aqueous liquid;

(b) applying a reconstitution fluid to the second applicator, the reconstitution fluid comprising the second aqueous liquid;

(c) bringing the first and second opposable components of the chromatographic assay device into opposition such that the sample and the resolubilized first specific binding partner to the analyte are applied to the first conductor and then to the first end of the chromatographic medium;

(d) allowing the sample and the resolubilized first specific binding partner to move through at least a portion of the chromatographic medium to at least the area of immobilized substance that specifically binds biotin;

(e) separating the first and second opposable components so that they are no longer in opposition;

(f) bringing the first and third opposable components into opposition, such that the resolubilized three-component complex is applied to the second conductor and then to the second end of the chromatographic medium;

(g) allowing the resolubilized three-component complex to move through at least a portion of the chromatographic medium overlapping the portion of the chromatographic medium through which the sample and the resolubilized first specific binding partner were drawn so that, in the presence of analyte in the test sample, the three-component complex is bound to the secondary specific binding partner immobilized in one of the separate discrete non-overlapping areas; and (h) observing and/or measuring the labeled analyte analog in the two or more bands within one of the separate discrete non-overlapping areas containing the immobilized secondary specific binding partner to detect and/or determine the analyte, the number of bands to which labeled analyte analog is bound increasing with analyte concentration.

74. A chromatographic assay device for the detection and/or determination of an immunologically monovalent analyte in a sample by a competitive immunoassay comprising:

(a) a first opposable component including:

(i) a chromatographic medium having a first end and a second end, and having immobilized thereon in separate and non-overlapping discrete areas each substantially smaller than the area of the chromatographic medium:

(A) an analyte analog capable of binding a specific binding partner for the analyte; and (B) a secondary specific binding partner that is capable of binding a specific binding pair member that has affinity for the analyte, the secondary specific binding partner itself lacking binding affinity for the analyte; and (ii) a conductor in operable contact with the first end of the chromatographic medium; and (b) a second opposable component including an applicator containing a specific binding partner to the analyte in a form that can be resolubilized by addition of an aqueous liquid to the applicator, the specific binding partner contained in the applicator being labeled with a detectable label;

wherein the first and second opposable components are configured so that bringing the first and second opposable components into opposition places the conductor in operable contact with the applicator so that the contents of the applicator are applied to the chromatographic medium and are drawn through at least a portion of the chromatographic medium.

75. The chromatographic assay device of claim 74 wherein the specific binding partner contained in the applicator is antibody specific for the analyte.

76. The chromatographic assay device of claim 74 wherein the analyte analogue comprises analyte covalently linked to a protein lacking specific binding activity for the analyte or for the specific binding partner for the analyte.

77. The chromatographic assay device of claim 75 wherein the secondary specific binding partner binds the antibody specific for the analyte on the basis of species-specific interactions not involving the antigen-combining site of the antibody for the analyte.

78. The chromatographic assay device of claim 74 wherein the detectable label is a visually detectable label.

79. The chromatographic assay device of claim 74 wherein the first opposable component further includes an absorber in operable contact with the second end of the chromatographic medium.

80. The chromatographic assay device of claim 74 wherein the second opposable component further includes an absorber separated from the applicator, the absorber being positioned on the second opposable component so that bringing the first and second opposable components into opposition places the absorber into operable contact with the second end of the chromatographic medium.

81. The chromatographic assay device of claim 74 wherein the area of the secondary specific binding partner immobilized on the chromatographic medium is divided into at least two discrete and non-overlapping bands, with the quantity of secondary specific binding partner in each band being determined so that the quantity of labeled specific binding partner for the analyte binding to the detection zone, and thus the quantity of analyte in the test sample, is indicated by the number of bands to which the labeled specific binding partner for the analyte binds.

82. A method for detecting and/or determining an immunologically monovalent analyte in an aqueous sample, comprising the steps of:

(a) applying the sample to the applicator of the chromatographic assay device of claim 74, the sample comprising the aqueous liquid;

(b) bringing the first and second opposable components of the chromatographic assay device into opposition, such that the sample and the resolubilized labeled specific binding partner to the analyte are applied to the conductor and then to the first end of the chromatographic medium;

(c) allowing the sample and the resolubilized labeled specific binding partner to move through at least a portion of the chromatographic medium, the portion including at least the separate discrete and non-overlapping areas of the analyte analogue and the secondary specific binding partner; and (d) observing and/or measuring the labeled specific binding partner in the discrete area of the secondary specific binding partner to detect and/or determine the analyte.

83. A method for detecting and/or determining an immunologically monovalent analyte in an aqueous sample, comprising the steps of:

(a) applying the sample to the applicator of i the chromatographic assay device of claim 81, the sample comprising the aqueous liquid;

(b) bringing the first and second opposable components of the chromatographic assay device into opposition, such that the sample and the resolubilized labeled specific binding partner to the analyte are applied to the conductor and then to the first end of the chromatographic medium;

(c) allowing the sample and the resolubilized labeled specific binding partner to move through at least a portion of the chromatographic medium, the portion including at least the separate discrete and non-overlapping areas of the analyte analogue and the secondary specific binding partner; and (d) observing and/or measuring the labeled specific binding partner in the two or more bands within the discrete area containing the immobilized secondary specific binding partner to detect and/or determine the analyte, the number of bands to which labeled analyte analogue is bound increasing with analyte concentration.

* * * * *